(12) United States Patent
Blain

(10) Patent No.: US 8,696,721 B2
(45) Date of Patent: Apr. 15, 2014

(54) ORTHOPEDIC EXPANSION FASTENER

(75) Inventor: Jason Blain, Encinitas, CA (US)

(73) Assignee: Spinal Elements, Inc., Carlsbad, CA (US)

( * ) Notice: Subject to any disclaimer, the term of this patent is extended or adjusted under 35 U.S.C. 154(b) by 0 days.

(21) Appl. No.: 13/333,652

(22) Filed: Dec. 21, 2011

(65) Prior Publication Data

US 2012/0158056 A1    Jun. 21, 2012

Related U.S. Application Data

(62) Division of application No. 11/374,658, filed on Mar. 13, 2006, now Pat. No. 8,100,955.

(60) Provisional application No. 60/662,747, filed on Mar. 17, 2005, provisional application No. 60/708,918, filed on Aug. 17, 2005.

(51) Int. Cl.
A61B 17/86  (2006.01)
A61B 17/80  (2006.01)

(52) U.S. Cl.
USPC ............ 606/319; 606/290; 606/304; 606/313

(58) Field of Classification Search
USPC ............... 606/70–71, 280–299, 300–321; 623/17.11–17.16; 411/353, 999
See application file for complete search history.

(56) References Cited

U.S. PATENT DOCUMENTS

| | | | |
|---|---|---|---|
| 1,845,428 A * | 2/1932 | Llewellyn | 411/81 |
| 2,440,123 A | 4/1948 | Smith | |
| 2,500,993 A | 3/1950 | Mason | |
| 2,677,369 A | 5/1954 | Knowles | |
| 3,426,364 A | 2/1969 | Lumb | |
| 3,848,601 A | 11/1974 | Ma et al. | |
| 3,867,728 A | 2/1975 | Stubstad et al. | |
| 3,893,196 A | 7/1975 | Hochman | |
| 3,953,140 A * | 4/1976 | Carlstrom | 403/258 |
| 3,987,499 A | 10/1976 | Scharbach et al. | |
| 4,013,071 A | 3/1977 | Rosenberg | |
| 4,309,777 A | 1/1982 | Patil | |
| 4,349,921 A | 9/1982 | Kuntz | |

(Continued)

FOREIGN PATENT DOCUMENTS

| | | |
|---|---|---|
| CA | 1329525 | 5/1994 |
| DE | 30 27 138 A1 | 12/1981 |

(Continued)

OTHER PUBLICATIONS

International Search Report and Written Opinion for International App. No. PCT/US2006/009120, dated Oct. 20, 2006.

(Continued)

*Primary Examiner* — Matthew Lawson
(74) *Attorney, Agent, or Firm* — Knobbe, Martens, Olson & Bear, LLP

(57) ABSTRACT

Devices are disclosed for treating the vertebral column. A fastener having a fastener head comprising a screw lumen and fastener shaft is provided. In some embodiments, an external groove and one or more openings between the screw lumen and an external groove are provided. An expandable member is located at least partially in the external groove and protrudes through the one or more openings into the screw lumen. Alternative fixation systems and screw retaining assemblies are also contemplated.

20 Claims, 36 Drawing Sheets

(56) References Cited

U.S. PATENT DOCUMENTS

| | | | |
|---|---|---|---|
| 4,388,921 A | 6/1983 | Sutter et al. | |
| 4,401,112 A | 8/1983 | Rezaian | |
| 4,464,090 A | 8/1984 | Duran | |
| 4,484,570 A | 11/1984 | Sutter et al. | |
| 4,554,914 A | 11/1985 | Kapp et al. | |
| 4,599,086 A | 7/1986 | Doty | |
| 4,834,757 A | 5/1989 | Brantigan | |
| 4,892,545 A | 1/1990 | Day et al. | |
| 4,904,261 A | 2/1990 | Dove et al. | |
| 4,917,704 A | 4/1990 | Frey et al. | |
| 4,955,908 A | 9/1990 | Frey et al. | |
| 5,002,576 A | 3/1991 | Fuhrmann et al. | |
| 5,053,036 A | 10/1991 | Perren et al. | |
| 5,057,111 A | 10/1991 | Park | |
| 5,085,660 A | 2/1992 | Lin | |
| 5,147,361 A | 9/1992 | Ojima et al. | |
| 5,176,709 A | 1/1993 | Branemark | |
| 5,192,327 A | 3/1993 | Brantigan | |
| 5,269,784 A | 12/1993 | Mast | |
| 5,275,601 A | 1/1994 | Gogolewski et al. | |
| 5,304,179 A | 4/1994 | Wagner | |
| 5,306,307 A | 4/1994 | Senter et al. | |
| 5,364,399 A | 11/1994 | Lowery et al. | |
| 5,397,364 A | 3/1995 | Kozak et al. | |
| 5,458,641 A | 10/1995 | Ramirez Jimenez | |
| 5,474,555 A | 12/1995 | Puno et al. | |
| 5,501,684 A | 3/1996 | Schlapfer et al. | |
| 5,520,690 A | 5/1996 | Errico et al. | |
| 5,522,899 A | 6/1996 | Michaelson | |
| 5,534,027 A | 7/1996 | Hodorek | |
| 5,558,674 A | 9/1996 | Heggeness et al. | |
| 5,578,034 A | 11/1996 | Estes | |
| 5,607,426 A | 3/1997 | Ralph et al. | |
| 5,607,428 A | 3/1997 | Lin | |
| 5,609,635 A | 3/1997 | Michelson | |
| 5,616,144 A | 4/1997 | Yapp et al. | |
| 5,643,265 A | 7/1997 | Errico et al. | |
| 5,665,089 A | 9/1997 | Dall et al. | |
| 5,676,666 A | 10/1997 | Oxland et al. | |
| 5,681,311 A | 10/1997 | Foley et al. | |
| 5,713,900 A | 2/1998 | Benzel et al. | |
| 5,735,853 A | 4/1998 | Olerud | |
| 5,743,914 A | 4/1998 | Skiba | |
| 5,755,796 A | 5/1998 | Ibo et al. | |
| 5,807,396 A | 9/1998 | Raveh | |
| 5,810,823 A | 9/1998 | Klaue et al. | |
| 5,849,004 A * | 12/1998 | Bramlet | 606/232 |
| 5,851,207 A | 12/1998 | Cesarone | |
| 5,876,402 A | 3/1999 | Errico et al. | |
| 5,888,223 A | 3/1999 | Bray | |
| 5,902,303 A * | 5/1999 | Eckhof et al. | 606/60 |
| 5,904,683 A | 5/1999 | Pohndorf et al. | |
| 5,925,048 A | 7/1999 | Ahmad et al. | |
| 5,931,838 A | 8/1999 | Vito | |
| 5,951,558 A | 9/1999 | Fiz | |
| 5,954,722 A | 9/1999 | Bono | |
| 6,001,130 A | 12/1999 | Bryan et al. | |
| 6,030,389 A * | 2/2000 | Wagner et al. | 606/71 |
| 6,066,175 A | 5/2000 | Henderson et al. | |
| 6,117,173 A | 9/2000 | Taddia et al. | |
| 6,139,550 A | 10/2000 | Michelson | |
| 6,152,927 A | 11/2000 | Farris et al. | |
| 6,156,037 A | 12/2000 | Le Huec et al. | |
| 6,193,721 B1 | 2/2001 | Michelson | |
| 6,206,881 B1 | 3/2001 | Frigg et al. | |
| 6,231,610 B1 | 5/2001 | Geisler | |
| 6,235,033 B1 | 5/2001 | Brace et al. | |
| 6,235,034 B1 | 5/2001 | Bray | |
| 6,235,059 B1 | 5/2001 | Benezech et al. | |
| 6,241,731 B1 | 6/2001 | Fiz | |
| 6,261,291 B1 | 7/2001 | Talaber et al. | |
| 6,273,889 B1 | 8/2001 | Richelsoph | |
| 6,287,309 B1 | 9/2001 | Baccelli et al. | |
| 6,302,883 B1 | 10/2001 | Bono | |
| 6,306,136 B1 | 10/2001 | Baccelli | |
| 6,306,139 B1 | 10/2001 | Fuentes | |
| 6,331,179 B1 | 12/2001 | Freid et al. | |
| 6,342,055 B1 | 1/2002 | Eisermann et al. | |
| 6,383,186 B1 | 5/2002 | Michelson | |
| 6,402,755 B1 | 6/2002 | Pisharodi | |
| 6,413,259 B1 | 7/2002 | Lyons et al. | |
| 6,428,542 B1 | 8/2002 | Michelson | |
| 6,432,106 B1 | 8/2002 | Fraser | |
| 6,454,769 B2 | 9/2002 | Wagner et al. | |
| 6,461,359 B1 | 10/2002 | Tribus et al. | |
| 6,503,250 B2 | 1/2003 | Paul | |
| 6,508,818 B2 | 1/2003 | Steiner et al. | |
| 6,565,570 B2 | 5/2003 | Sterett et al. | |
| 6,575,975 B2 | 6/2003 | Brace et al. | |
| 6,579,290 B1 * | 6/2003 | Hardcastle et al. | 606/247 |
| 6,599,290 B2 | 7/2003 | Bailey et al. | |
| 6,602,255 B1 | 8/2003 | Campbell et al. | |
| 6,602,256 B1 | 8/2003 | Hayes | |
| 6,613,053 B1 | 9/2003 | Collins et al. | |
| 6,623,486 B1 | 9/2003 | Weaver et al. | |
| 6,626,907 B2 | 9/2003 | Campbell et al. | |
| 6,626,911 B1 | 9/2003 | Engman et al. | |
| 6,645,208 B2 | 11/2003 | Apfelbaum et al. | |
| 6,645,209 B2 | 11/2003 | Hall, IV et al. | |
| 6,652,525 B1 | 11/2003 | Assaker et al. | |
| 6,656,181 B2 | 12/2003 | Dixon et al. | |
| 6,669,700 B1 | 12/2003 | Farris et al. | |
| 6,682,561 B2 | 1/2004 | Songer et al. | |
| 6,682,563 B2 | 1/2004 | Scharf | |
| 6,695,845 B2 | 2/2004 | Dixon et al. | |
| 6,695,846 B2 | 2/2004 | Richelsoph et al. | |
| 6,702,817 B2 | 3/2004 | Beger et al. | |
| 6,730,127 B2 | 5/2004 | Michelson | |
| 6,740,087 B2 | 5/2004 | Knox | |
| 6,746,450 B1 | 6/2004 | Wall et al. | |
| 6,755,833 B1 | 6/2004 | Paul et al. | |
| 6,780,186 B2 | 8/2004 | Errico et al. | |
| 6,884,242 B2 | 4/2005 | Le Huec et al. | |
| 6,890,334 B2 * | 5/2005 | Brace et al. | 606/281 |
| 6,890,335 B2 | 5/2005 | Grabowski et al. | |
| 6,964,664 B2 | 11/2005 | Freid et al. | |
| 6,984,234 B2 | 1/2006 | Bray | |
| 7,001,389 B1 | 2/2006 | Navarro et al. | |
| 7,025,769 B1 | 4/2006 | Ferree | |
| 7,048,739 B2 | 5/2006 | Konieczynski et al. | |
| 7,063,701 B2 | 6/2006 | Michelson | |
| 7,077,844 B2 | 7/2006 | Michelson | |
| 7,112,222 B2 | 9/2006 | Fraser et al. | |
| 7,135,024 B2 | 11/2006 | Cook et al. | |
| 7,172,627 B2 | 2/2007 | Fiere et al. | |
| 7,186,254 B2 | 3/2007 | Dinh et al. | |
| 7,220,263 B2 | 5/2007 | Cordaro | |
| 7,232,464 B2 | 6/2007 | Mathieu et al. | |
| 7,273,481 B2 | 9/2007 | Lombardo et al. | |
| 7,306,605 B2 | 12/2007 | Ross | |
| 7,309,340 B2 | 12/2007 | Fallin et al. | |
| 7,481,829 B2 | 1/2009 | Baynham et al. | |
| 7,481,830 B2 | 1/2009 | Wall et al. | |
| 7,524,325 B2 | 4/2009 | Khalili | |
| 7,547,324 B2 | 6/2009 | Cragg et al. | |
| 7,621,943 B2 | 11/2009 | Michelson | |
| 7,628,816 B2 | 12/2009 | Magerl et al. | |
| 7,651,517 B2 | 1/2010 | Konieczynski et al. | |
| 7,819,903 B2 | 10/2010 | Fraser et al. | |
| 7,857,839 B2 | 12/2010 | Duong et al. | |
| 7,914,561 B2 * | 3/2011 | Konieczynski et al. | 606/280 |
| 7,931,840 B2 | 4/2011 | Michelson | |
| 7,935,137 B2 | 5/2011 | Gorhan et al. | |
| 7,963,981 B2 | 6/2011 | Binder et al. | |
| 7,972,366 B2 | 7/2011 | Richelsoph et al. | |
| 8,282,675 B2 * | 10/2012 | Maguire et al. | 606/289 |
| 2003/0093082 A1 | 5/2003 | Campbell et al. | |
| 2004/0097935 A1 | 5/2004 | Richelsoph et al. | |
| 2004/0127904 A1 * | 7/2004 | Konieczynski et al. | 606/70 |
| 2004/0176778 A1 | 9/2004 | Zubok et al. | |
| 2004/0181227 A1 | 9/2004 | Khalili | |
| 2004/0193269 A1 | 9/2004 | Fraser et al. | |
| 2004/0230192 A1 | 11/2004 | Graf | |
| 2004/0260306 A1 * | 12/2004 | Fallin et al. | 606/104 |

(56) References Cited

U.S. PATENT DOCUMENTS

| | | |
|---|---|---|
| 2005/0049593 A1 | 3/2005 | Duong et al. |
| 2005/0177245 A1 | 8/2005 | Leatherbury et al. |
| 2006/0200147 A1* | 9/2006 | Ensign et al. .................. 606/69 |
| 2006/0235403 A1 | 10/2006 | Blain |
| 2006/0235409 A1 | 10/2006 | Blain |
| 2006/0235412 A1 | 10/2006 | Blain |
| 2006/0235518 A1 | 10/2006 | Blain |
| 2006/0235533 A1 | 10/2006 | Blain |
| 2007/0055252 A1 | 3/2007 | Blain |

FOREIGN PATENT DOCUMENTS

| | | |
|---|---|---|
| DE | 30 27 138 C2 | 12/1981 |
| DE | 30 27 148 A1 | 12/1981 |
| DE | 30 27 148 C2 | 12/1981 |
| DE | 297 01 099 U1 | 4/1997 |
| DE | 197 02 201 C1 | 8/1998 |
| DE | 20 2004 015 912 | 12/2004 |
| EP | 0 242 842 A2 | 10/1987 |
| EP | 0 242 842 A3 | 10/1987 |
| EP | 0 242 842 B1 | 10/1987 |
| EP | 0 974 319 A2 | 1/2000 |
| EP | 1 346 697 A2 | 9/2003 |
| EP | 1 470 803 A1 | 10/2004 |
| FR | 2 766 353 A1 | 1/1999 |
| FR | 2859904 A1 | 3/2005 |
| JP | 2003-518977 | 6/2003 |
| JP | 2004500156 | 1/2004 |
| WO | WO 88/03781 A1 | 6/1988 |
| WO | WO 89/04150 A1 | 5/1989 |
| WO | WO 95/35067 A2 | 12/1995 |
| WO | WO 95/35067 A3 | 12/1995 |
| WO | WO 00/24343 | 5/2000 |
| WO | 0103570 | 1/2001 |
| WO | WO 01/49191 | 7/2001 |
| WO | WO 01/78615 A1 | 10/2001 |
| WO | WO 01/89428 | 11/2001 |
| WO | WO 03/017856 A1 | 3/2003 |
| WO | WO 03/071966 A1 | 9/2003 |
| WO | WO 2004/006792 A1 | 1/2004 |
| WO | WO 2005/027760 A2 | 3/2005 |
| WO | WO 2006/101837 | 9/2006 |

OTHER PUBLICATIONS

Mar. 26, 2009 Office Action for European App. No. 06738204.4, filed Mar. 14, 2006.

Apr. 6, 2010 Office Action for European App. No. 06738204.4, filed Mar. 14, 2006.

Dec. 8, 2010 Office Action for Australian App. No. 2006227755, filed Mar. 14, 2006.

Apr. 5, 2011 Office Action for European App. No. 06738204.4, filed Mar. 14, 2006.

May 10, 2011 Office Action for Japanese App. No. 2008/501962, filed Mar. 14, 2006.

Nov. 2, 2011 International Search Report and Preliminary Opinion for European App. No. 11160061.5, filed Mar. 14, 2006.

Nov. 2, 2011 International Search Report and Preliminary Opinion for European App. No. 11160063.1, filed Mar. 14, 2006.

European Search Report for European App. No. EP 11 16 0063, dated Oct. 21, 2011.

European Search Report for European App. No. EP 11 16 0061, dated Oct. 20, 2011.

Mar. 5, 2013 Office Action for Japanese Application No. 2011-210533, filed Mar. 14, 2006.

Nov. 13, 2012 Notice of Allowance for related Japanese Application No. 2008-501962.

Sep. 14, 2012 Final Office Action in related U.S. Appl. No. 11/374,462, filed Mar. 13, 2006.

Jul. 17, 2013 Patent Examination Report for Australian Application No. 2012211502, filed Aug. 10, 2012.

* cited by examiner

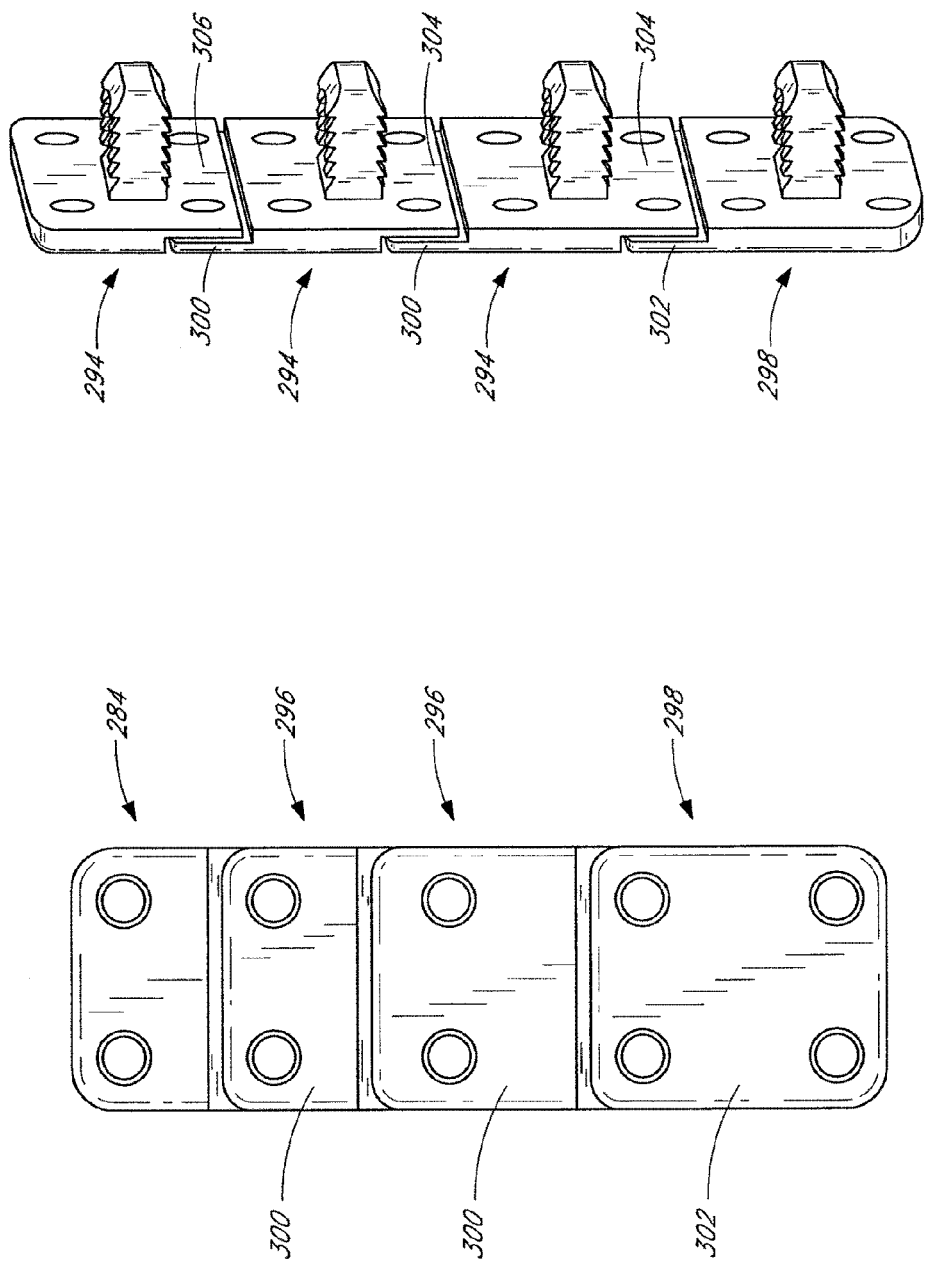

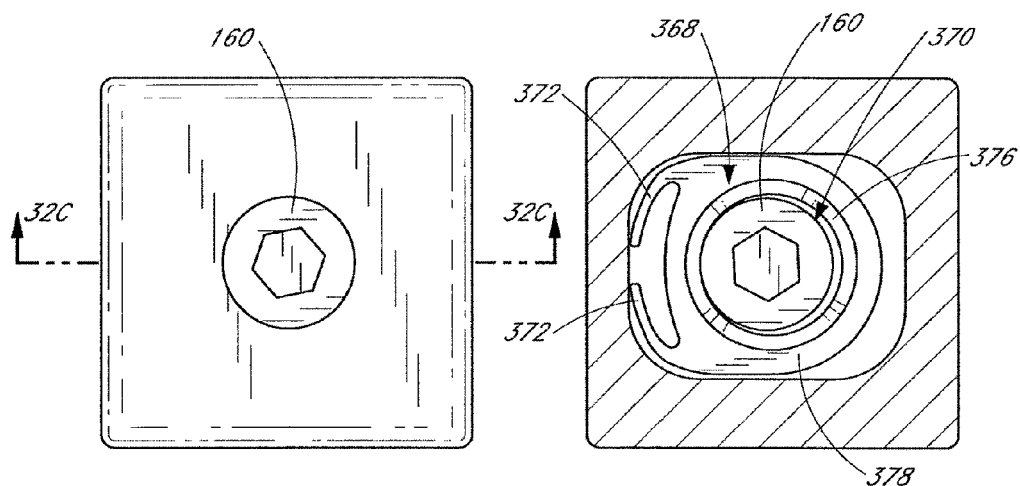
*FIG. 32A*  *FIG. 32B*
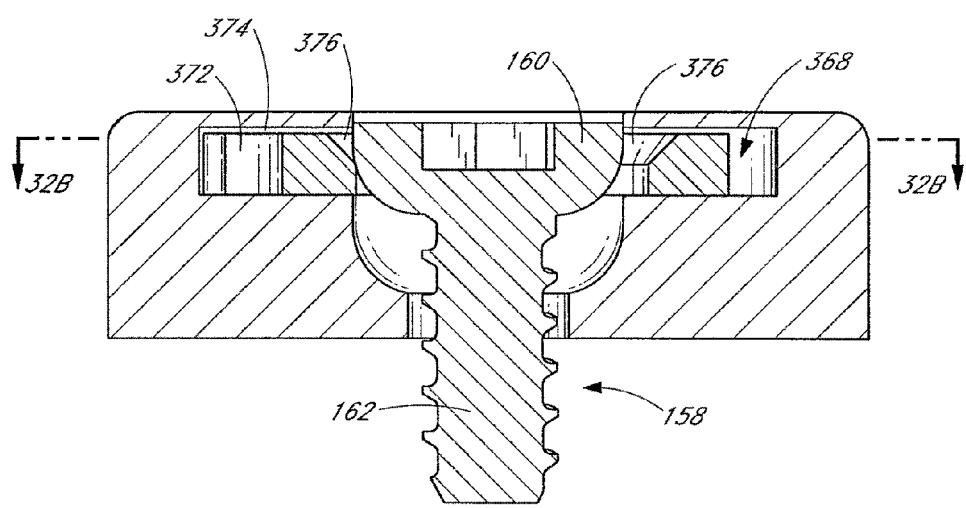
*FIG. 32C*

ORTHOPEDIC EXPANSION FASTENER

CROSS-REFERENCE TO RELATED APPLICATIONS

The present application is a divisional of U.S. application Ser. No. 11/374,658 filed on Mar. 13, 2006, which claims priority under 35 U.S.C. §119(e) to U.S. Provisional Application No. 60/662,747 filed on Mar. 17, 2005 and U.S. Provisional Application No. 60/708,918 filed on Aug. 17, 2005, the disclosures of which are incorporated by reference herein in their entirety.

BACKGROUND OF THE INVENTION

1. Field of the Invention

This invention relates generally to systems for performing spinal fixation. The invention comprises one or more vertebral spacers that feature an attachment system that resists backing out of the screws used to attach the spacers to the vertebrae. The invention may be configured so that multiple adjacent spacers may be used along the vertebral column.

2. Description of the Related Art

Advancing age, as well as injury, can lead to degenerative changes in the bones, discs, joints and ligaments of the spine, producing pain and instability. Under certain circumstances, alleviation of the problems can be provided by performing spinal fusion. Spinal fusion is a surgical technique where two or more vertebrae of the spinal column are fused together to eliminate the motion between the fused vertebrae. Spinal fusion is used to treat conditions where the spine exhibits instability. Spine instability may result from causes such as fracture, scoliosis and spondylolisthesis, where one or more vertebrae move in a forward direction relative to the other vertebrae. Spinal fusion with discectomy is also performed for herniations of the discs. This surgery involves removal of the affected disc and fusion of the adjacent vertebrae. Traditionally, bone grafts have been used to fuse the vertebrae, but various types of vertebral implants have also been used.

The use of bone plate and bone screw fixation systems for treating injuries to bones is well established. In most instances, a bone plate is positioned over and surrounding the bone injury area and secured to the bone. The bone plate is secured to the bone by bone screws or other similar fasteners inserted through holes in the bone plate and into the bone itself. The screws are tightened so that the bone plate holds the bone to be treated in place in order to insure proper healing. Early fixation devices tended to be applicable only to long bone injuries with only limited uses for lower lumbar spinal injuries and disorders. The use of plate/screw fixation systems later expanded, however, to include more uses for spinal injuries, including fusion of vertebrae including fixation devices for treating cervical vertebrae injuries.

Notwithstanding the foregoing, there remains a need for improved methods and devices for treating spinal instability.

SUMMARY OF THE INVENTION

Methods and devices are disclosed for treating the vertebral column. An integrated fixation plate and spacer having a retaining structure within the screw holes of the fixation plate to resist backout of screws attaching the fixation plate to the bone is provided. In some embodiments, a screw hole insert is also provided to resist shear forces acting between the screw and fixation plate. In some embodiments, an integrated fixation plate and spacer system is provided, comprising two or more integrated fixation plate and spacer implants, wherein the fixation plates of each implant has a complementary configuration to allow attachment of the implants at adjacent intervertebral spaces. Alternative fixation systems are also contemplated.

In one embodiment of the invention, an intervertebral stabilization system is provided, comprising a first stabilization plate integrated with a first spacer, wherein the first stabilization plate has an upper portion and a lower portion and a second stabilization plate integrated with a second spacer, wherein the second stabilization plate has an upper portion and a lower portion, wherein the lower portion of the first stabilization plate has a configuration complementary to the configuration of the upper portion of the second stabilization plate. In some embodiments, the configuration of the lower portion of the second stabilization plate is complementary to the configuration of the upper portion of the second stabilization plate. In some embodiments, the lower portion of the second stabilization plate has a relative shape equal to the relative shape of the upper portion of the second stabilization plate rotated 180 degrees. In one embodiment, the upper portion of the first stabilization plate may comprise two attachment holes and the lower portion of the first stabilization plate may comprise one attachment hole. The intervertebral stabilization system may further comprise a third stabilization plate and a third spacer, wherein the configuration of the upper portion of the third stabilization plate is complementary to the configuration of the lower portion of the second stabilization plate. The third stabilization plate may be integrated with the third spacer. The lower portion of the third stabilization plate may have a configuration complementary to the configuration of the upper portion of the third stabilization plate. The lower portion of the third stabilization plate may have a relative shape equal to the relative shape of the upper portion of the third stabilization plate rotated 180 degrees. In another embodiment, the intervertebral stabilization system may also further comprise a fourth stabilization plate and a fourth spacer, wherein the upper portion of the fourth stabilization plate has a configuration complementary to configuration of the lower portion of the third stabilization plate. In this embodiment, the second stabilization plate and third stabilization plate may have the same configuration. The lower portion of the second stabilization plate may have a relative shape equal to the relative shape of the upper portion of the second stabilization plate rotated 180 degrees. In one embodiment, the lower portion of the first stabilization plate has a right-sided complementary shape and the upper portion of the second stabilization plate has a left-sided complementary shape. In another embodiment, the lower portion of the first stabilization plate has a left-sided complementary shape and the upper portion of the second stabilization plate has a right-sided complementary shape. The lower portion of the second stabilization plate may have a right-sided complementary shape. The lower portion of the second stabilization plate may have a left-sided complementary shape. The lower portion of the first stabilization plate may have an inside complementary shape and the upper portion of the second stabilization plate has an outside complementary shape. The lower portion of the first stabilization plate may have an underside complementary shape and the upper portion of the second stabilization plate has a topside complementary shape.

In another embodiment of the invention, an implant for treating the spine is provided, comprising a stabilization plate having an access surface and a bone facing surface, an upper portion and a lower portion, a spacer integrated with the stabilization plate at the bone facing surface, a first attachment lumen between the access surface and the bone facing surface of the stabilization plate, the lumen having a first attachment diameter adjacent to the access surface of the stabilization plate, a lumen surface and a second attachment diameter adjacent to the bone facing surface of the stabilization plate, a retaining channel along the lumen surface, and a third attachment diameter about the retaining channel, wherein the first attachment diameter is greater than the second attachment diameter, a deformable retaining ring at least partially located within the retaining channel, and a first attachment lumen insert having an inner insert diameter and an outer insert diameter. The at least a portion of the spacer may comprise tissue engagement structures. The tissue engagement structures may comprise teeth. The implant may further comprise a bone screw, the bone screw having a screw head and a screw body, wherein the screw head has a head diameter less than the first attachment diameter and greater than the second attachment diameter, or a head diameter less than the first attachment diameter and greater than the inner insert diameter. The implant may further comprise a second attachment lumen between the access surface and the bone facing surface of the stabilization plate, the lumen having a fourth attachment diameter adjacent to the access surface of the stabilization plate, a lumen surface and a fifth attachment diameter adjacent to the bone facing surface of the stabilization plate.

In another embodiment, a method for treating a spine is provided, comprising the steps of providing a first stabilization plate integrated with a first spacer, wherein the first stabilization plate comprises an upper portion, a lower portion and a plurality of attachment holes, at least one attachment hole comprising a retaining structure and an attachment insert, inserting the spacer component into a vertebral space between a first vertebra and a second vertebra, attaching the upper portion of the first stabilization plate to the first vertebra, and attaching the lower portion of the first stabilization plate to the second vertebra.

In one embodiment of the invention, a method for treating a spine is provided comprising the steps of providing an integrated stabilization plate and spacer system, comprising a first integrated stabilization plate and first spacer and a second integrated stabilization plate and a second spacer, each stabilization plate having an upper portion and a lower portion and wherein the lower portion of the first integrated stabilization plate has a complementary shape to the upper portion of the second integrated stabilization plate, inserting the first spacer into a first intervertebral space between a first vertebra and a second vertebra, attaching the upper portion of the first integrated stabilization plate to the first vertebra, attaching the lower portion of the first integrated stabilization plate to the second vertebra, inserting the second spacer into a second intervertebral space between the second vertebra and a third vertebra, wherein the second intervertebral space is next to the first intervertebral space along a vertebral column, attaching the upper portion of the second integrated stabilization plate to the second vertebra; and attaching the lower portion of the second integrated stabilization plate to the third vertebra. In some instances, the integrated stabilization plate and spacer system of the providing step may further comprise a third integrated stabilization plate and a second spacer, wherein the lower portion of the second integrated stabilization plate has a complementary shape to the upper portion of the third integrated stabilization plate. The method for treating a spine may further comprise the steps of inserting the third spacer into a third intervertebral space between the third vertebra and a fourth vertebra, wherein the third intervertebral space is next to the second intervertebral space along the vertebral column, attaching the upper portion of the third integrated stabilization plate to the third vertebra, and attaching the lower portion of the third integrated stabilization plate to the fourth vertebra.

In one embodiment of the invention, an orthopedic implant assembly is provided, comprising a stabilizing element having a trailing surface, a leading surface and at least one lumen, the lumen having a first opening at the trailing surface, a second opening at the leading surface that is smaller than the first opening, and a passageway extending from the first opening to the second opening, a securing element having an elongated body, a head at one end of the body and integral therewith, and a lumen insert member defining a portion of the passageway, having an inner diameter and an outer diameter, and adapted to substantially reduce any force exerted between the stabilizing element and the securing element, wherein the diameter of the head of the securing element is greater than the lesser diameter between the second opening of the lumen and the inner diameter of the insert. The orthopedic implant may further comprise an interbody element integral with the leading surface of the stabilizing element and/or a locking assembly for resisting movement of securing element in at least one direction.

In another embodiment, an implant for treating the spine is provided, comprising: a fixation plate having an access surface and a bone facing surface, an upper portion and a lower portion; a spacer; and a moveable connection between the spacer and the bone facing surface of the fixation plate. The moveable connection may be a hinge joint, a ball and socket joint, or a metal cord attached between the spacer and the bone facing surface of the fixation plate.

In one embodiment, an implant for treating the spine is provided, comprising: a fixation plate having an access surface and a bone facing surface, an upper portion and a lower portion; a spacer connected to the bone facing surface of the fixation plate; and one or more locking plates with an alignment structure to non-frictionally resist rotation of the locking plate when partially attached to the fixation plate by a fastener.

In another embodiment, an implant for treating the spine is provided, comprising: a fixation plate having an access surface and a bone facing surface, an upper portion and a lower portion; a spacer connected to the fixation plate at the bone facing surface; a first attachment lumen between the access surface and the bone facing surface of the stabilization plate, the lumen having a first attachment diameter adjacent to the access surface of the stabilization plate, a lumen surface and a second attachment diameter adjacent to the bone facing surface of the stabilization plate, a retaining channel along the lumen surface, and a third attachment diameter about the retaining channel, wherein the first attachment diameter is greater than the second attachment diameter; and a deformable retaining ring having a retaining segment and a polyaxial segment and an abutting surface therebetween, wherein the retaining segment of the deformable retaining ring is at least partially located within the retaining channel.

In one embodiment, a system for attaching to a structure is provided, comprising: an attachment device having an access surface, an facing surface, a first attachment lumen between the access surface and the facing surface of the attachment device, the first attachment lumen having a first attachment diameter adjacent to the access surface of the attachment device, a first lumen surface and a second attachment diameter adjacent to the facing surface of the attachment device, a first retaining channel along the first lumen surface, and a third attachment diameter about the first retaining channel, wherein the first attachment diameter is greater than the second attachment diameter; and a side-biased blocking structure at least partially within the retaining channel having an uncompressed configuration that protrudes into the first attachment lumen and a compressed configuration that does not protrude into the first attachment lumen. The blocking structure may comprise a sloped surface.

In another embodiment of the invention, a fastener is provided, comprising: a fastener head and fastener shaft, the fastener head comprising a screw lumen, an external groove and one or more openings between the screw lumen and external groove, and an expandable member located at least partially in the external groove and protruding through the one or more openings into the screw lumen. The expandable member may be a ring. The fastener may further comprise a secondary screw configured for the screw lumen.

In one embodiment, an intervertebral stabilization system is provided, comprising a first stabilization plate integrated with a first spacer, wherein the first stabilization plate comprises an upper portion and a lower portion, and a second stabilization plate integrated with a second spacer, wherein the second stabilization plate comprises an upper portion and a lower portion, wherein the lower portion of the first stabilization plate has a configuration complementary to the configuration of the upper portion of the second stabilization plate. The configuration of the lower portion of the second stabilization plate may be complementary to the configuration of the upper portion of the second stabilization plate. The lower portion of the second stabilization plate may have a relative shape equal to the relative shape of the upper portion of the second stabilization plate rotated 180 degrees. The upper portion of the first stabilization plate may comprise two attachment holes. The lower portion of the first stabilization plate may comprise one attachment hole. The intervertebral stabilization system may further comprise a third stabilization plate and a third spacer, wherein the configuration of the upper portion of the third stabilization plate may be complementary to the configuration of the lower portion of the second stabilization plate. The third stabilization plate may be integrated with the third spacer. The lower portion of the third stabilization plate may have a configuration complementary to the configuration of the upper portion of the third stabilization plate. The lower portion of the third stabilization plate may have a relative shape equal to the relative shape of the upper portion of the third stabilization plate rotated 180 degrees. The intervertebral stabilization system may further comprise a fourth stabilization plate and a fourth spacer, wherein the upper portion of the fourth stabilization plate has a configuration complementary to configuration of the lower portion of the third stabilization plate. The second stabilization plate and third stabilization plate may have the same configuration. The lower portion of the second stabilization plate may have a relative shape equal to the relative shape of the upper portion of the second stabilization plate rotated 180 degrees. The lower portion of the first stabilization plate may have a right-sided complementary shape and the upper portion of the second stabilization plate may have a left-sided complementary shape. The lower portion of the first stabilization plate may have a left-sided complementary shape and the upper portion of the second stabilization plate may have a right-sided complementary shape. The lower portion of the second stabilization plate may have a right-sided complementary shape. The lower portion of the second stabilization plate may have a left-sided complementary shape. The lower portion of the first stabilization plate may have an inside complementary shape and the upper portion of the second stabilization plate may have an outside complementary shape. The lower portion of the first stabilization plate may have an underside complementary shape and the upper portion of the second stabilization plate may have a topside complementary shape.

In another embodiment, an orthopedic implant assembly is provided, comprising a stabilizing element having a trailing surface, a leading surface and at least one lumen, the lumen having a first opening at the trailing surface, a second opening at the leading surface that may be smaller than the first opening, and a passageway extending from the first opening to the second opening, a securing element having an elongated body, a head at one end of the body and integral therewith, and a lumen insert member within a portion of the passageway, the lumen insert member comprising an inner diameter and an outer diameter, and adapted to substantially reduce any force exerted between the stabilizing element and the securing element, wherein the diameter of the head of the securing element may be greater than the lesser diameter between the second opening of the lumen and the inner diameter of the insert. The orthopedic implant assembly may further comprise an interbody element integral with the leading surface of the stabilizing element. The orthopedic implant assembly may further comprise a locking assembly for resisting movement of securing element in at least one direction.

In one embodiment, a method for treating a spine is provided, comprising providing an integrated stabilization plate and spacer system, comprising a first integrated stabilization plate and first spacer and a second integrated stabilization plate and a second spacer, wherein each stabilization plate having an upper portion and a lower portion and wherein the lower portion of the first integrated stabilization plate may have a complementary shape to the upper portion of the second integrated stabilization plate, inserting the first spacer into a first intervertebral space between a first vertebra and a second vertebra, attaching the upper portion of the first integrated stabilization plate to the first vertebra, attaching the lower portion of the first integrated stabilization plate to the second vertebra, inserting the second spacer into a second intervertebral space between the second vertebra and a third vertebra, wherein the second intervertebral space may be next to the first intervertebral space along a vertebral column, attaching the upper portion of the second integrated stabilization plate to the second vertebra, and attaching the lower portion of the second integrated stabilization plate to the third vertebra. The integrated stabilization plate and spacer system wherein providing the integrated stabilization plate and spacer system may further comprise a third integrated stabilization plate and a second spacer, wherein the lower portion of the second integrated stabilization plate may have a complementary shape to the upper portion of the third integrated stabilization plate. The method for treating a spine may further comprise inserting the third spacer into a third intervertebral space between the third vertebra and a fourth vertebra, wherein the third intervertebral space may be next to the second intervertebral space along the vertebral column, attaching the upper portion of the third integrated stabilization plate to the third vertebra, and attaching the lower portion of the third integrated stabilization plate to the fourth vertebra.

In one embodiment, an implant for treating the spine is provided, comprising, a stabilization plate comprising an access surface and a bone facing surface, an upper portion and a lower portion, a spacer integral with the stabilization plate at the bone facing surface, a first attachment lumen between the access surface and the bone facing surface of the stabilization plate, the first attachment lumen having a first attachment diameter adjacent to the access surface of the stabilization plate, a lumen surface and a second attachment diameter adjacent to the bone facing surface of the stabilization plate, a retaining channel along the lumen surface, and a third attachment diameter about the retaining channel, wherein the first attachment diameter may be greater than the second attachment diameter, a deformable retaining ring at least partially located within the retaining channel, and a first attachment lumen insert located at least partially in the first attachment lumen and having an inner insert diameter and an outer insert diameter. At least a portion of the spacer may comprise tissue engagement structures. The tissue engagement structures may comprise teeth. The implant may further comprise a bone screw, the bone screw having a screw head and a screw body, wherein the screw head may have a head diameter less than the first attachment diameter and greater than the second attachment diameter. The implant may further comprise a bone screw, the bone screw having a screw head and a screw body, wherein the screw head may have a head diameter less than the first attachment diameter and greater than the inner insert diameter. The outer insert diameter may be greater than the second attachment diameter and the inner insert diameter may be smaller than the second attachment diameter. The second attachment diameter and the third attachment diameter are generally equal. The first attachment lumen insert may be located within the first attachment lumen. The first attachment lumen insert may comprise an inner concave surface. The screw head of the bone screw may comprise an outer convex surface. The outer convex surface of the screw head may be complementary to the inner concave surface of the first attachment lumen insert. The implant may further comprise a second attachment lumen between the access surface and the bone facing surface of the stabilization plate, the second attachment lumen having a fourth attachment diameter adjacent to the access surface of the stabilization plate, a lumen surface and a fifth attachment diameter adjacent to the bone facing surface of the stabilization plate.

In another embodiment, a method for treating a spine is provided, comprising providing a first stabilization plate integral with a first spacer, wherein the first stabilization plate comprises an upper portion, a lower portion and a plurality of attachment holes, wherein at least one attachment hole comprising a retaining structure and an attachment insert, inserting the first spacer into a vertebral space between a first vertebra and a second vertebra, attaching the upper portion of the first stabilization plate to the first vertebra, and attaching the lower portion of the first stabilization plate to the second vertebra. The at least one attachment hole may further comprise a retaining groove and the retaining structure may be a retaining ring positioned in the retaining groove. The attachment insert may comprise a concave surface. The retaining ring may be integral with the attachment insert. Attaching the upper portion of the first stabilization plate to the first vertebra may comprise inserting a bone fastener through one of the plurality of attachment holes located in the upper portion of the first stabilization plate and engaging the first vertebra with the bone fastener. The method may further comprise providing a second stabilization plate integral with a second spacer, wherein the second stabilization plate may comprise an upper portion and a lower portion. The lower portion of the first stabilization plate may have a complementary configuration to the upper portion of the second stabilization plate. The method may further comprise inserting the second spacer into a vertebral space between the second vertebra and a third vertebra.

In one embodiment, an implant for treating the spine is provided, comprising a fixation plate comprising an access surface and a bone facing surface, an upper portion and a lower portion, a spacer connected to the fixation plate at the bone facing surface, a first attachment lumen between the access surface and the bone facing surface of the stabilization plate, the lumen having a first attachment diameter adjacent to the access surface of the stabilization plate, a lumen surface and a second attachment diameter adjacent to the bone facing surface of the stabilization plate, a retaining channel along the lumen surface, and a third attachment diameter about the retaining channel, wherein the first attachment diameter may be greater than the second attachment diameter, a deformable retaining ring having a retaining segment and a polyaxial segment and an abutting surface therebetween, wherein the retaining segment of the deformable retaining ring may be at least partially located within the retaining channel.

In another embodiment, an implant for treating the spine is provided, comprising a fixation plate having an access surface and a bone facing surface, an upper portion and a lower portion, a spacer, and a non-detachable articulation between the spacer and the bone facing surface of the fixation plate. The non-detachable articulation may be a hinge joint. The hinge joint may have a joint axis that does not intersect the fixation plate. The hinge joint may have a joint axis configured to be generally perpendicular to a longitudinal axis of a vertebral column when implanted. The hinge joint may have a joint axis configured to be generally parallel to a longitudinal axis of a vertebral column when implanted. The non-detachable articulation may be a ball and socket joint. The non-detachable articulation may comprise a metal cord attached between the spacer and the bone facing surface of the fixation plate. The non-detachable articulation may be a pivoting articulation.

In one embodiment, an implant for treating the spine is provided, comprising a fixation plate having an access surface and a bone facing surface, an upper portion and a lower portion, a spacer, and a pivoting articulation between the spacer and the bone facing surface of the fixation plate. The pivoting articulation may be a hinge joint. The hinge joint may have a joint axis configured to be generally perpendicular to a longitudinal axis of a vertebral column when implanted. The hinge joint may have a joint axis configured to be generally parallel to a longitudinal axis of a vertebral column when implanted. The pivoting articulation may be a ball and socket joint. The pivoting articulation may comprise a metal cord attached between the spacer and the bone facing surface of the fixation plate. The pivoting articulation may be a detachable articulation.

In another embodiment, an implant for treating the spine is provided, comprising a fixation plate having an access surface and a bone facing surface, an upper portion and a lower portion, a spacer, and a rotatable articulation between the spacer and the fixation plate and comprising an axis of rotation, wherein the axis of rotation of the rotatable articulation does not intersect the fixation plate. The axis of rotation of the rotatable articulation may be generally parallel to the fixation plate. The rotatable articulation may be configured to allow reversible separation of the fixation plate and spacer.

In another embodiment, an implant for treating the spine is provided, comprising a fixation plate comprising an access surface and a bone facing surface, an upper portion, a lower portion, and at least one attachment lumen between the access surface and the bone facing surface, a spacer connected to the bone facing surface of the fixation plate, and a locking plate configured to overlie the at least one attachment lumen and comprising an alignment structure to non-frictionally resist rotation of the locking plate when the locking plate is partially attached to the fixation plate by a fastener. The implant may further comprise two attachment lumens and the locking plate may overlie at least one of the two attachment lumens. The locking plate may overlie both of the two attachment lumens. The fixation plate may further comprise a third attachment lumen. The locking plate may overlie the two attachment lumens and the third attachment lumen. The fixation plate may further comprise a fourth attachment lumen. The locking plate may overlie the two attachment lumens, the third attachment lumen and the fourth attachment lumen. At least a portion of the spacer may comprise tissue engagement structures. The tissue engagement structures may comprise teeth. The spacer may be integral with the bone facing surface of the fixation plate or may be connected to the bone facing surface of the fixation plate by an articulation joint. The articulation joint may be separable or non-separable. The lower portion of the fixation plate may have a configuration complementary to the configuration of the upper portion of the fixation plate. The alignment structure may comprise an elongate member and wherein the fixation plate may further comprise an alignment lumen configured to accept the elongate member. The elongate member and the alignment lumen may be configured to resist rotation of the elongate member when in the alignment lumen. The locking plate may have an X-shaped configuration or an H-shaped configuration. The locking plate may further comprise a second alignment structure and wherein the fixation plate may further comprise a second alignment lumen configured for accepting the second alignment structure. The locking plate may overlie one of the two attachment lumens and the implant may further comprise a second locking plate overlying the other of the two attachment lumens.

In another embodiment, an implant for treating the spine is provided, comprising a flanged intervertebral spacer comprising a spacer body and a flange section, the flange section comprising an access surface and a bone facing surface, an upper portion, a lower portion, four attachment lumens between the access surface and the bone facing surface and two alignment lumens, a locking plate comprising four attachment cover sections and two alignment pins, wherein the four attachment cover sections are configured to cover the four attachment lumens of the flange section and the two alignment pins are configured for insertion into the two alignment lumens of the flange section.

In one embodiment, a system for attaching to a structure is provided, comprising an attachment device having an access surface, a facing surface, a first attachment lumen between the access surface and the facing surface of the attachment device, the first attachment lumen having a first attachment diameter adjacent to the access surface of the attachment device, a first lumen surface and a second attachment diameter adjacent to the facing surface of the attachment device, a first retaining channel along the first lumen surface, and a third attachment diameter about the first retaining channel, wherein the first attachment diameter may be greater than the second attachment diameter, and a side-biased blocking structure at least partially within the retaining channel and comprising an uncompressed configuration that protrudes into the first attachment lumen and a compressed configuration that does not protrude into the first attachment lumen. The blocking structure may comprise a slope surface. The blocking structure may be an arcuate structure. The arcuate structure may be a ring structure. The blocking structure may be a rectangular plate with a through lumen. The through lumen may be a circular through lumen. The attachment structure may be an interbody spacer, a flanged interbody spacer, a fixation plate a vertebral fixation plate, or an anterior cervical fixation plate. The blocking structure may comprise a helical spring member, a leaf spring member, or an elongate bias member. The blocking structure may comprise a second elongate bias member. The elongate bias member may have an arcuate shape.

In one embodiment, a method for treating the spine is provided, comprising providing an orthopedic device comprising a fastener lumen, a securing structure space about the fastener lumen, a securing structure in the fastener lumen and the securing structure space, wherein the securing structure may comprise a bias element and a non-deformable blocking element, inserting a fastener into the fastener lumen, displacing at least a portion of the non-deformable blocking element from the fastener lumen into the securing structure space by compressing the bias element, and passing the head of the fastener past the non-deformable blocking element to allow re-expansion of the bias element.

In another embodiment, a method for treating the spine is provided, comprising providing an orthopedic device comprising a fastener lumen with a longitudinal lumen axis, a securing structure space about the fastener lumen, a securing structure in the fastener lumen and the securing structure space, wherein the securing structure may comprise a biased lumen blocker, inserting a fastener into the fastener lumen, eccentrically displacing the biased lumen blocker with respect to the longitudinal axis of the fastener lumen, and passing the fastener past biased lumen blocker to allow reversion of the biased lumen blocker toward a prior position. The method may further comprise reverting the biased lumen blocker toward a prior position or to a prior position.

In one embodiment, a fastener is provided, comprising a fastener head and fastener shaft, the fastener head comprising a screw lumen, an external groove and one or more openings between the screw lumen and external groove, and an expandable member located at least partially in the external groove and protruding through the one or more openings into the screw lumen. The expandable member may be a ring. The fastener may further comprise a secondary screw configured for the screw lumen.

In one embodiment, an orthopedic fastening system is provided, comprising a fastener comprising a fastener head and a threaded fastener body, wherein the fastener head may comprise a lumen opening, a central internal lumen contiguous with the lumen opening, a side lumen contiguous with the central internal lumen and an expansion member located at least partially within the side lumen and having an expanded configuration and a reduced configuration. The fastener head may further comprise an internal screw and located in the central internal lumen, the internal screw having a proximal position and a distal position. The internal screw in the proximal position may be located about the side lumen and in the distal position may be located distal to the side lumen. The proximal position of the internal screw may displace the expansion member into the expanded configuration. The orthopedic proximal position of the internal screw at least partially displaces the expansion member out of the side lumen. The proximal position of the internal screw allows the expansion member to be in the reduced configuration. The expansion member in the reduced configuration may be partially located in the central internal lumen. The proximal position of the internal screw at least partially displaces the expansion member out of the central internal lumen. The expansion member biased to the reduced configuration. The fastener head may further comprise an expansion groove contiguous with the side lumen and the expansion member may comprise an elongate body positioned about the expansion groove. The elongate body may be an arcuate elongate body. The expansion member may further comprise a radial elongate body located at least partially in the side lumen. The orthopedic fastening system may further comprise an orthopedic device comprising a fastener lumen adapted to retain the fastener. The fastener lumen may comprise a proximal diameter, a middle diameter and a distal diameter, wherein the proximal diameter is smaller than the middle diameter. The distal diameter of the fastener lumen may be smaller than the proximal diameter of the fastener lumen. The fastener lumen may comprises a hole insert. The hole insert may comprise a proximal diameter, a middle diameter and a distal diameter, wherein the proximal diameter is smaller than the middle diameter. The orthopedic device may be an interbody spacer, a flanged interbody spacer, a fixation plate, a vertebral fixation plate, or an anterior cervical fixation plate.

In another embodiment, a method for securing an orthopedic device to a bone is provided, comprising providing an orthopedic device comprising a fastener lumen and a fastener, the fastener comprising a fastener head and a fastener body, the fastener head comprising a lumen opening, a central internal lumen contiguous with the lumen opening, an internal screw located within the central internal lumen, a side lumen contiguous with the central internal lumen and an expansion member located at least partially within the side lumen and the central internal lumen and having an expanded configuration and a reduced configuration, attaching the orthopedic device to a bone in a body, moving the internal screw to a position about the side lumen, partially displacing the expansion member with respect to the side lumen, and changing the expansion member to its expanded configuration. The fastener lumen may comprise a middle diameter and a proximal diameter, where the proximal diameter may be less than the middle diameter. The reduced configuration of the expansion member may have a diameter less than the proximal diameter and the expanded configuration of the expansion member may have a diameter between the proximal diameter and the middle diameter. Attaching the orthopedic device to a bone in a body may comprise inserting the fastener into the fastener lumen, and inserting the fastener into the bone of the body. The orthopedic device may be an interbody spacer. The interbody spacer may be a flanged interbody spacer, a fixation plate, a vertebral fixation plate, or an anterior cervical fixation plate.

In another embodiment, a method for securing a device to an object is provided, comprising providing a device comprising a fastener lumen and a fastener, the fastener comprising a fastener head and a fastener body, the fastener head comprising a lumen opening, a central internal lumen contiguous with the lumen opening, an internal screw located within the central internal lumen, a side lumen contiguous with the central internal lumen and an expansion member located at least partially within the side lumen and the central internal lumen and having an expanded configuration and a reduced configuration, attaching the device to an object, moving the internal screw to a position about the side lumen, partially displacing the expansion member with respect to the side lumen, and changing the expansion member to its expanded configuration. The fastener lumen may comprise a middle diameter and a proximal diameter, where the proximal diameter may be less than the middle diameter. The reduced configuration of the expansion member may have a diameter less than the proximal diameter and the expanded configuration of the expansion member may have a diameter between the proximal diameter and the middle diameter. Attaching the device to the object may comprise inserting the fastener into the fastener lumen, and inserting the fastener into the object.

In one embodiment, an intervertebral stabilization system is provided, comprising a first stabilization plate integrated with a first spacer, wherein the first stabilization plate may comprise an upper portion and a lower portion, and a second stabilization plate integrated with a second spacer, wherein the second stabilization plate may comprise an upper portion and a lower portion, wherein the lower portion of the first stabilization plate may have a configuration complementary to the configuration of the upper portion of the second stabilization plate. The configuration of the lower portion of the second stabilization plate may be complementary to the configuration of the upper portion of the second stabilization plate, or may have a relative shape equal to the relative shape of the upper portion of the second stabilization plate rotated 180 degrees. The upper portion of the first stabilization plate may comprise two attachment holes. The lower portion of the first stabilization plate may comprise one attachment hole. The intervertebral stabilization system may further comprise a third stabilization plate and a third spacer, wherein the configuration of the upper portion of the third stabilization plate may be complementary to the configuration of the lower portion of the second stabilization plate. The third stabilization plate may be integrated with the third spacer. The lower portion of the third stabilization plate may have a configuration complementary to the configuration of the upper portion of the third stabilization plate, or may have a relative shape equal to the relative shape of the upper portion of the third stabilization plate rotated 180 degrees. The intervertebral stabilization system may further comprise a fourth stabilization plate and a fourth spacer, wherein the upper portion of the fourth stabilization plate may have a configuration complementary to configuration of the lower portion of the third stabilization plate. The second stabilization plate and third stabilization plate have the same configuration. The lower portion of the second stabilization plate may have a relative shape equal to the relative shape of the upper portion of the second stabilization plate rotated 180 degrees. The lower portion of the first stabilization plate may have a right-sided complementary shape and the upper portion of the second stabilization plate may have a left-sided complementary shape. The lower portion of the first stabilization plate may have a left-sided complementary shape and the upper portion of the second stabilization plate may have a right-sided complementary shape. The lower portion of the second stabilization plate may have a right-sided complementary shape. The lower portion of the second stabilization plate may have a left-sided complementary shape. The lower portion of the first stabilization plate may have an inside complementary shape and the upper portion of the second stabilization plate may have an outside complementary shape. The lower portion of the first stabilization plate may have an underside complementary shape and the upper portion of the second stabilization plate may have a topside complementary shape.

In another embodiment, an orthopedic implant assembly is provided, comprising a stabilizing element having a trailing surface, a leading surface and at least one lumen, the lumen having a first opening at the trailing surface, a second opening at the leading surface that may be smaller than the first opening, and a passageway extending from the first opening to the second opening, a securing element having an elongated body, a head at one end of the body and integral therewith, and a lumen insert member within a portion of the passageway, the lumen insert member having an inner diameter and an outer diameter, and adapted to substantially reduce any force exerted between the stabilizing element and the securing element, wherein the diameter of the head of the securing element may be greater than the lesser diameter between the second opening of the lumen and the inner diameter of the insert. The orthopedic implant assembly may further comprise an interbody element integral with the leading surface of the stabilizing element. The orthopedic implant assembly may further comprise a locking assembly for resisting movement of securing element in at least one direction.

In another embodiment, a method for treating a spine is provided, comprising providing an integrated stabilization plate and spacer system, the integrated stabilization plate and spacer system comprising a first integrated stabilization plate and first spacer and a second integrated stabilization plate and a second spacer, wherein each stabilization plate has an upper portion and a lower portion and wherein the lower portion of the first integrated stabilization plate has a complementary shape to the upper portion of the second integrated stabilization plate, inserting the first spacer into a first intervertebral space between a first vertebra and a second vertebra, attaching the upper portion of the first integrated stabilization plate to the first vertebra, attaching the lower portion of the first integrated stabilization plate to the second vertebra, inserting the second spacer into a second intervertebral space between the second vertebra and a third vertebra, wherein the second intervertebral space is next to the first intervertebral space along a vertebral column, attaching the upper portion of the second integrated stabilization plate to the second vertebra, and attaching the lower portion of the second integrated stabilization plate to the third vertebra. Providing the integrated stabilization plate and spacer system further may comprise a third integrated stabilization plate and a second spacer, wherein the lower portion of the second integrated stabilization plate may have a complementary shape to the upper portion of the third integrated stabilization plate. The method for treating a spine may further comprise the steps of inserting the third spacer into a third intervertebral space between the third vertebra and a fourth vertebra, wherein the third intervertebral space is next to the second intervertebral space along the vertebral column, attaching the upper portion of the third integrated stabilization plate to the third vertebra, and attaching the lower portion of the third integrated stabilization plate to the fourth vertebra.

In another embodiment, an implant for treating the spine is provided, comprising a stabilization plate comprising an access surface and a bone facing surface, an upper portion and a lower portion, a spacer integral with the stabilization plate at the bone facing surface, a first attachment lumen between the access surface and the bone facing surface of the stabilization plate, the first attachment lumen having a first attachment diameter adjacent to the access surface of the stabilization plate, a lumen surface and a second attachment diameter adjacent to the bone facing surface of the stabilization plate, a retaining channel along the lumen surface, and a third attachment diameter about the retaining channel, wherein the first attachment diameter may be greater than the second attachment diameter, a deformable retaining ring at least partially located within the retaining channel, and a first attachment lumen insert located at least partially in the first attachment lumen and having an inner insert diameter and an outer insert diameter. At least a portion of the spacer may comprise tissue engagement structures. The tissue engagement structures may comprise teeth. The implant for treating the spine may further comprise a bone screw, the bone screw having a screw head and a screw body, wherein the screw head has a head diameter less than the first attachment diameter and greater than the second attachment diameter. The implant for treating the spine may further comprise a bone screw, the bone screw having a screw head and a screw body, wherein the screw head may have a head diameter less than the first attachment diameter and greater than the inner insert diameter. The outer insert diameter may be greater than the second attachment diameter and the inner insert diameter may be smaller than the second attachment diameter. The second attachment diameter and the third attachment diameter may be generally equal. The first attachment lumen insert may be located within the first attachment lumen. The first attachment lumen insert may comprise an inner concave surface. The screw head of the bone screw may comprise an outer convex surface. The outer convex surface of the screw head may be complementary to the inner concave surface of the first attachment lumen insert. The implant for treating the spine may further comprise a second attachment lumen between the access surface and the bone facing surface of the stabilization plate, the lumen having a fourth attachment diameter adjacent to the access surface of the stabilization plate, a lumen surface and a fifth attachment diameter adjacent to the bone facing surface of the stabilization plate.

In another embodiment, a method for treating a spine is provided, comprising providing a first stabilization plate integral with a first spacer, wherein the first stabilization plate may comprise an upper portion, a lower portion and a plurality of attachment holes, wherein at least one attachment hole comprises a retaining structure and an attachment insert, inserting the first spacer into a vertebral space between a first vertebra and a second vertebra, attaching the upper portion of the first stabilization plate to the first vertebra, and attaching the lower portion of the first stabilization plate to the second vertebra. The at least one attachment hole further may comprise a retaining groove and the retaining structure may be a retaining ring positioned in the retaining groove. The attachment insert may comprise a concave surface. The retaining ring may be integral with the attachment insert. Attaching the upper portion of the first stabilization plate to the first vertebra may comprise inserting a bone fastener through one of the plurality of attachment holes located in the upper portion of the first stabilization plate and engaging the first vertebra with the bone fastener. The method for treating a spine may further comprise providing a second stabilization plate integral with a second spacer, wherein the second stabilization plate may comprise an upper portion and a lower portion. The lower portion of the first stabilization plate may have a complementary configuration to the upper portion of the second stabilization plate. The method for treating a spine may further comprise inserting the second spacer into a vertebral space between the second vertebra and a third vertebra.

In another embodiment, an implant for treating the spine is provided, comprising a fixation plate comprising an access surface and a bone facing surface, an upper portion and a lower portion, a spacer connected to the fixation plate at the bone facing surface, a first attachment lumen between the access surface and the bone facing surface of the stabilization plate, the lumen having a first attachment diameter adjacent to the access surface of the stabilization plate, a lumen surface and a second attachment diameter adjacent to the bone facing surface of the stabilization plate, a retaining channel along the lumen surface, and a third attachment diameter about the retaining channel, wherein the first attachment diameter is greater than the second attachment diameter, a deformable retaining ring having a retaining segment and a polyaxial segment and an abutting surface therebetween, wherein the retaining segment of the deformable retaining ring is at least partially located within the retaining channel.

In another embodiment, an implant for treating the spine is provided, comprising a fixation plate having an access surface and a bone facing surface, an upper portion and a lower portion, a spacer, and a non-detachable articulation between the spacer and the bone facing surface of the fixation plate. The non-detachable articulation may be a hinge joint. The hinge joint may have a joint axis that does not intersect the fixation plate. The hinge joint may have a joint axis configured to be generally perpendicular to a longitudinal axis of a vertebral column when implanted. The hinge joint may have a joint axis configured to be generally parallel to a longitudinal axis of a vertebral column when implanted. The non-detachable articulation may be a ball and socket joint. The non-detachable articulation may comprise a metal cord attached between the spacer and the bone facing surface of the fixation plate. The non-detachable articulation may be a pivoting articulation.

In another embodiment, an implant for treating the spine is provided, comprising a fixation plate having an access surface and a bone facing surface, an upper portion and a lower portion, a spacer, and a pivoting articulation between the spacer and the bone facing surface of the fixation plate. The pivoting articulation may be a hinge joint. The hinge joint may have a joint axis configured to be generally perpendicular to a longitudinal axis of a vertebral column when implanted. The hinge joint may have a joint axis configured to be generally parallel to a longitudinal axis of a vertebral column when implanted. The pivoting articulation may be a ball and socket joint. The pivoting articulation may comprise a metal cord attached between the spacer and the bone facing surface of the fixation plate. The pivoting articulation may be a detachable articulation.

In another embodiment, an implant for treating the spine is provided, comprising a fixation plate having an access surface and a bone facing surface, an upper portion and a lower portion, a spacer, and a rotatable articulation between the spacer and the fixation plate and comprising an axis of rotation, wherein the axis of rotation of the rotatable articulation does not intersect the fixation plate. The axis of rotation of the rotatable articulation may be generally parallel to the fixation plate. The rotatable articulation may be configured to allow reversible separation of the fixation plate and spacer.

In one embodiment, an implant for treating the spine is provided, comprising a fixation plate comprising an access surface and a bone facing surface, an upper portion, a lower portion, and at least one attachment lumen between the access surface and the bone facing surface, a spacer connected to the bone facing surface of the fixation plate, and a locking plate configured to overlie the at least one attachment lumen and comprising an alignment structure to non-frictionally resist rotation of the locking plate when the locking plate may be partially attached to the fixation plate by a fastener. The fixation plate further may comprise two attachment lumens and the locking plate overlies at least one of the two attachment lumens. The locking plate may overlie both of the two attachment lumens. The fixation plate further may comprise a third attachment lumen. The locking plate may overlie the two attachment lumens and the third attachment lumen. The fixation plate further may comprise a fourth attachment lumen. The locking plate may overlie the two attachment lumens, the third attachment lumen and the fourth attachment lumen. At least a portion of the spacer may comprise tissue engagement structures. The tissue engagement structures may comprise teeth. The spacer may be integral with the bone facing surface of the fixation plate. The spacer may be connected to the bone facing surface of the fixation plate by an articulation joint. The articulation joint may be separable or non-separable. The lower portion of the fixation plate may have a configuration complementary to the configuration of the upper portion of the fixation plate. The alignment structure may comprise an elongate member and wherein the fixation plate further may comprise an alignment lumen configured to accept the elongate member. The elongate member and the alignment lumen may be configured to resist rotation of the elongate member when in the alignment lumen. The locking plate may have an X-shaped configuration. The locking plate may have an H-shaped configuration. The locking plate further may comprise a second alignment structure and wherein the fixation plate further may comprise a second alignment lumen configured for accepting the second alignment structure. The locking plate may overlie one of the two attachment lumens and the implant further may comprise a second locking plate overlying the other of the two attachment lumens.

In one embodiment, an implant for treating the spine is provided, comprising a flanged intervertebral spacer comprising a spacer body and a flange section, the flange section comprising an access surface and a bone facing surface, an upper portion, a lower portion, four attachment lumens between the access surface and the bone facing surface and two alignment lumens, a locking plate comprising four attachment cover sections and two alignment pins, wherein the four attachment cover sections are configured to cover the four attachment lumens of the flange section and the two alignment pins are configured for insertion into the two alignment lumens of the flange section.

In another embodiment, a system for attaching to a structure is provided, comprising an attachment device having an access surface, a facing surface, a first attachment lumen between the access surface and the facing surface of the attachment device, the first attachment lumen having a first attachment diameter adjacent to the access surface of the attachment device, a first lumen surface and a second attachment diameter adjacent to the facing surface of the attachment device, a first retaining channel along the first lumen surface, and a third attachment diameter about the first retaining channel, wherein the first attachment diameter may be greater than the second attachment diameter, and a side-biased blocking structure at least partially within the retaining channel having an uncompressed configuration that protrudes into the first attachment lumen and a compressed configuration that does not protrude into the first attachment lumen. The blocking structure may comprise a slope surface. The blocking structure may be an arcuate structure. The arcuate structure may be a ring structure. The blocking structure may be a rectangular plate with a through lumen. The through lumen may be a circular through lumen. The attachment structure may be an interbody spacer. The interbody spacer may be a flanged interbody spacer. The attachment structure may be a fixation plate. The attachment structure may be a vertebral fixation plate. The vertebral fixation plate may be an anterior cervical fixation plate. The blocking structure may comprise a helical spring member. The blocking structure may comprise a leaf spring member. The blocking structure may comprise an elongate bias member. The blocking structure may comprise a second elongate bias member. The elongate bias member may have an arcuate shape.

In one embodiment, a method for treating the spine is provided, comprising providing an orthopedic device comprising a fastener lumen, a securing structure space about the fastener lumen, a securing structure in the fastener lumen and the securing structure space, wherein the securing structure is a bias element and a non-deformable blocking element, inserting a fastener into the fastener lumen, displacing at least a portion of the non-deformable blocking element from the fastener lumen into the securing structure space by compressing the bias element, and passing the head of the fastener past the non-deformable blocking element to allow re-expansion of the bias element.

In another embodiment, a method for treating the spine is provided, comprising providing an orthopedic device comprising a fastener lumen with a longitudinal lumen axis, a securing structure space about the fastener lumen, a securing structure in the fastener lumen and the securing structure space, wherein the securing structure may comprise a biased lumen blocker, inserting a fastener into the fastener lumen, eccentrically displacing the biased lumen blocker with respect to the longitudinal axis of the fastener lumen, and passing the fastener past biased lumen blocker to allow reversion of the biased lumen blocker toward a prior position. The method for treating the spine may further comprise reverting the biased lumen blocker toward a prior position. The method for treating the spine may further comprise reverting the biased lumen blocker to a prior position.

In one embodiment, a fastener is provided, comprising a fastener head and fastener shaft, the fastener head comprising a screw lumen, an external groove and one or more openings between the screw lumen and external groove, and an expandable member located at least partially in the external groove and protruding through the one or more openings into the screw lumen. The expandable member may be a ring. The fastener may further comprise a secondary screw configured for the screw lumen.

In another embodiment, an orthopedic fastening system is provided, comprising a fastener comprising a fastener head and a threaded fastener body, wherein the fastener head may comprise a lumen opening, a central internal lumen contiguous with the lumen opening, a side lumen contiguous with the central internal lumen and an expansion member located at least partially within the side lumen and having an expanded configuration and a reduced configuration. The fastener head further may comprise an internal screw and located in the central internal lumen, the internal screw having a proximal position and a distal position. The internal screw in the proximal position may be located about the side lumen and in the distal position may be located distal to the side lumen. The proximal position of the internal screw may displace the expansion member into the expanded configuration. The proximal position of the internal screw may at least partially displace the expansion member out of the side lumen. The proximal position of the internal screw may allow the expansion member to be in the reduced configuration. The expansion member in the reduced configuration may be partially located in the central internal lumen. The proximal position of the internal screw at least partially displaces the expansion member out of the central internal lumen. The expansion member may be biased to the reduced configuration. The fastener head further may comprise an expansion groove contiguous with the side lumen and the expansion member may comprise an elongate body positioned about the expansion groove. The elongate body may be an arcuate elongate body. The expansion member further may comprise a radial elongate body located at least partially in the side lumen. The orthopedic fastening system may further comprise an orthopedic device comprising a fastener lumen adapted to retain the fastener. The fastener lumen may comprise a proximal diameter, a middle diameter and a distal diameter, wherein the proximal diameter may be smaller than the middle diameter. The distal diameter of the fastener lumen may be smaller than the proximal diameter of the fastener lumen. The fastener lumen may comprise a hole insert. The hole insert may comprise a proximal diameter, a middle diameter and a distal diameter, wherein the proximal diameter may be smaller than the middle diameter. The orthopedic device may be an interbody spacer. The interbody spacer may be a flanged interbody spacer. The orthopedic device may be a fixation plate. The orthopedic device may be a vertebral fixation plate. The vertebral fixation plate may be an anterior cervical fixation plate.

In another embodiment, a method for securing an orthopedic device to a bone is provided, comprising providing an orthopedic device comprising a fastener lumen and a fastener, the fastener comprising a fastener head and a fastener body, the fastener head comprising a lumen opening, a central internal lumen contiguous with the lumen opening, an internal screw located within the central internal lumen, a side lumen contiguous with the central internal lumen and an expansion member located at least partially within the side lumen and the central internal lumen and having an expanded configuration and a reduced configuration, attaching the orthopedic device to a bone in a body, moving the internal screw to a position about the side lumen, partially displacing the expansion member with respect to the side lumen, and changing the expansion member to its expanded configuration. The fastener lumen may comprise a middle diameter and a proximal diameter, where the proximal diameter may be less than the middle diameter. The reduced configuration of the expansion member may have a diameter less than the proximal diameter and the expanded configuration of the expansion member may have a diameter between the proximal diameter and the middle diameter. Attaching the orthopedic device to a bone in a body may comprise inserting the fastener into the fastener lumen, and inserting the fastener into the bone of the body. The orthopedic device may be an interbody spacer. The interbody spacer may be a flanged interbody spacer. The orthopedic device may be a fixation plate. The orthopedic device may be a vertebral fixation plate. The vertebral fixation plate may be an anterior cervical fixation plate.

In another embodiment, a method for securing an device to an object is provided, comprising providing a device comprising a fastener lumen and a fastener, the fastener comprising a fastener head and a fastener body, the fastener head comprising a lumen opening, a central internal lumen contiguous with the lumen opening, an internal screw located within the central internal lumen, a side lumen contiguous with the central internal lumen and an expansion member located at least partially within the side lumen and the central internal lumen and having an expanded configuration and a reduced configuration, attaching the device to an object, moving the internal screw to a position about the side lumen, partially displacing the expansion member with respect to the side lumen, and changing the expansion member to its expanded configuration. The fastener lumen may comprise a middle diameter and a proximal diameter, where the proximal diameter may be less than the middle diameter. The reduced configuration of the expansion member may have a diameter less than the proximal diameter and the expanded configuration of the expansion member may have a diameter between the proximal diameter and the middle diameter. Attaching the device to the object may comprise inserting the fastener into the fastener lumen, and inserting the fastener into the object.

The above embodiments and methods of use are explained in more detail below.

BRIEF DESCRIPTION OF THE DRAWINGS

The structure and method of using the invention will be better understood with the following detailed description of embodiments of the invention, along with the accompanying illustrations, in which:

FIGS. 25A and 25B represent frontal and lateral views of one embodiment comprising a complementary overlapping spacer system.

FIG. 32A is a superior elevational view of a fastener head positioned within a fastener lumen whereby the fastener has displaced the fastener retaining body into the compressed position. FIGS. 32B and 32C are superior side cross-sectional views of fastener head and fastener retaining body from FIG. 32A.

DETAILED DESCRIPTION OF THE PREFERRED EMBODIMENT

Figure 1:
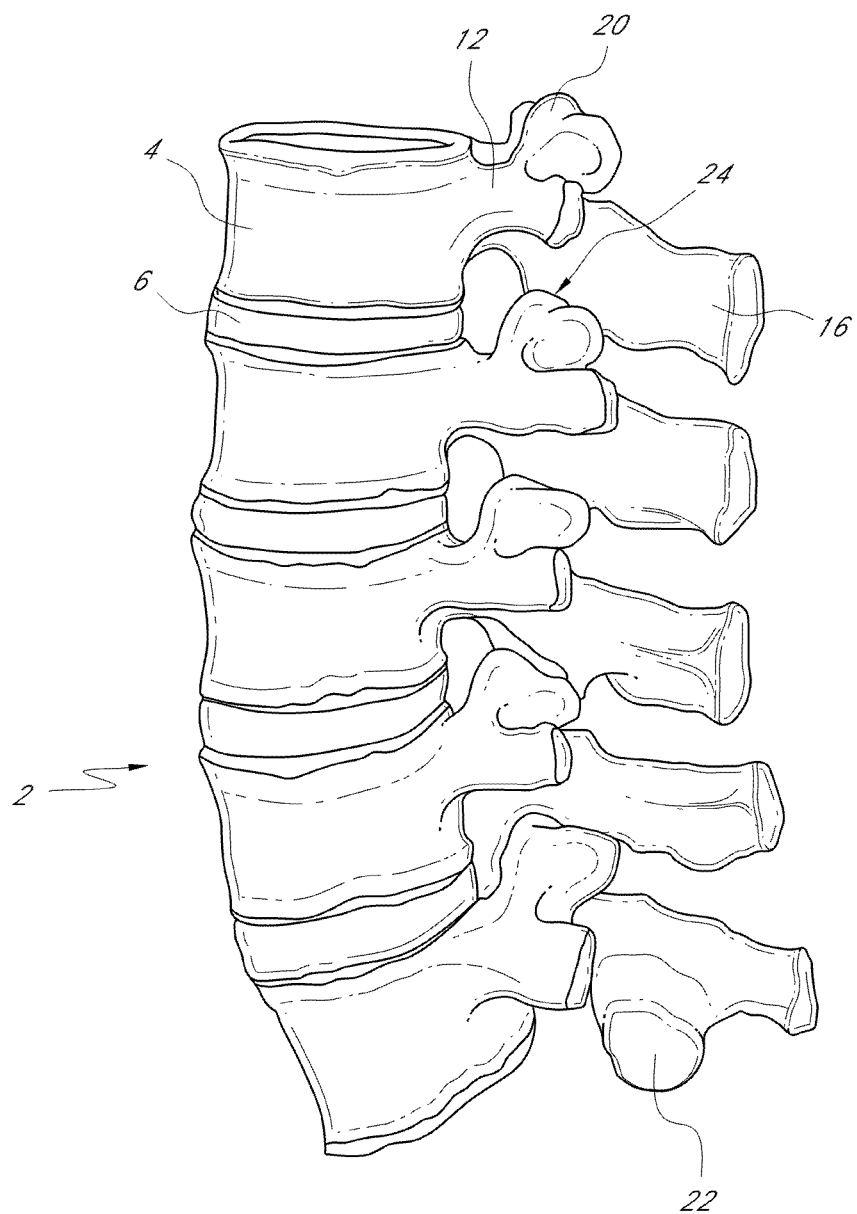
FIG. 1 is a lateral elevational view of a portion of the vertebral column.

Advancing age, as well as injury, can lead to degeneration in the bones, discs, joints, and ligaments of the spine producing pain from nerve root compression. Under certain circumstances, alleviation of pain can be provided by performing a spinal fusion. Spinal fusion is a procedure that involves joining two or more adjacent vertebrae so that they no longer are able to move relative to each other.

In existing spinal fusion implants there have also been problems with loosening and backing out of screws into the patient's throat area. Backout is the exhibited tendency of bone screws, which affix the bone plate to the bone(s), to loosen with respect to both the plate and bone, resulting in poor fixation, fusion and ultimately, healing. Essentially, this loosening of the bone screw causes the screw to work itself out of the bone into which it is implanted. This results in the bone plate being poorly fixed in place thus becoming devoid of its fixation capabilities. Usually, backout is caused by the chronic stress of bodily movement. While such loosening can be benign if limited in scope, it may lead to complications such as complete failure of the fixation device or incomplete bone fusion. Backout is particularly prevalent in areas of high bodily stress and movement, such as the spine.

To alleviate backout and its associated problems, current systems utilize secondary locking screws, locking collars or other secondary locking devices that hold the bone screws in place after deployment within the bone. In most systems, the bone screw is affixed into the bone through an opening in a bone plate. A locking device is then inserted into the bone screw. The locking device engages the head of the bone screw and is tightened which results in the bone screw being fixed in place within the bone, thus preventing backout.

While a locking screw or collar can alleviate backout, successful use of such locking device systems in the anterior cervical spine is particularly difficult because of anatomic constraints. Systems using multiple types of screws or collars to hold the bone screw in place are difficult to deploy within the confines of a small operating area available at the cervical spine. Furthermore, due to the small operating area, the surgeon implanting the device has great difficulty determining if the device is properly deployed. Any instrumentation implanted in the region must be minimally intrusive, yet have adequate strength to withstand the biomechanical loads to which it will be subjected. Thus, while current systems can help reduce instances of backout, their complex nature makes proper deployment very difficult and increases the chance of surgical error.

There is a need for an implant having a locking mechanism that can be easily and reliably locked in place to prevent the loosening of and backing out of the bone screws used to attach the implant to the vertebrae in the anterior aspect of the cervical, thoracic, and lumbar spine.

There is also a need for implants that can be implanted along a series of adjacent vertebrae. Implants adapted for use in the lumbar spine and the thoracic spine become much less usable in the cervical spine because of differences in anatomy. In the lumbar spine, the disc spaces are about 25% as tall as the vertebral bodies (i.e., the vertebral bodies are generally four times taller than the intervening disc space). In the cervical spine, the disc space can be 50% of the height of the vertebral bodies. The disc spaces in the cervical spine are generally not greater than 7 or 8 mm tall in most people.

Attachment of one fixation plate between two vertebrae often prevents the attachment of additional fixation plates between one of two vertebrae and an adjacent vertebra. This is especially true in the cervical spine region. The attachment of one fixation plate will reduce the surface area available to attach another fixation plate due to the small size of the cervical vertebrae and the minimum size required for each fixation plate. Because of this limitation in existing spinal fixation devices, treatment of spinal disorders may be suboptimal because disease in adjacent vertebrae cannot be treated adequately.

A. Anatomy of the Spine

Figure 2A:
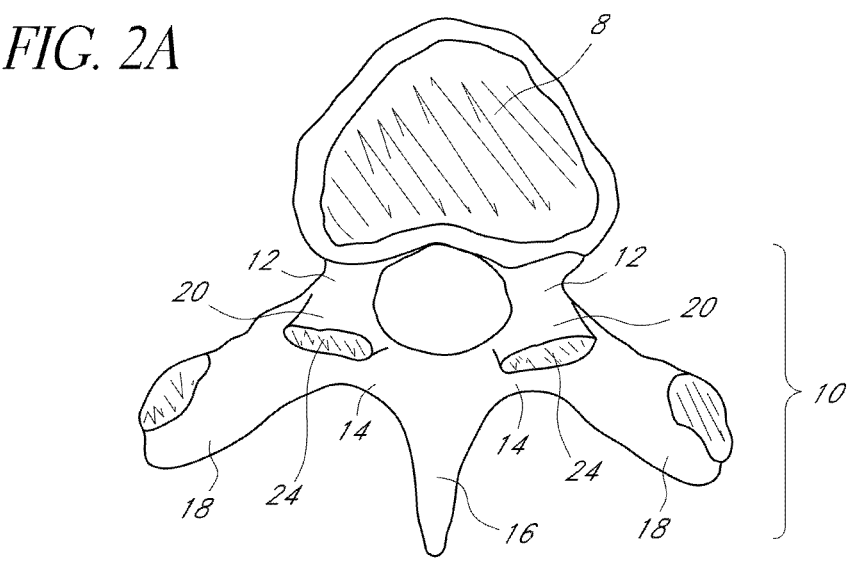
FIGS. 2A and 2B are superior and lateral elevational views of a thoracic vertebra.
Figure 2B:
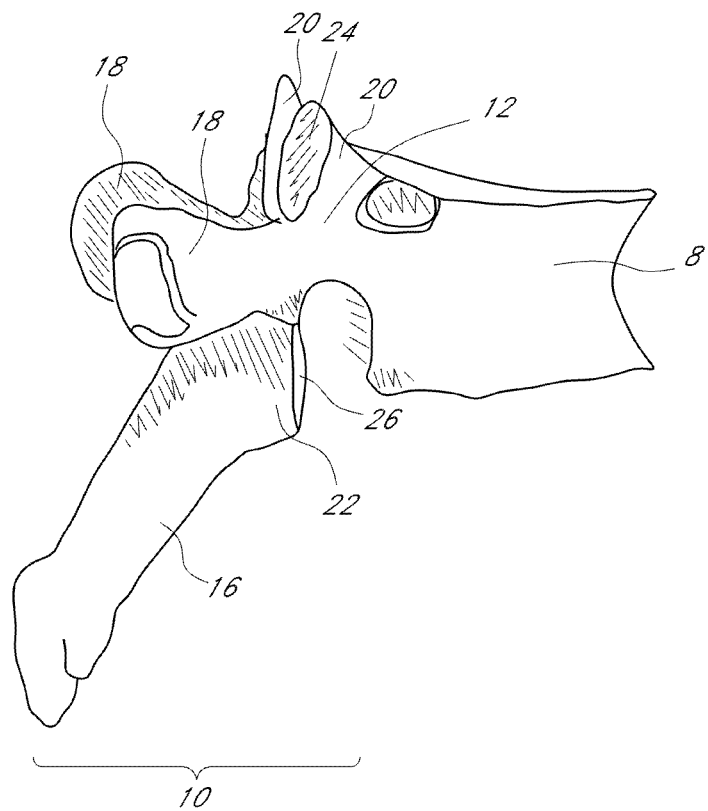

As shown in FIG. 1, the vertebral column 2 comprises a series of alternating vertebrae 4 and fibrous discs 6 that provide axial support and movement to the upper portions of the body. The vertebral column 2 typically comprises thirty-three vertebrae 4, with seven cervical (C1-C7), twelve thoracic (T1-T12), five lumbar (L1-15), five fused sacral (S1-S5) and four fused coccygeal vertebrae. FIGS. 2A and 2B depict a typical thoracic vertebra. Each vertebra includes an anterior body 8 with a posterior arch 10. The posterior arch 10 comprises two pedicles 12 and two laminae 14 that join posteriorly to form a spinous process 16. Projecting from each side of the posterior arch 10 is a transverse 18, superior 20 and inferior articular process 22. The facets 24, 26 of the superior 20 and inferior articular processes 22 form facet joints 28 with the articular processes of the adjacent vertebrae.

Figure 3:
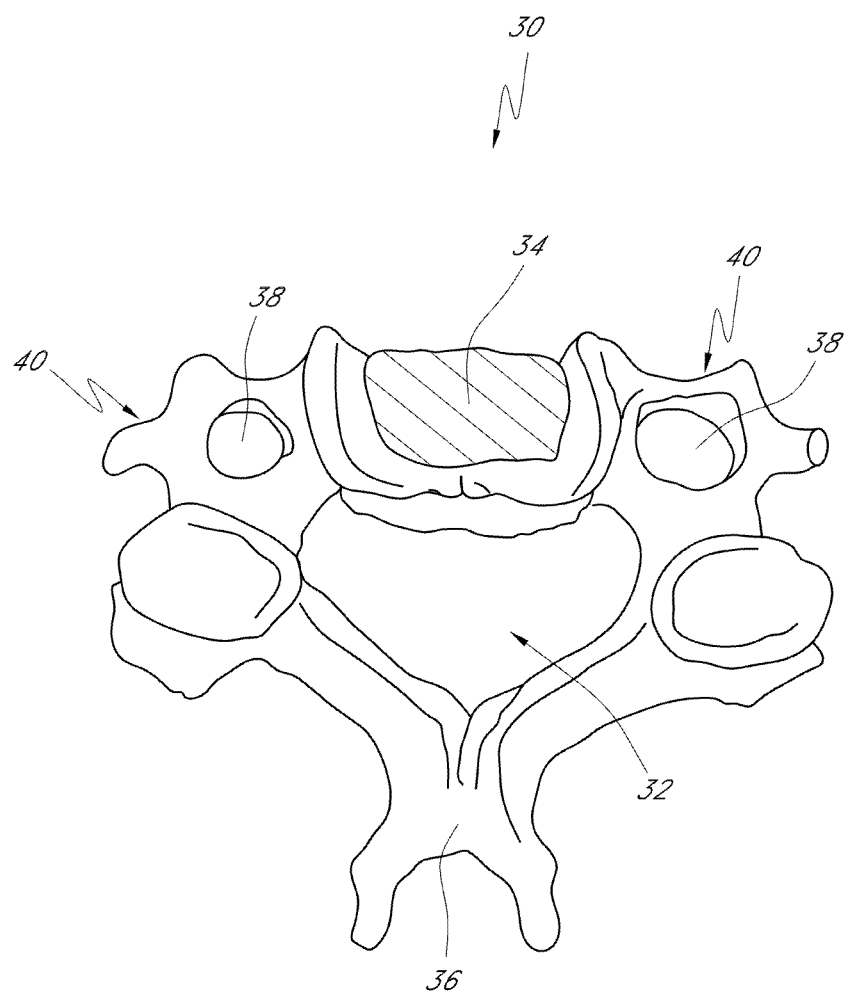
FIG. 3 illustrates a superior elevational view of a cervical vertebra.

The typical cervical vertebrae 30, shown in FIG. 3, differ from the other vertebrae with relatively larger spinal canals 32, oval shaped vertebral bodies 34, bifid spinous processes 36 and foramina 38 in their transverse processes 40. These foramina transversaria 38 contain the vertebral artery and vein. The first and second cervical vertebrae also further differentiated from the other vertebrae. The first cervical vertebra lacks a vertebral body and instead contains an anterior tubercle. Its superior articular facets articulate with the occipital condyles of the skull and are oriented in a roughly parasagittal plane. The cranium is able to slide forward and backwards on this vertebra. The second cervical vertebra contains an odontoid process, or dens, which projects superiorly from its body. It articulates with the anterior tubercle of the atlas, forming a pivot joint. Side to side movements of the head occur at this joint. The seventh cervical vertebra is sometimes considered atypical since it lacks a bifid spinous process.

Figure 4:
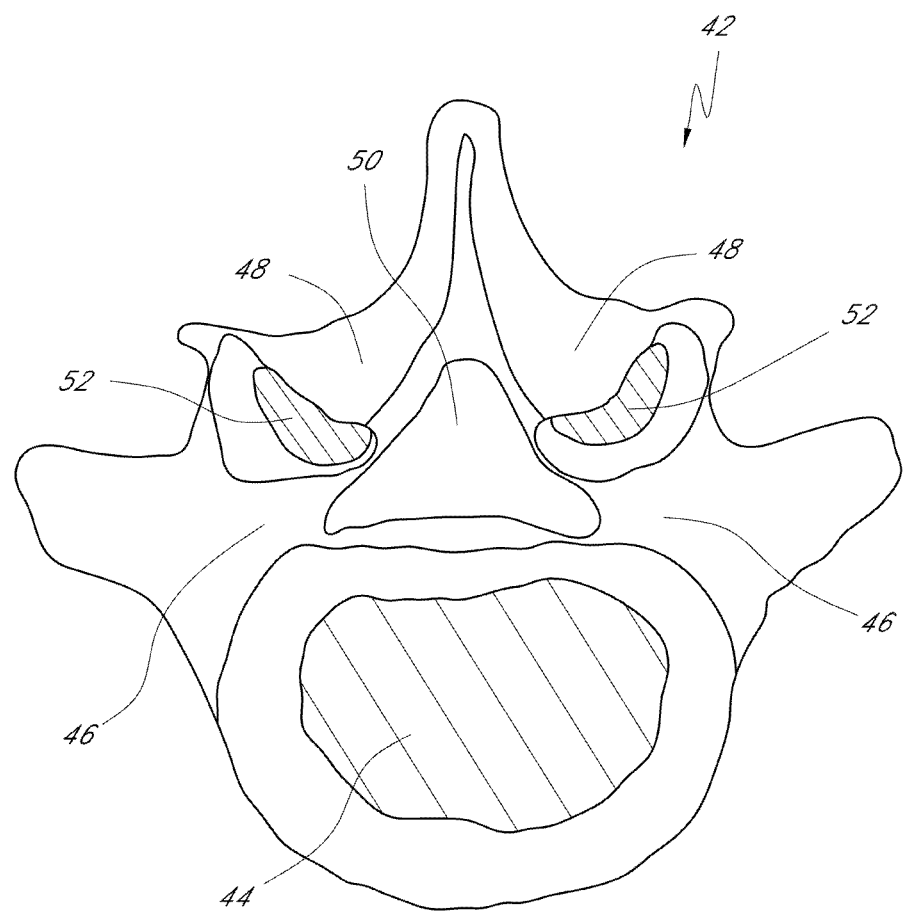
FIG. 4 represents a superior elevational view of a lumbar vertebra.

Referring to FIG. 4, the typical lumbar vertebrae 42 is distinguishable from the other vertebrae by the absence of foramina transversaria and the absence of facets on the surface of the vertebral body 44. The lumbar vertebral bodies 44 are larger than the thoracic vertebral bodies and have thicker pedicles 46 and laminae 48 projecting posteriorly. The vertebral foramen 50 is triangular in shape and larger than the foramina in the thoracic spine but smaller than the foramina in the cervical spine. The superior 52 and inferior articular processes (not shown) project superiorly and inferiorly from the pedicles, respectively.

B. Flanged Spacer

Figure 5A:
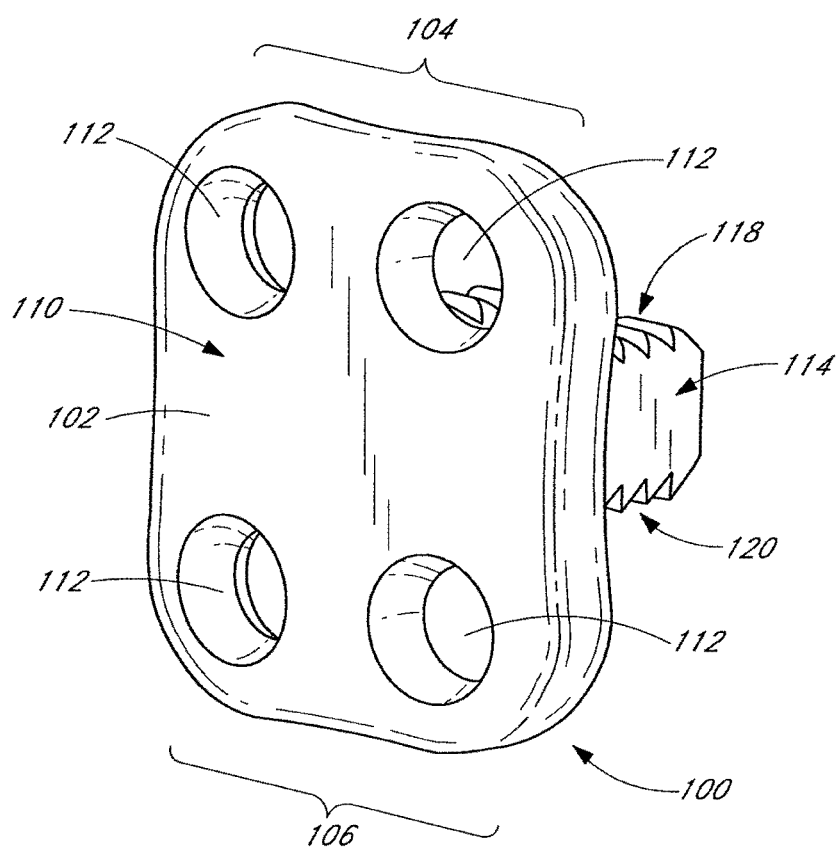
FIGS. 5A through 5C are perspective, superior and lateral elevational views of one embodiment of an integrated fixation plate and spacer.
Figure 5B:
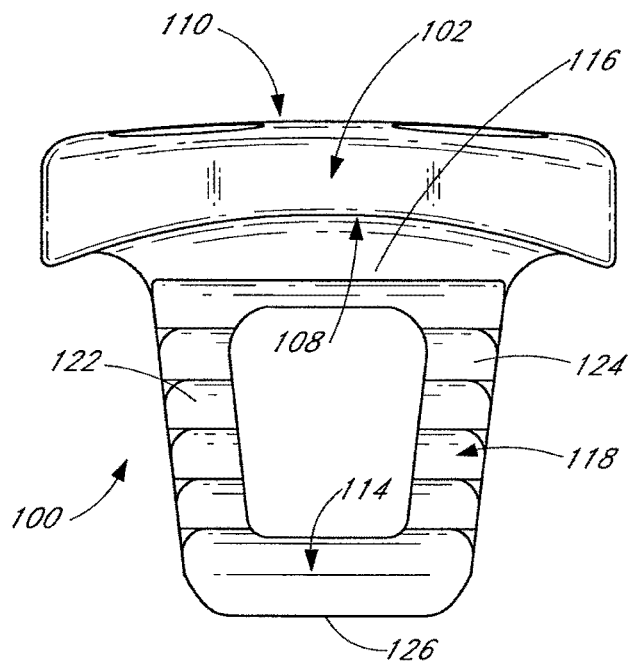
Figure 5C:
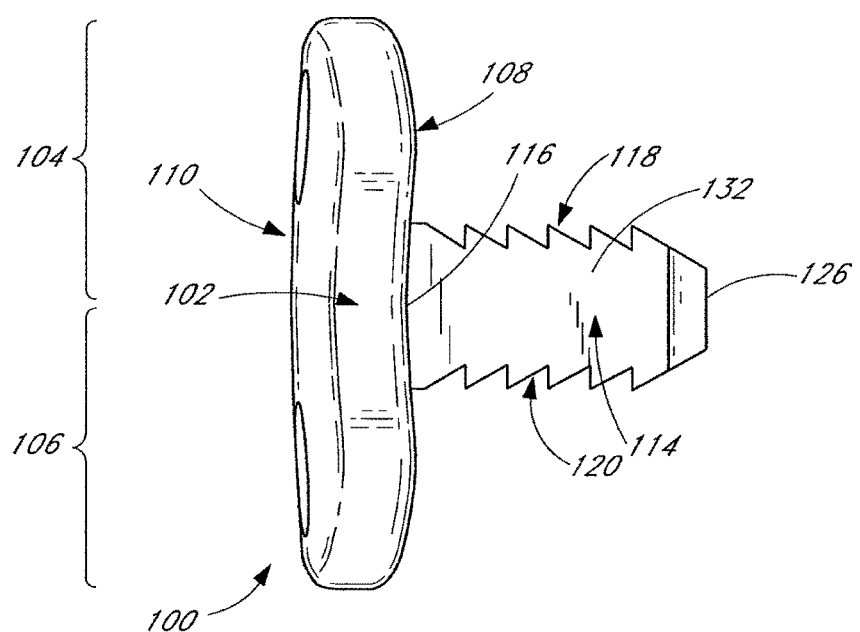

In one embodiment of the invention, an interbody vertebral implant 100 is provided. As shown in FIGS. 5A through 5C, in one embodiment, the implant 100 comprises a stabilization or fixation plate 102 having an upper portion 104 and a lower portion 106, and a bone facing surface 108 and an access surface 110. In use, typically the bone facing surface 108 will actually contact the vertebral bone surface, but in other embodiments, other structures or components may lie in between the bone facing surface 108 and the bone surface of the vertebra. Each upper portion 104 and lower portion 106 has one or more spaces or holes 112 oriented between the bone facing surface 108 and the access surface 110 that are configured to accept screws and/or other attachment devices for anchoring the implant 100 to the vertebral bone. One or more spacers or spacing structures 114 are located on the bone facing surface 108 of the fixation plate 102. The spacers 114 are typically integrated with the fixation plate 102 about the bone facing surface 108.

1. Spacer Component

The spacer may comprise any structure configured to maintain a separation and resist compression between two adjacent vertebral bodies. The spacer may have any of a variety of overall shapes, including but not limited to a rectangular box, a trapezoidal box, H-shaped, O-shaped, V-shaped, with or without one or more lumens within the spacing structure. As shown in FIGS. 5B and 5C, the spacer 114 has a base 116, a superior surface 118 and an inferior surface 120, and side surfaces 122, 124, and a posterior surface 126. Each surface 118, 120, 122, 124, 126 need not be flat, and may be curved or undulating or any combination thereof. The upper and lower surfaces 118, 120 are configured for facing the superior and inferior vertebral bodies 8 or 34 adjacent to an implantation site. The relative configuration of the upper surface 118 and lower surface 120 may vary, depending upon the relative position desired between the two adjacent vertebrae, the anatomical shape of the vertebrae, ease of insertion of the implant and other factors. For example, if a neutral vertical alignment is desired between two vertebrae, the upper and lower surfaces 118, 120 may have generally parallel planar orientations. If a non-neutral alignment is desired, for instance to maintain a natural spinal curvature in the cervical region, the upper and lower surfaces 118, 120 may have a wedge-like relationship to allow fixation of the vertebrae in the desired non-neutral position. A non-neutral alignment with respect to the anterior-posterior direction may also be used to compensate for excessive lordosis or kyphosis in other portions of the vertebral column. The height of the spacing structure 116 at any section between the upper and lower surfaces 118, 120 may be further configured to accommodate degenerative changes or anatomical anomalies to provide fixation in the desired relative position. Likewise, the side surfaces 122, 124 of the spacing structure 114 may be generally parallel or skewed. In one embodiment, the side surfaces 122, 124 of the implant 100 taper with increasing distance from the base 116 of the implant 100. A tapered spacing structure may facilitate insertion of the implant 100 into the intervertebral space. In other embodiments, the one or more side surfaces may flare distally or have both tapering and flaring portions.

Figure 6:
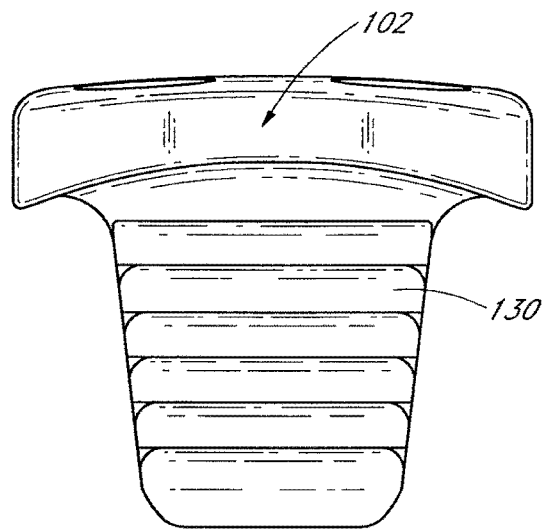
FIG. 6 is a superior elevational view of another embodiment of an integrated fixation plate and spacer.
Figure 7:
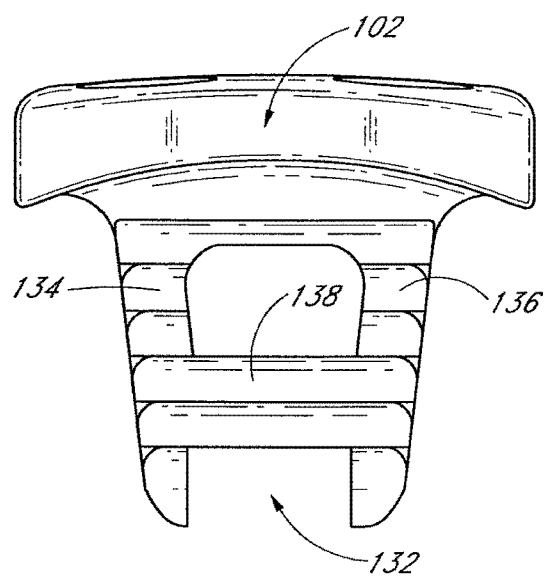
FIG. 7 is a superior elevational view of another embodiment of an integrated fixation plate and spacer.

The device depicted in FIGS. 5B and 5C is one embodiment of the invention comprising a closed-shaped spacer 114 with a lumen 128 between the superior and inferior surfaces 118, 120. The side surfaces 122, 124 may have a slight taper along the posterior direction. FIG. 6 depicts one embodiment of the invention with a block spacer 130 that lacks a spacer lumen. FIG. 7 depicts another embodiment comprising an H-shaped spacer 132 with two protruding members 134, 136 and one bridge member 138 between the two protruding members 134, 136. The bridge member 138 may be oriented in any of a variety of positions between the two protruding members 134, 136. The two protruding members 134, 136 need not have a similar or symmetrical shape. Some embodiments of the invention may have more than two protruding members 134, 136 and/or one or more bridge members 138.

Figure 8A:
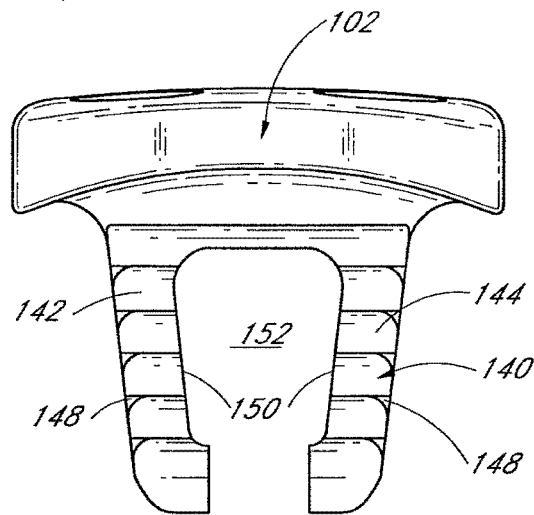
FIGS. 8A and 8B illustrate superior and lateral elevational views of another embodiment of an integrated fixation plate and spacer.
Figure 8B:
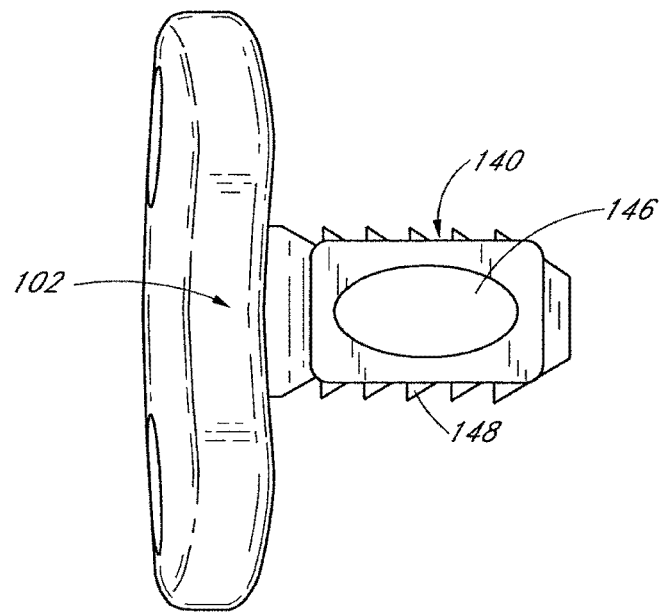

FIGS. 8A and 8B illustrate another embodiment of the invention comprising a spacer 140 with two posterior members 142, 144 where each posterior member 142, 144 has a window or hole 146 between the outer side surface 148 and inner side surface 150 of the posterior member. This window or hole may allow bony growth into the window or hole and between the two posterior members 142, 144. The space 146, 152 within and/or between the posterior members 142, 144 may also be filled with graft materials (not shown). The graft material may be an autograft, allograft, xenograft or synthetic material. Synthetic graft material may be ceramic-based, silicon-based or calcium-based. The graft material may also include osteoinductive factors to promote bone ingrowth. One skilled in the art will appreciate that there are many varieties of synthetic graft materials and constituents that may be used between or about the hyoid bone segments.

Figure 9A:
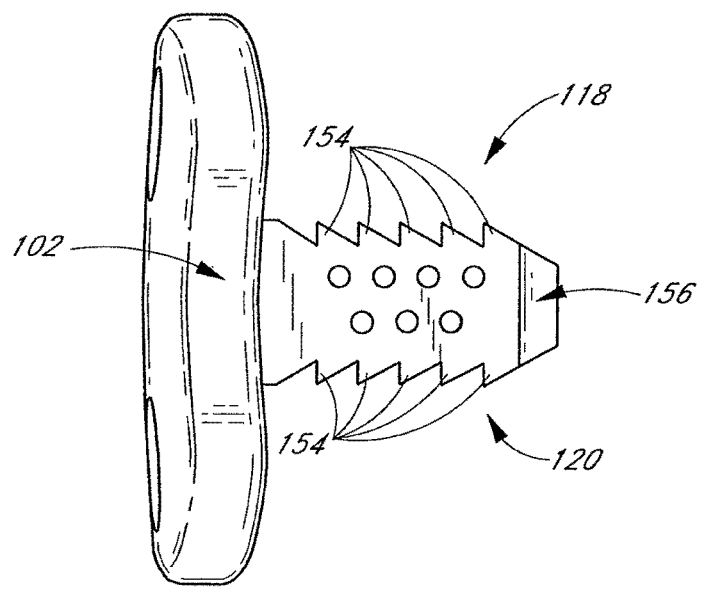
FIGS. 9A and 9B illustrate superior and lateral elevational views of another embodiment of an integrated fixation plate and spacer.
Figure 9B:
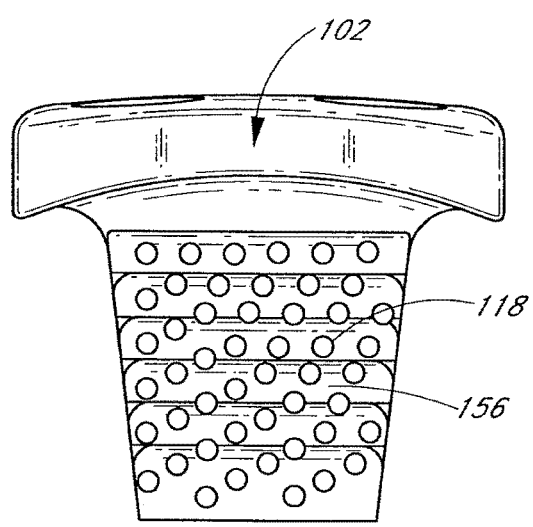

One or more surfaces of the implant may also have surface projections, indentations, or holes or pores that can further alter the characteristics of the implant. Referring to FIGS. 9A and 9B, in one embodiment, angled projections, barbs, teeth 154 or ramped surfaces which incline outwardly from one or more spacer surfaces toward the fixation plate 102 may be provided on one or more surfaces that allow insertion of the spacing structure in one direction but resist movement in the opposite direction. These teeth 154 may be advantageous in reducing the migration of the device out of the intervertebral space. Improved fixation of the spacer 156 may maintain device position during drilling of the screw holes into the vertebral bodies, and may also reduce the forces acting upon the screws or other retaining structures, thereby reducing the risk of backout. The teeth 154 are preferably provided on the superior and/or inferior surfaces 118, 120 of the spacer 156, but other surfaces may also have teeth or other tissue engagement structures.

As illustrated in FIGS. 9A and 9B, in one embodiment, the tissue engagement structures may be combined with indentations, holes or pores for allowing bony ingrowth or filling with bony matrix or graft materials as previously described. These holes may be utilized with other surface features to further enhance insertion and stabilization of the implant.

In one embodiment, the spacer has a height of about 4 mm to about 50 mm, or preferably about 4 mm to about 12 mm. Occasionally, the spacer has a height of about 6 mm to about 9 mm. In some embodiments, the spacer has a length along the AP axis, as measured from the bone facing surface of the fixation plate to the most posterior end of the spacer, of about 5 mm to about 25 mm. In some embodiments, the spacer length is about 10 mm to about 15 mm. The width of the spacer is generally about 5 mm to about 25 mm, and in some situations, about 10 mm to about 15 mm. One skilled in the art can dimension the spacer based upon the implantation location and specific vertebral morphology, neurological anatomy and disease state.

The spinal fusion implant may include, be made of, treated, coated, filled, used in combination with, or contain artificial or naturally occurring materials suitable for implantation in the human spine. These materials include any source of osteogenesis, bone growth-promoting materials, bone derived substances, bone morphogenetic proteins, hydroxyapatite, genes coding for the production of bone, and bone including, but not limited to, cortical bone. The implant can also be formed of material such as metal including, but not limited to, titanium and its alloys, surgical grade plastics, plastic composites, ceramics, or other materials suitable for use as a spinal fusion implant. In some embodiments, the device comprises a radiolucent material, a radio-opaque material, or a combination thereof. A device that is partially or completely radiolucent may be advantageous when evaluating the effect of the implant post-implantation. Many existing spinal fixation plates and/or spacers obscure visualization of the vertebrae, which can complicate post-operative treatment, diagnosis and prognosis of the patient's condition. The implant may include at least in part materials that are bioabsorbable in the body. The implant of the present invention can be formed of a porous material or can be formed of a material that intrinsically participates in the growth of bone from one of adjacent vertebral bodies to the other of adjacent vertebral bodies. The implant may be treated with, coated with, or used in combination with substances to inhibit scar tissue formation. The implant of the present invention may be modified, or used in combination with materials to provide antibacterial properties, such as, but not limited to, electroplating or plasma spraying with silver ions or other substance. The implant may optionally comprise an electrical source to provide ionophoresis of the silver ions into the surrounding tissue to prevent infection. The antibacterial properties may include bactericidal and/or bacteriostatic characteristics. Similarly, antifungal characteristics may also be provided. Any of these materials as appropriate may be used at any time after the implant(s) are inserted.

2. Fixation Component

The fixation plate may have a generally flat configuration, curved configuration or combination thereof. Optionally, each surface of the fixation plate may also have a generally flat or curved configuration or combination thereof. Each surface of the fixation plate need not have the same configuration. The edges of the fixation plate may optionally be rounded, smoothed or polished. In one embodiment, the flange is dimensioned such that flange extends about 2 mm beyond the edges of the base of the spacer. In some embodiments of the invention, the fixation component is dimensioned to extend generally about 1 mm to about 20 mm beyond the cross sectional border of the spacer component at its interface with the fixation plate. In other embodiments, the flange may extend by 3 mm or 4 mm or more beyond the spacer base. The flange may or may not extend uniformly along the spacer edges. The shape of the flange may be different from the shape of the spacer base.

In some embodiments, the average thickness of the fixation plate is within the range of about 1 mm to about 5 mm. In other embodiments, the average thickness of the fixation plate is within the range of about 1.5 mm to about 3.0 mm. The thicknesses of the fixation plate need not to be uniform. In one embodiment, the fixation plate is conformable to the vertebral surfaces of the implantation sites.

In other embodiments of the invention, the spacer component is attached to a fixation component comprising a mesh or lattice. The fixation component may also be made from a material that is the same or different from the spacer component. In some instances a fixation component and a spacer component having different materials may be beneficial because the spacer component may be configured to withstand compressive forces while the fixation component is configured to withstand primarily tension forces. The fixation component may comprise a polymer, a woven material, or a combination thereof.

Figure 10A:
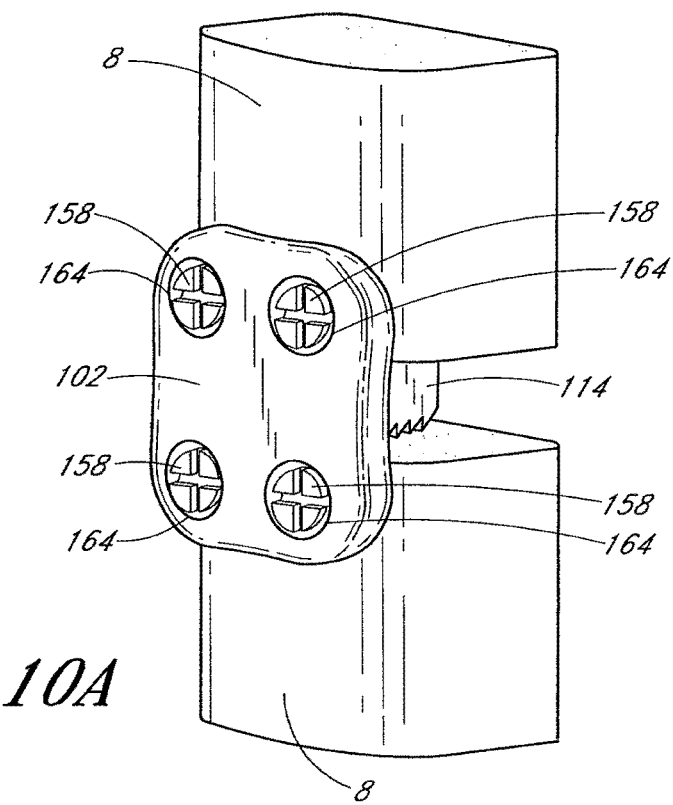
FIGS. 10A and 10B are schematic perspective and lateral views of one embodiment of the invention attached to a vertebral column.
Figure 10B:
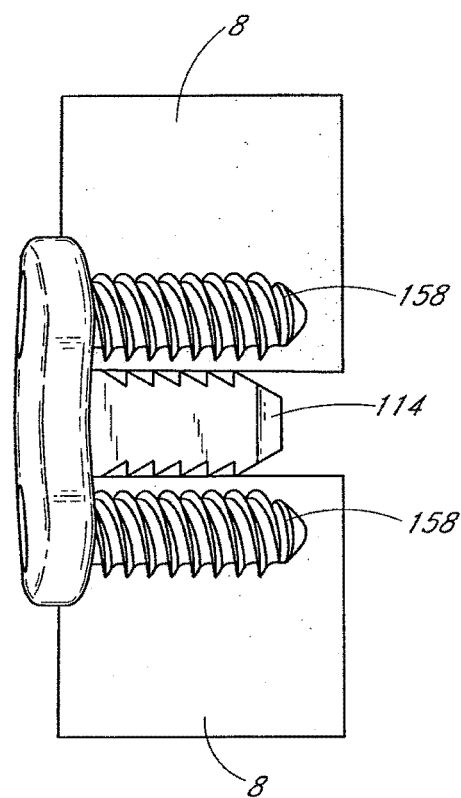
Figure 10C:
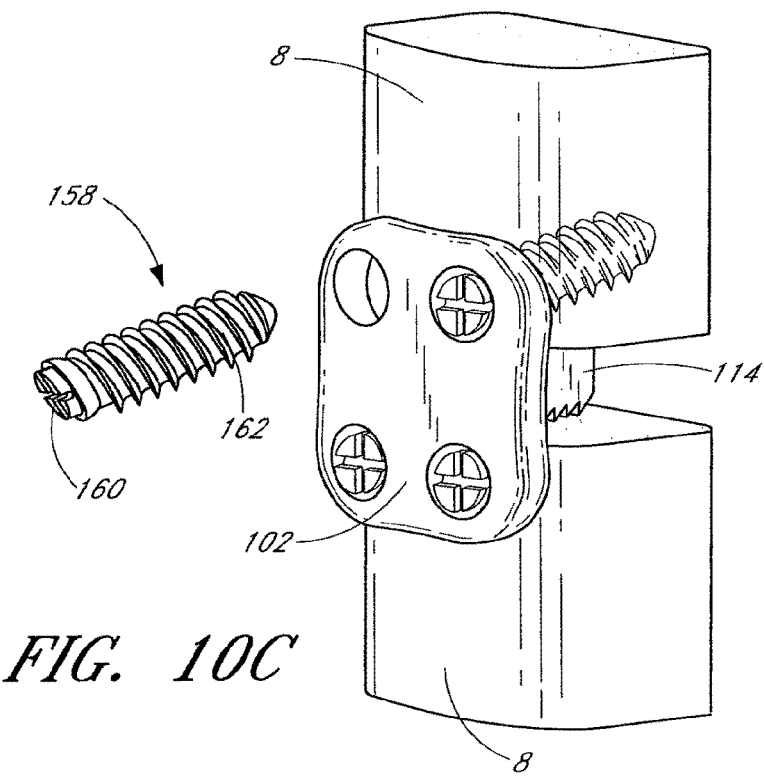
FIGS. 10C and 10D are schematic perspective and lateral views of another embodiment of the invention attached to a vertebral column with angled screws.
Figure 10D:
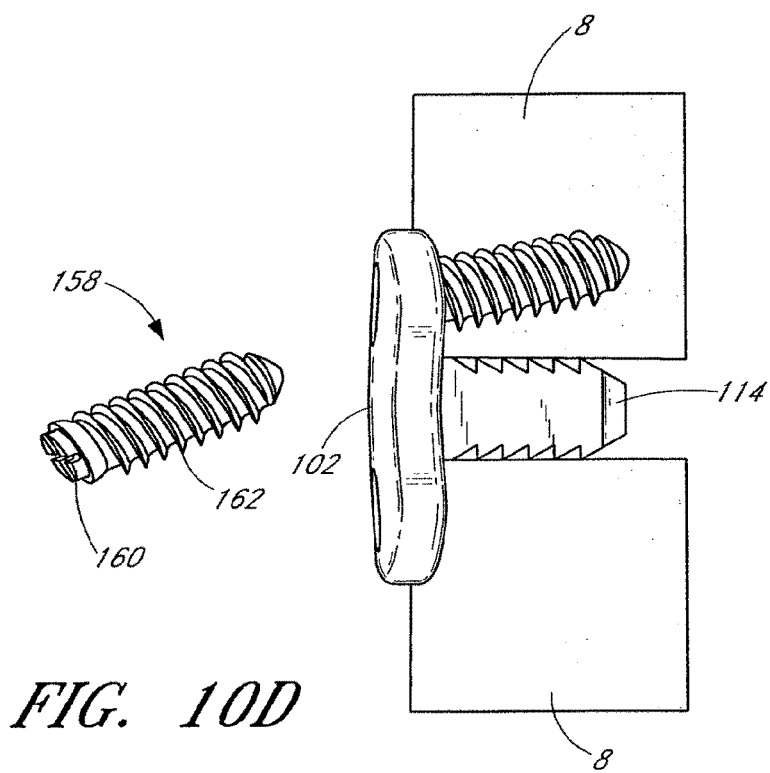

Referring back to FIGS. 5A through 5C, each upper portion and lower portion of the fixation plate 102 has one or more spaces or holes 112 oriented between the bone facing surface 108 and access surface 110 that are configured to accept screws and/or other attachment elements for anchoring the implant to the vertebral bone. As shown in FIGS. 10A and 10B, in some embodiments of the invention, one or more bone screws 158 configured for insertion through one or more screw holes 112 in the fixation plate 102 are provided. As shown in FIGS. 10C and 10D, each bone screw 158 typically comprises a screw head 160 and a screw body 162. The bone screws 158 and/or anchors may or may not be self-tapping. In some embodiments, the invention further comprises bone anchors comprising an anchor head and an anchor body. The anchor head is adapted to interface with the fixation plate to hold the fixation plate against the adjacent vertebral bone structures. The anchor body comprises threads or barbs for piercing or inserting into bone and fixing the position of the anchor head. The anchor body may or may not form an interface with the holes of the fixation plate to further fix the position of the fixation plate with respect to the vertebral bone.

Each hole 112 of the flange or fixation plate 102 need not have the same configuration or size. The holes 112 are typically round in cross section and dimensioned to allow passage of a screw body 162 therethrough while resisting passage of the screw head 160 completely through the hole 112. In other embodiments, however, at least a portion of the hole 112 may have a non-round cross-section, such as an oval, square, rectangle, polygonal or other closed shape. The inside surface of the holes 112 may be covered with a lubricious coating to facilitate insertion and/or movement of a screw or other attachment device through the hole.

Figure 11:
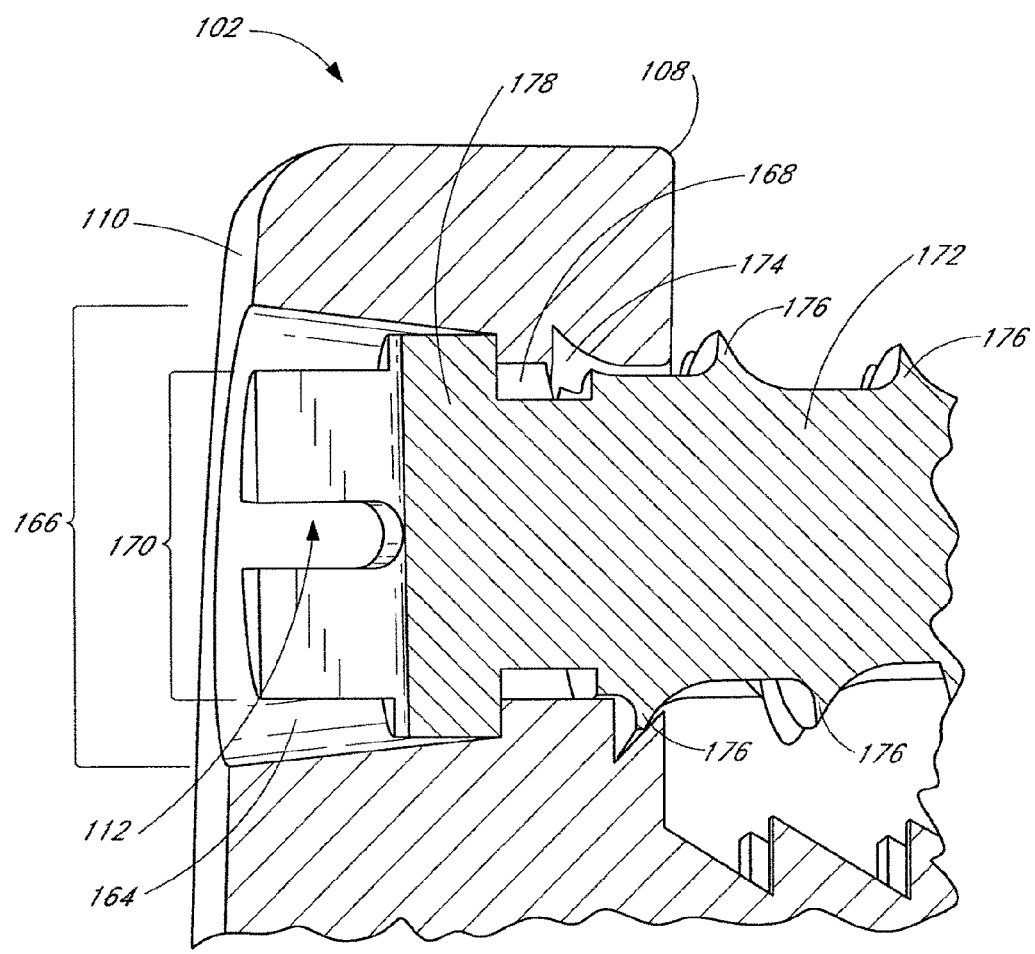
FIG. 11 depicts a cross sectional magnified view of one embodiment of a screw and a fixation plate hole.

In one embodiment, depicted in each hole FIG. 11, comprises a first inside surface 164 adjacent to the access surface 110 having a first diameter 166, and a second inside surface 168 adjacent to the bone facing surface 108 having a second diameter 170. In some embodiments, either one or both of the first inside surface 164 and second inside surface 168 may be dimensioned to align a corresponding screw 172 in generally one particular orientation. In one embodiment, the second inside surface 168 of a screw hole 112 comprises threads 174 and adapted to form a rotatable mechanical interfit with threads 176 on a corresponding screw 172 inserted through the hole 112. The first inside surface 164 of the screw hole 112 may also be similarly threaded, or may be configured to accept the head 178 of a screw 172 inserted through the hole 112 to allow flush positioning or recessed positioning of the screw head 178 with the access surface 110 of the fixation plate 102.

The bone anchor or screw 172 for the particular flange hole 112 is typically selected so that the largest diameter of the screw or anchor head 178 is larger than the second diameter 170 of the hole 112. For non-recessed screws or anchors, the largest diameter of the screw or anchor head 178 may be larger than the first diameter 166. For flush, partially or completely recessed screws or anchors, the largest diameter of the screw or anchor head 178 is between the first diameter 166 and the second diameter 170. In one embodiment, the flange holes 112 may have a first diameter 166 of about 3 mm to about 10 mm, and in other embodiments, may have a diameter of about 4 mm to about 6 mm. In one embodiment, the flange holes 112 may have a second diameter 170 of about 0.1 mm to about 4.0 mm smaller than the first diameter, and in one embodiment, may have a second diameter 170 of about 0.2 mm to about 1.0 mm smaller than the first diameter 166, or even about 0.2 mm to about 0.4 mm smaller than the first diameter 166. In one embodiment, the screw head or anchor head 178 may have a diameter of about 3.2 mm to about 10.2 mm, and in one embodiment, may have a diameter of about 4.4 mm to about 6.4 mm.

For embodiments where the first inside surface 164 of the hole 112 is adapted for recessed positioning of the screw head 178, the recessed positioning may be partial or complete. With partial recessed positioning, only a portion of an inserted screw lies below the access surface 112 of the fixation plate 102, while with complete recessed positioning, all the screw head 178 may lie at or below the access surface 112 of the fixation plate 102. The screw hole 112 about the first inside surface 164 can have any of a variety of cross sectional shapes.

In some embodiments, the one or more holes are configured to align a screw 172 having a general perpendicular orientation with respect to either or both the access surface 110 or bone facing surface 108 of the flange 102. In some embodiments, one or more holes 112 may be configured to align a screw in a skewed orientation. Sometimes, the skewed orientation may have a slight superior or inferior angle, depending upon whether the hole is located on the upper portion or lower portion of the flange, respectively. A skewed orientation in the superior/inferior direction may reduce the risk that the screw 172 remains secure in the vertebral body by providing sufficient bone structure between the screw body and the intervertebral space. In one embodiment, a screw hole 112 is configured to accept a screw 172 in an orientation that is within the range of about 0 degrees to about 60 degrees superiorly with respect to the plane between the two corresponding vertebrae. In one embodiment, the screw hole is configured to accept a screw 172 in an orientation that is within the range of about 5 degrees to about 30 degrees superiorly, and in some embodiments, to accept a screw 172 in an orientation that is within the range of about 10 degrees to about 20 degrees superiorly. In one embodiment, a screw hole 172 is configured to accept a screw 172 in an orientation that is within the range of about 0 degrees to about 60 degrees inferiorly with respect to the transverse plane between the two corresponding vertebrae 4. In one embodiment, the screw hole 112 is configured to accept a screw 172 in an orientation that is within the range of about 5 degrees to about 30 degrees inferiorly, and in some embodiments, to accept a screw 172 in an orientation that is within the range of about 10 degrees to about 20 degrees inferiorly. The particular orientation of a screw hole 112 may be determined by the dimensions of the screw 172 used with the device and the vertebrae 4 to which the device is to be attached.

One or more holes 112 of the flange 102 may also be configured to a skewed angle in the medial/lateral direction. Typically, the hole 112 may be configured with a medially directed screw orientation to avoid insertion of a screw through the outer surface of the vertebral body or through a pedicle, but a lateral screw orientation may also be used. Screw holes 112 located medially on the flange 102 may have a lateral orientation. In one embodiment, a screw hole 112 is configured to accept a screw 172 in an orientation that is within the range of about 0 degrees to about 45 degrees medially with respect to the sagittal plane through a vertebra 4. In one embodiment, the screw hole 112 is configured to accept a screw 172 in an orientation that is within the range of about 5 degrees to about 30 degrees medially, and in some embodiments, to accept a screw 172 in an orientation that is within the range of about 10 degrees to about 20 degrees medially. In one embodiment, a screw hole 112 is configured to accept a screw 172 in an orientation that is within the range of about 0 degrees to about 45 degrees lateral with respect to the sagittal plane through the vertebrae 4. In one embodiment, the screw hole is configured to accept a screw 172 in an orientation that is within the range of about 5 degrees to about 30 degrees laterally, and in some embodiments, to accept a screw 172 in an orientation that is within the range of about 10 degrees to about 20 degrees laterally. One or both of the first and second inside surfaces 165, 168 may be threaded and capable of forming a rotatable interfit with the threads of a corresponding screw 172 or other attachment device. One or more holes 112 of the flange 102 may also be configured to accept and/or orient the tip of a corresponding drill guide so that screw holes in the vertebrae 4 may be created after the device has been positioned at its implantation site. By drilling screw holes into the vertebrae 4 after the positioning of the device, the risk of misaligned vertebral screw holes and flange holes 112 may be reduced. Misalignment may result in an ill-fitting and unstable implant.

Figure 12:
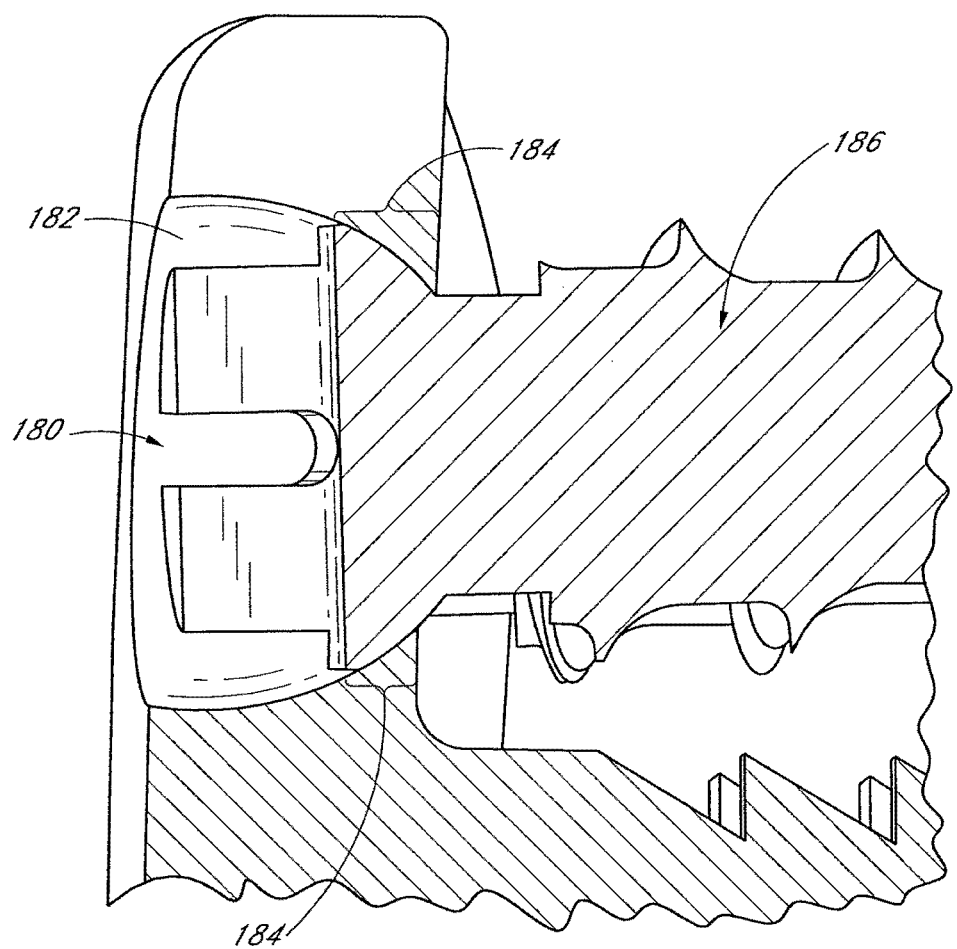
FIG. 12 depicts a cross sectional magnified view of one embodiment of a screw and a polyaxial fixation plate hole.

In some embodiments of the invention, shown in FIG. 12, one or more screw holes of the fixation plate or flange may be configured to allow a range of corresponding screw orientations when the screw is inserted through the screw hole. In one embodiment of the invention, a polyaxial screw hole 180 wherein at least a portion of the inner surface 182 of the polyaxial screw hole 180 having a concave surface 184 that is capable of accepting a range of screw orientations within the screw hole 180. The concave surface 184 typically comprises an entire circumference of the inner surface of the screw hole 180, but in some embodiments, may comprise only one or more portions of a screw hole 180 circumference. Concave surfaces along limited portions of a circumference may allow pivoting or a range of movement along one axis of the screw hole 180 while limiting the pivoting along another axis of the screw hole 180. In some embodiments, the distal surface 188 of the screw head 190 may be configured with a convexity complimentary to the concave surface 184 of the screw hole 180.

In one embodiment, a screw hole 180 is configured to provide a screw orientation range of about 0 degrees to about 60 degrees from the central axis of the screw hole. In one embodiment, the screw hole 180 is configured to provide a screw orientation range up to about 5 degrees to about 30 degrees from the central axis of the screw hole, and in some embodiments, to provide a screw orientation range up to about 10 degrees to about 20 degrees. In one embodiment, a screw hole 180 is configured to provide a screw orientation range of about 0 degrees to about 60 degrees superiorly with respect to the plane between the two corresponding vertebrae 4. In one embodiment, the screw hole 180 is configured to provide a screw orientation range of about 5 degrees to about 30 degrees superiorly, and in some embodiments, to provide a screw orientation range of about 10 degrees to about 20 degrees superiorly. In one embodiment, a screw hole 180 is configured to provide a screw orientation range of about 0 degrees to about 60 degrees inferiorly with respect to the transverse plane between the two corresponding vertebrae. In one embodiment, the screw hole 180 is configured to provide a screw orientation range of about 5 degrees to about 30 degrees inferiorly, and in some embodiments, to provide a screw orientation range of about 10 degrees to about 20 degrees inferiorly. The particular orientation of a screw hole may be determined by the dimensions of the screw 186 used with the device and the vertebrae 4 for which the device is to be attached. One or more holes 180 of the flange 102 may also be configured to a skewed angle in the medial/lateral orientation. Typically, the hole 180 may be configured with a medially directed screw orientation to avoid insertion of a screw 186 through the outer surface of the vertebral body 8 or through a pedicle 12, but a lateral screw orientation may also be used. In one embodiment, a screw hole is configured to provide a screw orientation range of about 0 degrees to about 45 degrees medially with respect to the sagittal plane through a vertebra. In one embodiment, the screw hole is configured to provide a screw orientation range of about 5 degrees to about 30 degrees medially, and in some embodiments, to provide a screw orientation range of about 10 degrees to about 20 degrees medially. In one embodiment, a screw hole is configured to provide a screw orientation range of about 0 degrees to about 45 degrees lateral with respect to the sagittal plane through the vertebra. In one embodiment, the screw hole is configured to provide a screw orientation range of about 5 degrees to about 30 degrees laterally, and in some embodiments, to provide a screw orientation range of about 10 degrees to about 20 degrees laterally. FIGS. 10A and 10B depict one embodiment of the invention comprising an implant with a square-shaped flange 102 with four polyaxial screw holes 164 wherein the screws used to secure the implant to the vertebrae were inserted with an orientation that is in a generally neutral orientation with respect to the bone facing surface 108 of the flange or fixation plate 102. In one embodiment, the screw holes 164 in the upper portion of the flange 102 may be configured in the vertical axis to allow an insertion angle of about +30 degrees to about −15 degrees. The screw holes 164 in the lower portion of the flange 102 may be configured to provide an insertion range of about +20 degrees to about −5 degrees in the vertical axis. FIGS. 10C and 10D shows the use of the implant in FIGS. 10A and 10B with at least one screw 158 inserted through an upper screw hole 164 of the implant and into the upper vertebral body of an intervertebral space with a superiorly angled orientation. In some instances, this screw orientation may reduce the risk of bone fracture into the intervertebral space with or without migration of the screw body into the same space.

Figure 13A:
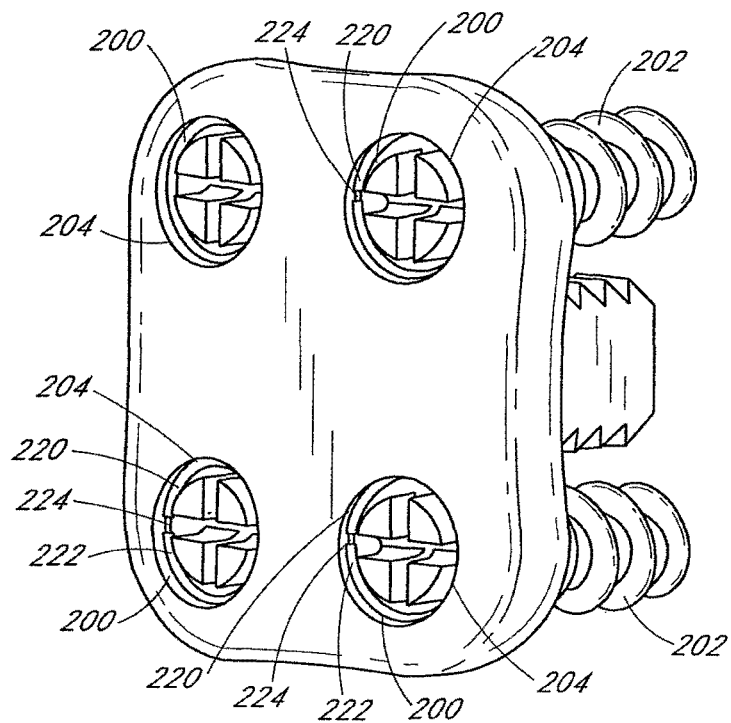
FIG. 13A is a perspective view of one embodiment of the invention comprising a retaining ring and fixation hole insert.
Figure 13B:
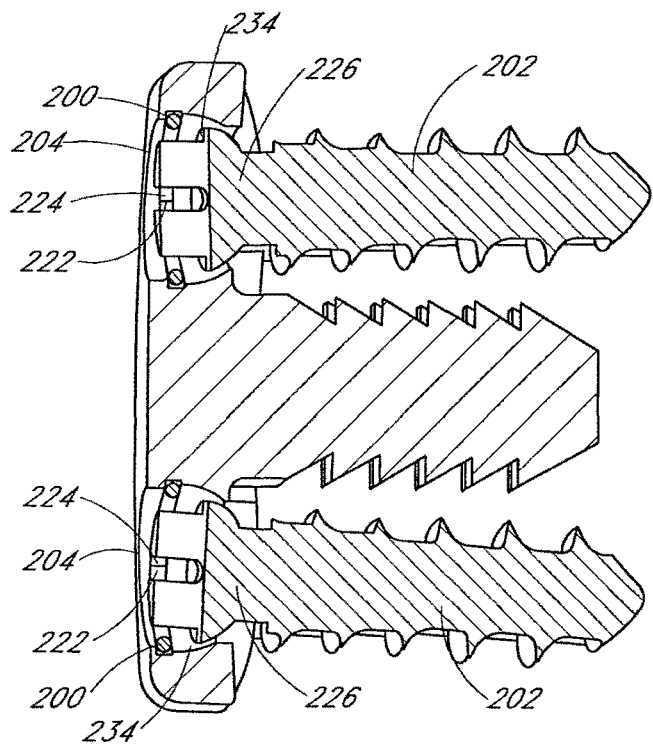
FIGS. 13B and 13C are cross sectional views of the device in FIG. 13A.
Figure 13C:
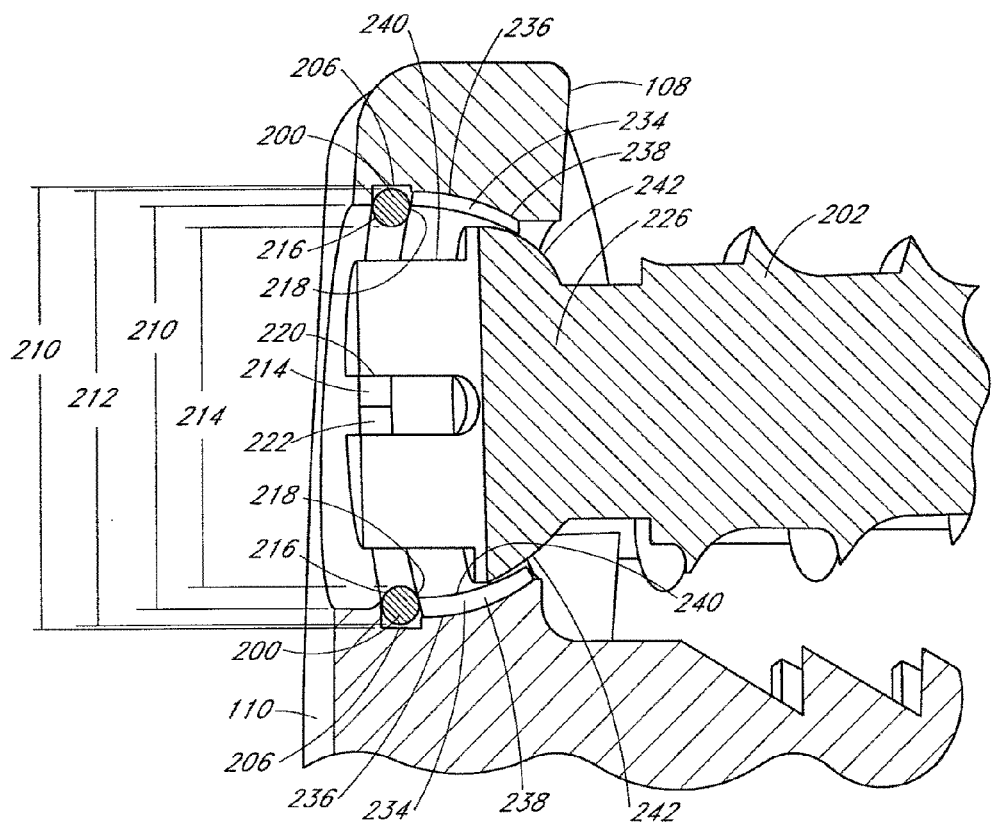

In one embodiment of the invention, one or more additional screw hole structures are provided to further interact with an inserted screw. FIGS. 13A through 13C depict one embodiment of the invention comprising an expandable/collapsible retainer ring or collar 200. The retainer ring/collar 200 allows insertion of a corresponding screw 202 in one direction through a screw hole 204 but resists movement of the screw 202 in the opposite direction. The retainer ring/collar 200 may be positioned within one or more screw holes 204 with a recess or indentation 206 along at least a portion of its circumference capable of accepting at least the outside diameter portion of the retainer ring/collar 200. The recess or indentation 206 typically comprises a circumferential channel of the flange hole 204 having a recess diameter 208 that greater than the first diameter 210 of the flange hole 204. The recess or indentation 208 is typically located closer to the access surface 110 of the fixation plate 102, rather than the bone facing surface 108, but may also be located at other positions within the screw hole 204. The ring or collar 200 has an outside retainer diameter 212 and an inside retainer diameter 214, a first surface 216 between the outside retainer diameter 212 and inside retainer diameter 214 closer to the access surface 110 of the fixation plate 102 and a second surface 218 between the outside retainer diameter 212 and inside retainer diameter 214 closer to the bone facing surface 108 of the fixation plate. Changes in the inside retainer diameter of the retainer may or may not alter the outside retainer diameter of the retainer, and vice versa. In some embodiments, the retainer ring or collar has a completely closed configuration, but in other embodiments, as shown in FIGS. 13A to 13C, the ring or collar 200 has an interrupted configuration comprising two ends 220, 222 about an expansion space 224. The retainer ring/collar 200 is capable of radial expansion and collapse by altering the distance between the two ends 220, 222.

In one embodiment, the retainer ring 200 is configured to resiliently collapse such that the outside retainer diameter 212 is less than the first diameter 166 of the flange hole 204 so that the retainer ring may be passed into the flange hole recess 206. The retainer ring 200 can then re-expand its outer retainer diameter 212 to at least partially occupy the flange hole recess 206. The retainer ring 200 is further configured to resiliently expand its inside retainer diameter 214 to allow passage of a screw or anchor head 226 through the retainer ring/collar 200. Expansion of the inside retainer diameter 214 may or may not result in expansion of the outside retainer diameter 212 to occupy additional space within the flange hole recess. In some embodiments, the retainer ring/collar comprises a compressible or deformable material such that the inside retainer diameter can be increased without requiring increase in the outside retainer diameter.

By configuring the retainer ring/collar 200 to resiliently deform when the screw or anchor head 226 is passed through the retainer ring/collar 200 with an increased force, the retainer ring/collar 200 can resist backout of the screw 202 or anchor where the backout forces acting on the screw 202 or anchor are insufficient to cause ring/collar 200 expansion and allow movement of the screw 202 or anchor. The force required to backout the screw or anchor may be increased relative to the force required to pass the screw or anchor through the retaining ring/collar by providing a ramped surface about the retaining ring/collar and/or the screw or anchor head.

Figure 14:
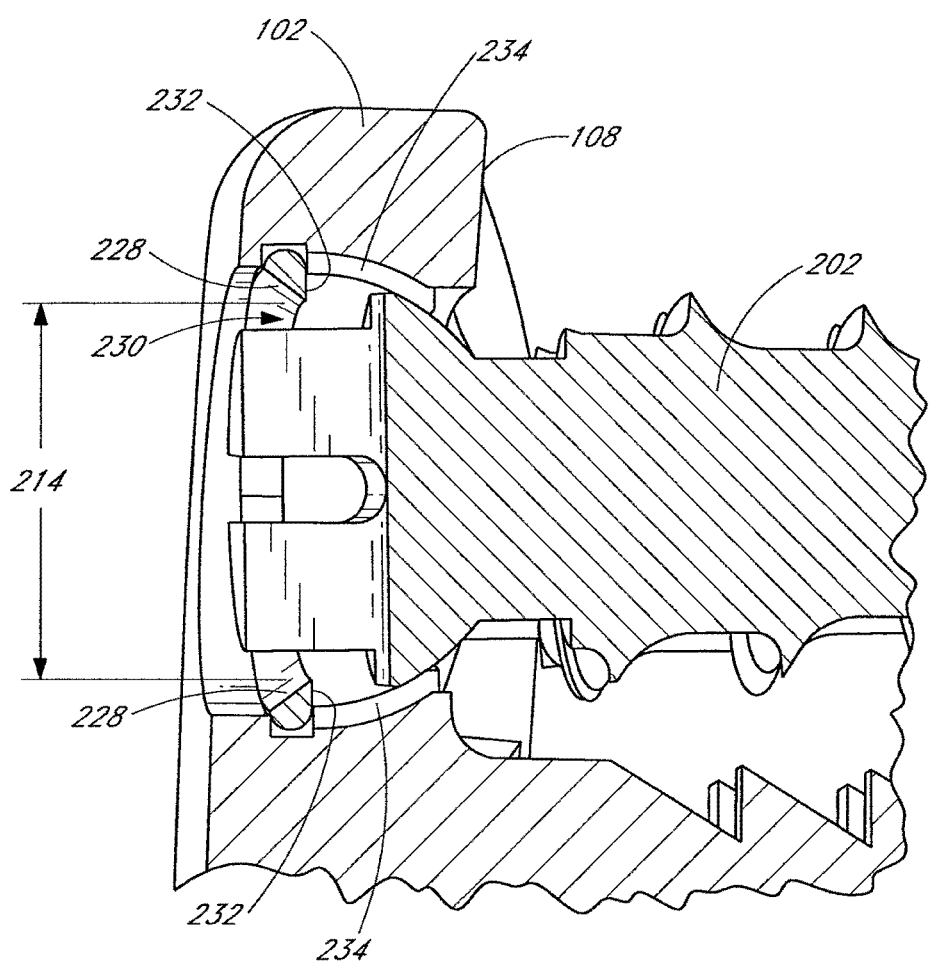
FIG. 14 is a cross sectional view of another embodiment of the invention comprising an angled retaining ring.

Referring to FIG. 14, a surface 228 about the inside retainer diameter 214 of a ring/collar 230 that is ramped or inclined radially inward toward the bone contact surface 108 of the fixation plate 102 may facilitate the insertion of the screw 202 or anchor through the retainer ring/collar while providing a larger second surface 232 of the screw or anchor to resist backout. Similarly, a screw or anchor head may also have a ramped or inclined surface radially outward from the screw body that may facilitate insertion of the screw or anchor through the retainer ring/collar while providing a larger screw or anchor head surface area to resist backout.

The cross sectional shape of the retainer structure may be any of a variety shapes, including a circle, oval, squares, rectangles, polygonal or other closed shape. The cross sectional shape of the retainer may vary along the length of the retainer. The cross sectional shape of the screw hole indentations may also be any of a variety of shapes, including a circle, oval, squares, rectangles, polygonal or other closed shape. The cross sectional shape of the retainer along the outside diameter may or may not be similar to the cross sectional shape of the screw hole circumferential indentation or recess.

In one embodiment of the invention, shown in FIGS. 13B and 13C, the implant further comprises an flange hole insert 234 that provides an intermediate layer of material between the screw or anchor head 226 and the inner surface 236 of the flange hole 204. The insert 234 may comprise a generally polymer, metallic, or ceramic member comprising an outer flange hole contacting surface 238 and an inner anchor contacting surface 240, where the outer flange hole contacting surface 238 is shaped to conform to at least a portion about the inner surface 236 of the flange hole 204. The anchor contacting surface 240 may or may not conform to at least a portion of the screw or anchor head surface 242. In one embodiment of the invention, the flange hole insert 234 is capable of absorbing wear forces transmitted between the fixation plate 102 and the screw 204 or anchor. Absorption of the forces between these two components of the implant may reduce the risk of implant failure and/or loosening that occurs at the interface between the two components.

In one preferred embodiment, the flanged interbody device comprises a polyaryl polymer, including but not limited to PEK, PEEK, PEKK, PEKEKK or a blend thereof, and the insert comprises a titanium or titanium alloy. Other combination may also be used as is known by those with skill in the art.

3. Complementary Flange Configurations

In one preferred embodiment, the flange is configured for positioning across an intervertebral space such that the upper portion of the flange is adapted to contact the superior vertebra and the lower portion of the flange is adapted to contact the inferior vertebra about an intervertebral space. In other embodiments, the flange may be configured to contact a single vertebra about an intervertebral space, or more than two vertebrae. In some embodiments, the flange may span two or more intervertebral spaces. Typically, the implant is adapted for positioning about the anterior surface of the vertebrae, along the anterior surfaces of vertebral bodies. In some instances, the flange of the implant may also be configured to contact other vertebral structures such as the pedicles, transverse processes, facet joints, superior and inferior articular processes and spinous processes. In still other embodiments, the implant is configured to attach to these vertebral structures without attaching or contacting the vertebral bodies.

In one embodiment of the invention, illustrated in FIGS. 5A through 5C, the flange 102 of implant 100 has a general square or rectangular shape and is dimensioned to allow stable attachment of the implant 100 to the adjacent vertebral bodies 8. The corners where any two sides of the flange meet may be angled, rounded or curved. The flanged implant 100 depicted in FIGS. 5A through 5C comprises rounded corners. In other embodiments, the flange 102 may comprise any of a variety of other shapes, including trapezoids, circles, ovals, polygons or other closed shapes. The flange 102 may or may not have a symmetrical configuration with respect the upper and lower portions and/or the left and right portions of the flange.

Figure 15A:
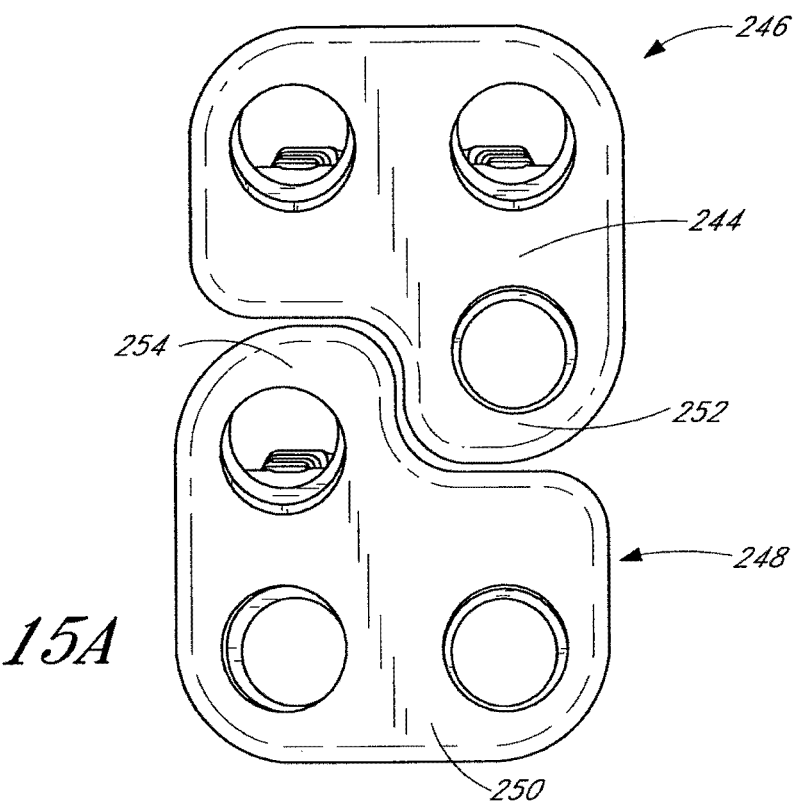
FIGS. 15A and 15B are frontal and perspective views of one embodiment of a complementary two spacer system.
Figure 15B:
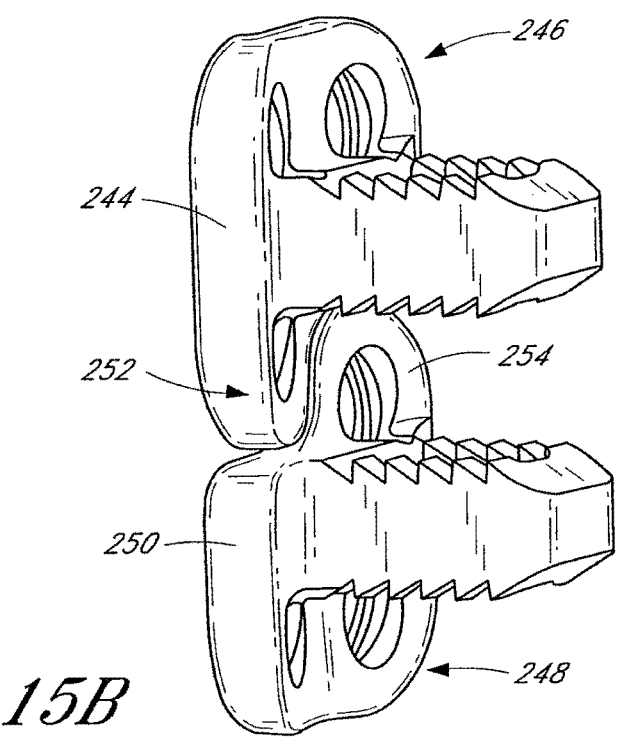

Depending upon the location of implantation, the shape and/or dimensions of the flange may or may not allow implantation of the additional implants at adjacent intervertebral spaces. In some embodiments, depicted in FIGS. 15A and 15B, the flange 244 of one implant 246 is configured and dimensioned to form a complementary shape with a corresponding adjacent implant and/or to prevent overlap or mechanical interference with an adjacent implant 248. The complementary fit between two adjacent implants may be loose or tight. The interface between the corresponding flanges may be non-overlapping as depicted in FIGS. 15A and 15B, or overlapping, as shown in FIGS. 25A and 25B. The complementary flanges may be asymmetric or symmetric with respect to the left and right portions of the flanges, and/or the upper and lower portions. Thus, the flange may be configured such that the vertical orientation of the flange, whether used right-side up or upside-down, does not affect the complementary interfacing with adjacent flanges.

FIGS. 15A and 15B depict one embodiment of the invention comprising an implant system with a superior implant and an inferior implant. The inferior portion 252 of the superior implant flange 244 has a right-sided asymmetry that is complementary to the corresponding left-sided asymmetry of the superior portion 254 of the inferior implant flange 250. The complementary-shaped flanges allow implantation of the superior flange and inferior flange at adjacent intervertebral spaces that would not otherwise allow implantation of traditionally shaped fixation plates. In other embodiments of the invention, the left/right asymmetry of each implant in the fixation system may be opposite. Furthermore, in some embodiments, as shown in FIGS. 15A and 15B, the superior implant 246 and flange 244 is identical to inferior implant 248 and flange 250 but is rotated 180 degrees.

Figure 16B:
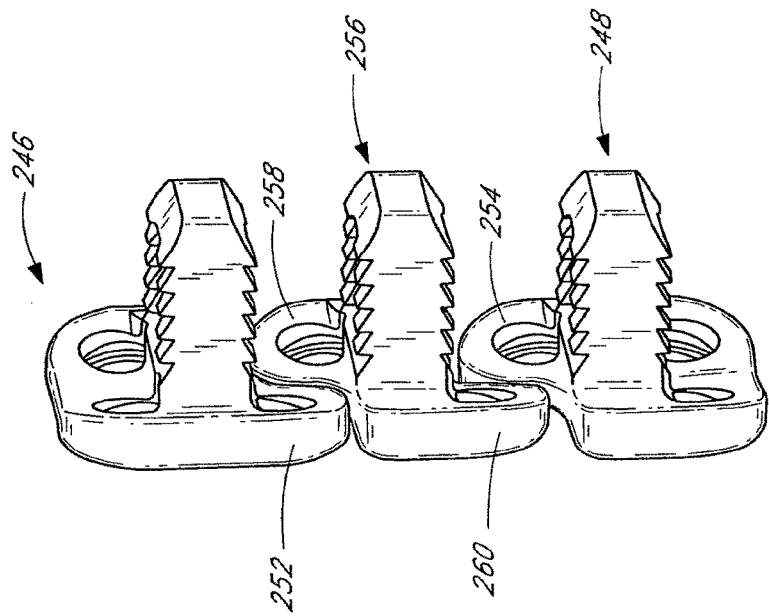
FIGS. 16A and 16B are frontal and perspective views of one embodiment of a complementary three spacer system.
Figure 16A:
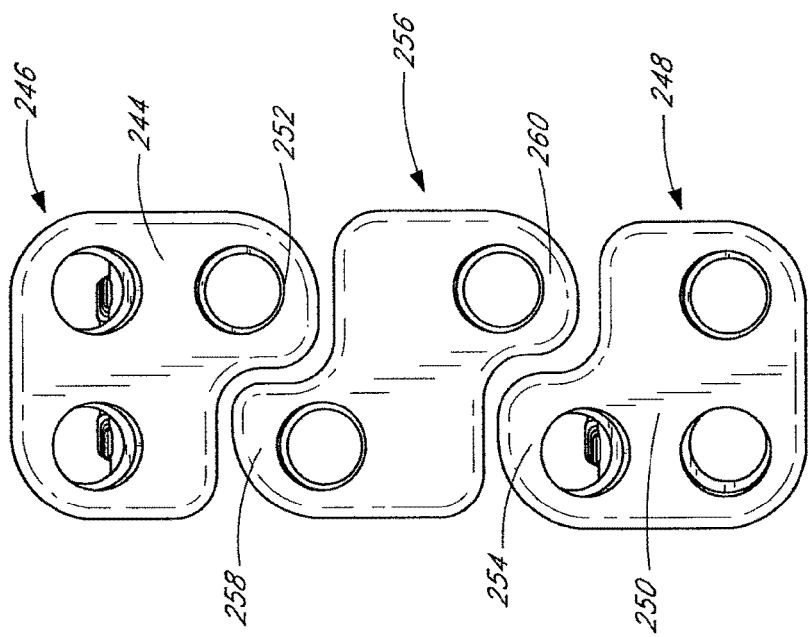

In one embodiment of the invention, illustrated in FIGS. 16A and 16B, the fixation system may further comprise one or more middle flange implants 256, a superior end flange implant 246 and/or an inferior end flange implant 248. The superior flange implant 246 and inferior flange implant 248 may have configurations and/or dimensions that have a greater surface area than the middle flange implants because there is only one implant, rather than two, adjacent to each of the end implants. This may provide and utilize the greater stability and securement available at the end implants 246, 248 compared to the middle implants 256. The inferior portion 252 of the superior flange implant 246 may have a right-sided asymmetry that is complementary to the corresponding left-sided asymmetry of the superior portion 258 of the middle implant flange 256. The inferior portion 260 of the middle flange 256 implant flange may have a right-sided asymmetry that is complementary to the corresponding left-sided asymmetry of the superior portion 254 of the inferior flange implant 248. The complementary-shaped flanges allow implantation of the superior, middle and inferior flanges at sequential intervertebral spaces that would not otherwise allow implantation of traditionally shaped fixation plates.

Figure 17B:
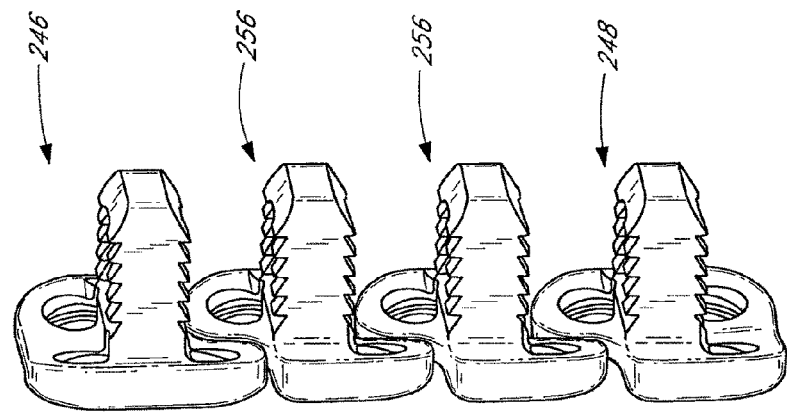
FIGS. 17A and 17B are frontal and perspective views of one embodiment of a complementary four spacer system.
Figure 17A:
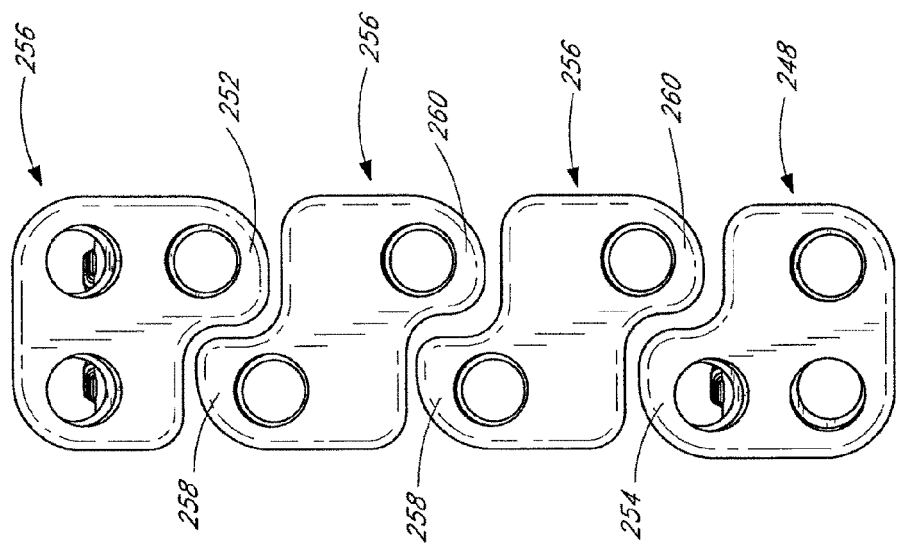

Referring to FIGS. 17A and 17B, in another embodiment of the invention, more than one middle flange implant is provided. In the particular embodiment shown in FIGS. 17A and 17B, the flange of each middle implant 256 is configured similarly, such that the superior portion 258 of each middle flange implant 256 is complementary to the inferior portion 260 of each middle flange implant 256, as well as the inferior portion 252 of superior flange implant 246.

Figure 18:
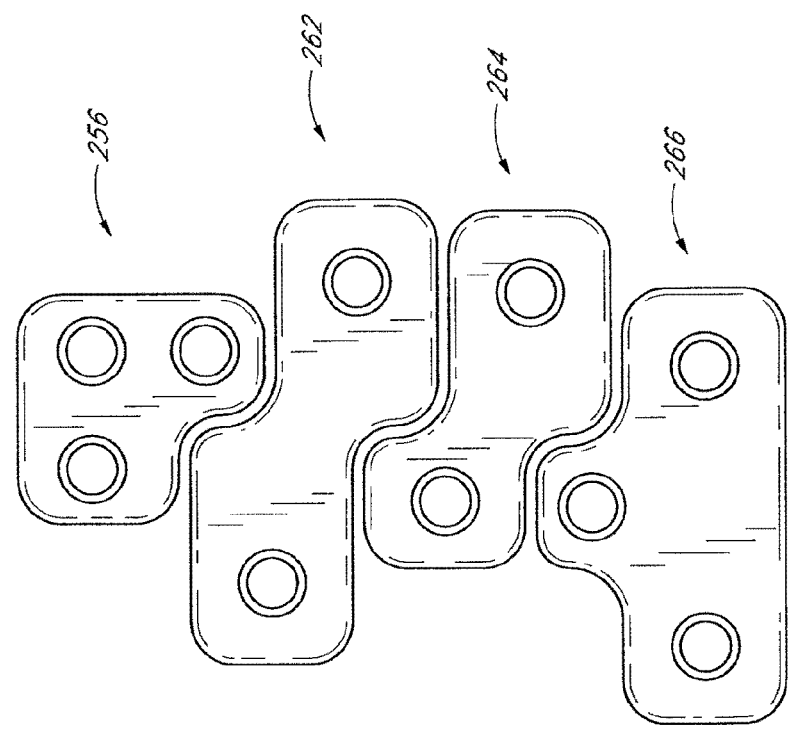
FIG. 18 is a frontal view of one embodiment of the invention comprising a variable width spacer system.

In some embodiments of the invention, a fixation system with serial implants of different widths is provided. As shown in FIG. 18, each implant comprises a left/right complementary configuration as previously described, but implants 256, 262, 264 and 266 having different left/right widths are provided. The different widths do not interfere with the complementary configurations of the implants 256, 262, 264, 266 in the fixation system. Having implants with different widths allow the selection of differently dimensioned implants as the size of the vertebrae change along a sequential length of the vertebral column. Furthermore, as illustrated in FIG. 18, the different widths of implants need not increase or decrease incrementally along the implantation sequence and may also allow tailoring of a particular implant to a particular vertebral anatomy along a sequence of vertebral implants. The differences in width of each implant need not be symmetrical with respect to the left and right sides. Spacers of different left/right widths may also be provided. Spacer size need not correlate with changes in flange size or configuration.

Figure 19:
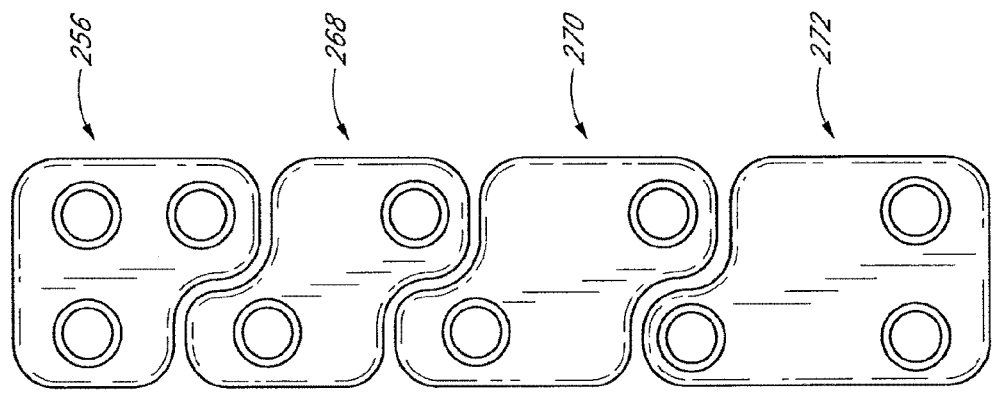
FIG. 19 is a frontal view of one embodiment of the invention comprising a variable height spacer system.

Referring to FIG. 19, implants 256, 268, 270, 272 of different heights may also be provided in some embodiments to compensate for changes in size of lower vertebrae and/or pathological changes in height. Implants of different heights may also have different widths.

Figure 20:
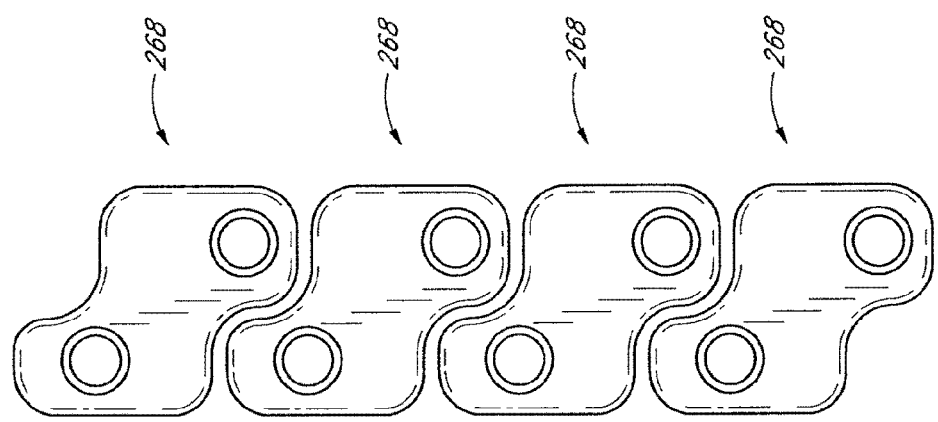
FIG. 20 is a frontal view of one embodiment of a complementary identical four spacer system.

Referring to FIG. 20, in another embodiment of the invention, each implant 268 of the fixation system has a superior flange portion that is complementary with the inferior flange portion of each implant without particular superior end and inferior end implants.

Figure 21:
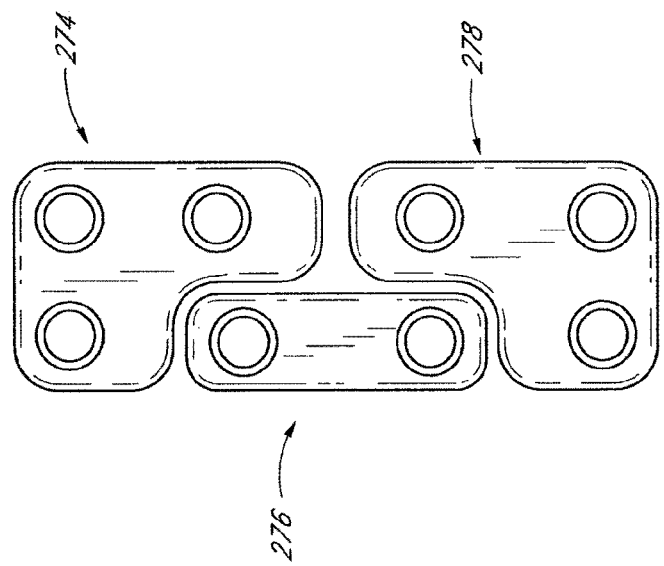
FIG. 21 is a frontal view of another embodiment of a complementary three spacer system.
Figure 23:
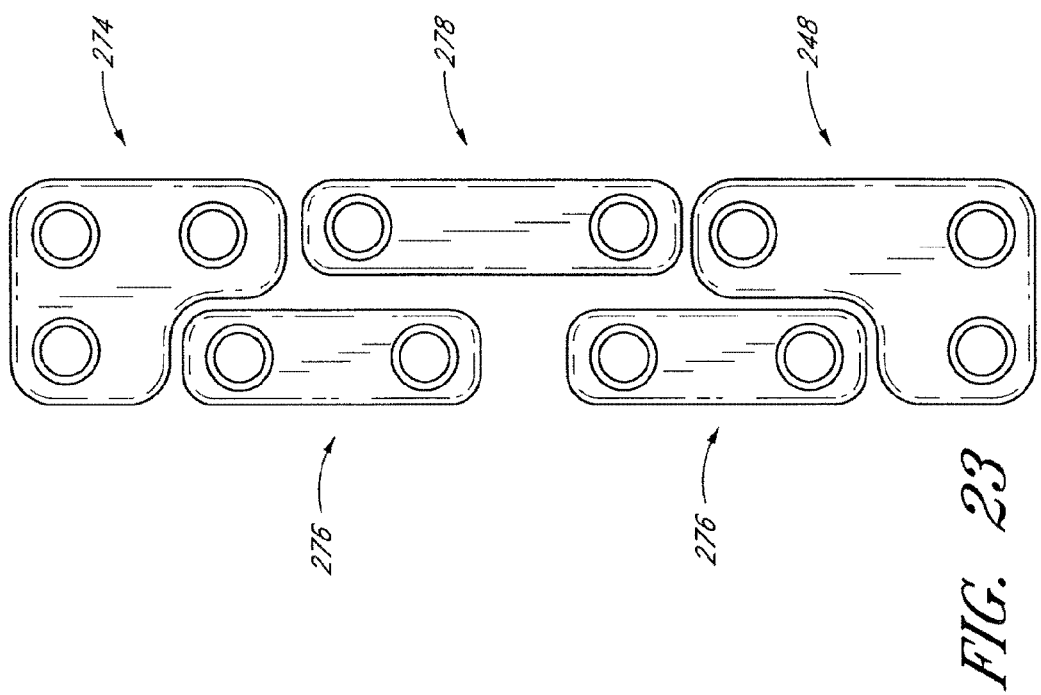
FIG. 23 is a frontal view of one embodiment of a complementary five spacer system.
Figure 22:
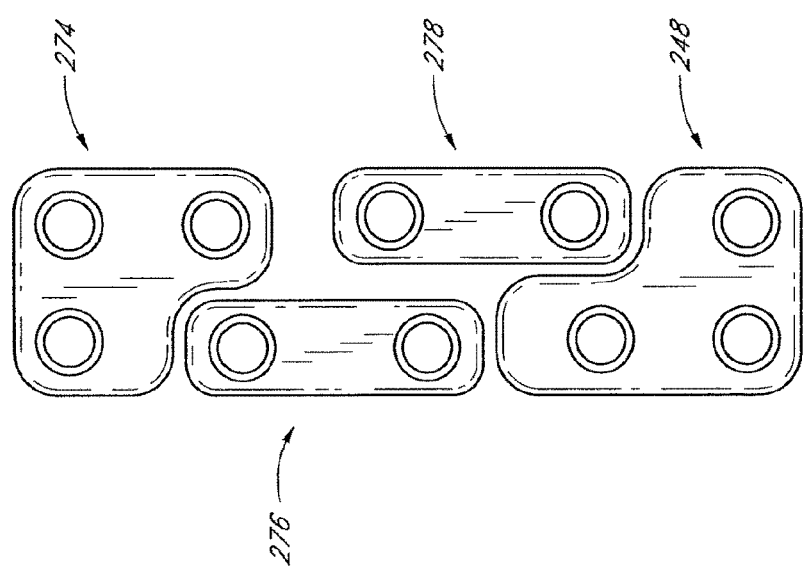
FIG. 22 is a frontal view of another embodiment of a complementary four spacer system.

FIGS. 21 through 23 depict embodiments of the invention where the superior and inferior portions of each implant flange in the fixation system are not complementary in a left/right manner, but each implant flange overall is complementary in a left/right manner. FIG. 21 depicts a three implant fixation system comprising a right-sided superior implant 274, a left-sided middle implant 276, and a right-sided inferior implant 278. FIG. 22 depicts a four implant fixation system comprising a right-sided superior implant 274, a left-sided middle implant 276, and a right-sided middle implant 278 and a left-sided inferior implant 278. In some instances, the left-sided middle implant 276 and right-sided middle implant 278 differs only by a 180-degree rotation. FIG. 23 represents a five implant fixation system comprising a left-sided superior implant 274, two right-sided middle implants 276, one left-sided middle implant 278 and a right-sided inferior implant 248. Likewise, six or more implants may be similarly configured and sequentially implanted.

Figure 24:
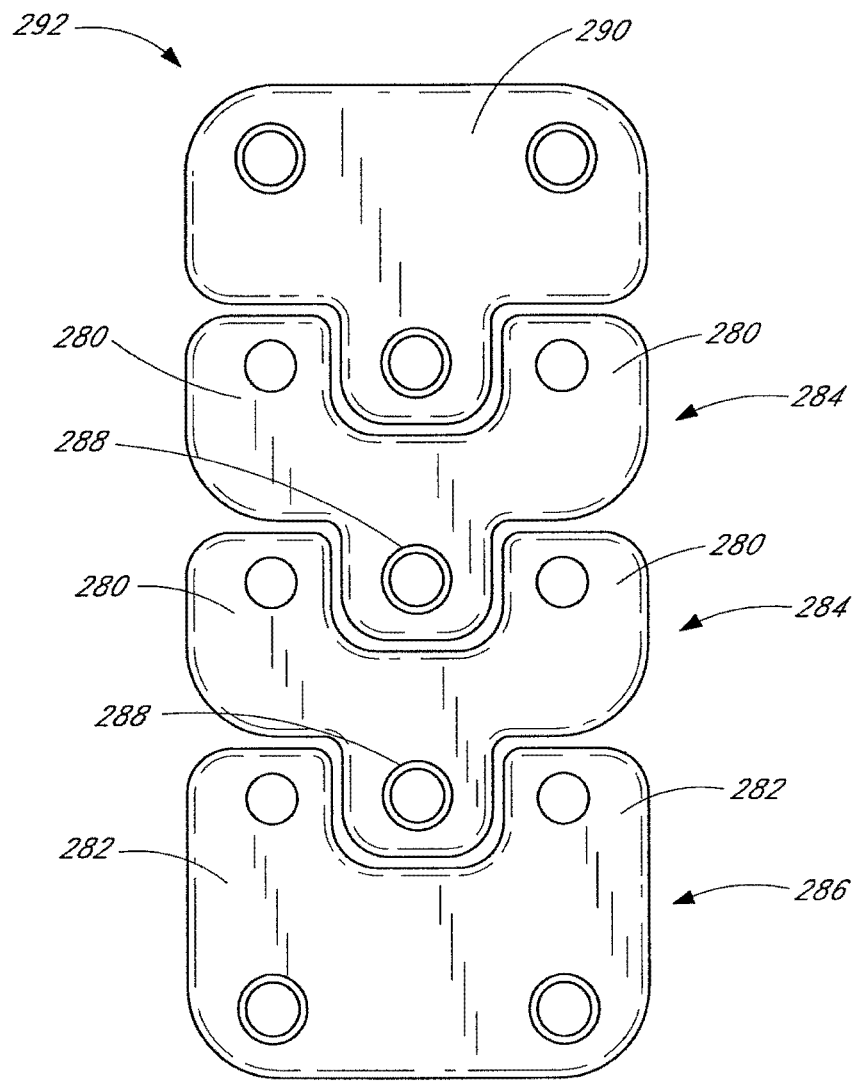
FIG. 24 is a frontal view of another embodiment of a complementary four spacer system.
Figure 26A:
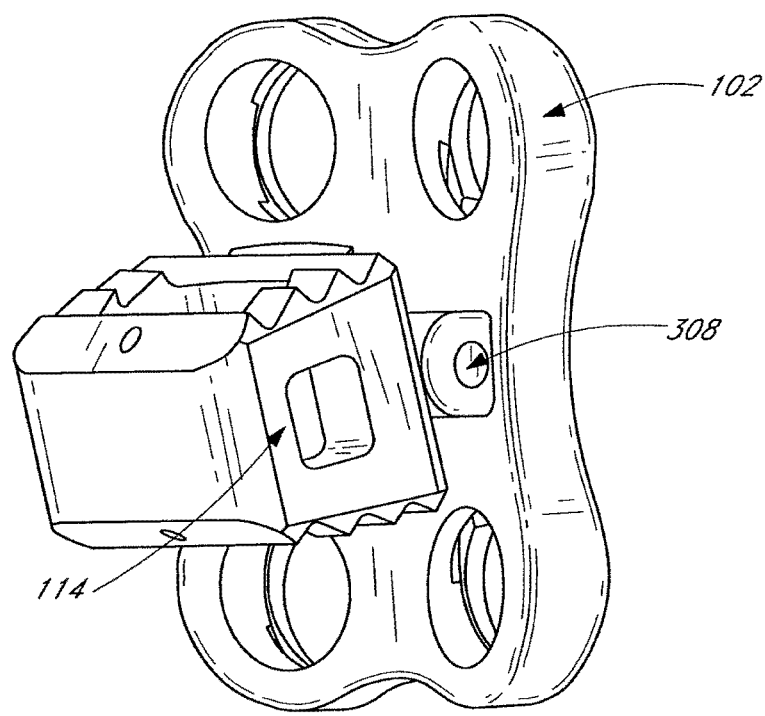
FIGS. 26A to 26D are various views of a pivotable interbody-plate device.
Figure 26B:
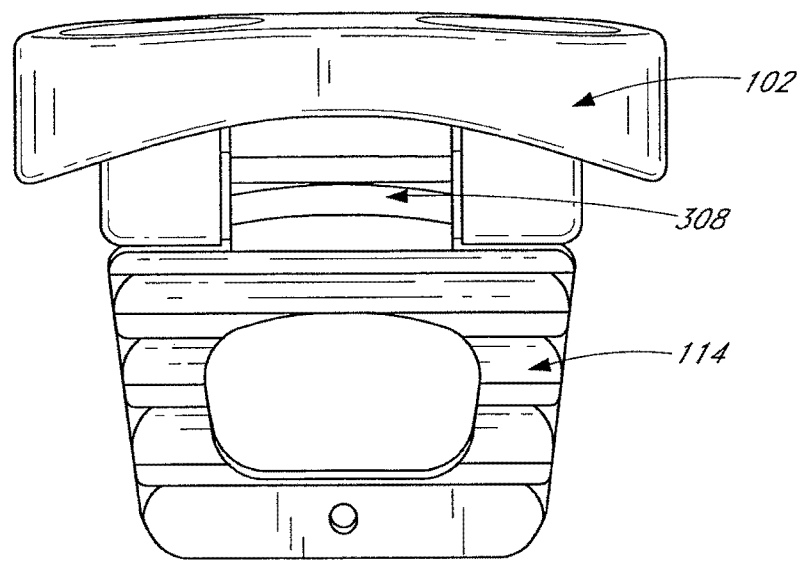
Figure 26C:
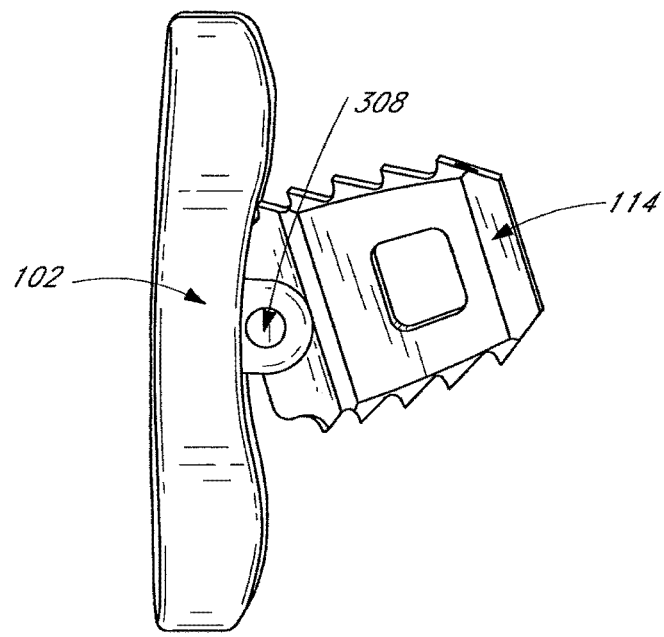
Figure 26D:
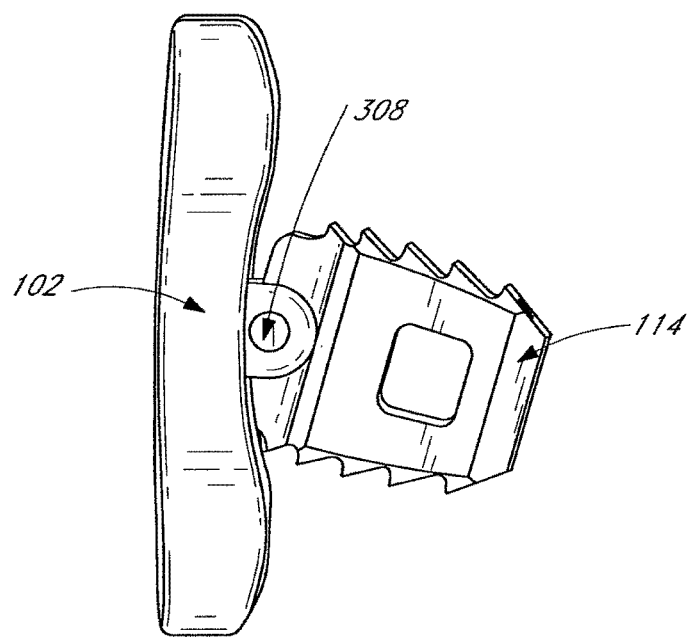

FIGS. 24 and 25A and 25B depict embodiments of the invention where the flange is configured to allow sequential implantation along the vertebral column but the flange and flange holes maintain a left/right symmetry. In one embodiment, it is hypothesized that maintaining left/right symmetry may reduce the torsional strain or stress acting upon the implants relative to the asymmetric implants described elsewhere in this application. Flanges with left/right symmetry, however, are not bound by this theory. FIG. 24 depicts one embodiment of the invention where the upper portions 280, 282 of the middle and inferior implant flanges 284, 286 have a bilateral configuration while the inferior portions 288, 290 of the middle and superior implant flanges 284 have a medial configuration. Although the embodiment shown in FIG. 24 comprises a superior end and inferior end implants 292, 286, neither implant 292, 286 is necessary for the invention.

FIGS. 25A and 25B illustrate one embodiment of the invention comprising implants 294, 296, 298 with complementary overlapping flange shapes. Here, the superior portions 300, 302 of the middle and inferior implants 296, 298 have an anterior configuration while the inferior portions 304, 306 of the middle and superior implants 296, 294 have a posterior orientation.

C. Implantation Procedure

In one embodiment of the invention, the patient is intubated and general anesthesia is achieved. The patient is prepped and draped in the usual sterile fashion. An anterior approach to the spine is used to expose the anterior vertebral bodies. Many anterior approaches to the vertebral column are described in various medical texts such as Campbell's Operative Orthopaedics, 10th ed., edited by Canale et al., pp. 1569-1588, herein incorporated by reference. In one embodiment, the upper cervical spine is accessed. The anterior upper cervical spine may by a transoral or retropharyngeal route, or by using a subtotal or extended maxillotomy. In other embodiments, the lower cervical spine, cervicothoracic junction, thoracic spine, thoracolumbar junction, lumbar region, lumbosacral junction, sacrum or combination of the above regions are accessed.

The intervertebral space is debrided. The flanged interbody implant is optionally packed with natural or artificial bone matrix and/or other osteogenesis factors and inserted into the intervertebral space. The flange is positioned against the anterior cervical vertebral bodies and attached with screws or anchors. The operative site is irrigated with antibiotics and the operative field is sutured closed. The vertebral column is accessed and one or more intervertebral spaces are identified and accessed. In some embodiments, two or more intervertebral spaces are accessed, and in still other embodiments, two or more adjacent intervertebral spaces are accessed. The operative site is rinsed with antibiotic solution and the operative field is closed in layers.

In another embodiment, the invention comprises the steps of providing an intervertebral implant system comprising a first fixation plate and first spacer and a second fixation plate and spacer, wherein the lower portion of the first fixation plate has a complementary shape to a corresponding complementary shape at the upper portion of the second fixation plate.

D. Pivot Plate

In another embodiment of the invention, the interbody spacer and the fixation plate are configured to provide some degree of relative movement between each other. By providing some relative movement between the interbody spacer and fixation plate portions, the device may have improved securement to osseous structures with improved conformance to the existing anatomy at the site of implantation. FIGS. 26A through 26D depict one such embodiment, comprising a hinge joint 308 oriented to allow pivoting in the sagittal plane. In other embodiments of the invention, the hinge joint 308 may be oriented to allow pivoting in other planes such as the transverse plane, coronal plane, or any plane in between the three planes. The joint provided between the interbody spacer 114 and the fixation plate 102 may be further configured to limit the range of movement provided. In other embodiments, the configuration of the interbody spacer 114 and/or fixation plate 102 may restrict the relative range of motion between the two components. Recesses in the fixation plate 102 or a size reduction or tapering of the interbody spacer component 114 about the movement joint 308 may allow greater movement. One of skill in the art will understand that the movement joint 308 may be configured to vary other characteristics of the movement joint, including frictional resistance or ratchet-type resistance to movement. Although the hinge joint in FIGS. 26A to 26D are depicted in a symmetric position on the interbody space and fixation plate, an eccentric location may be used. Moreover, although a single interbody spacer 114, fixation plate 102 and movement joint 308 are depicted, other embodiments will have two or more movement joints 308 and wherein either the fixation plate 102 and/or interbody spacer 114 may have a split configuration so that each split component has its own movement joint 308 and can independently move or pivot to provide additional conformance to the existing anatomy. In still other embodiments, the fixation plate 102 and/or interbody spacer 114 may be configured with two or more subcomponents that are provided with an intracomponent hinge or movement joint to provide better conformance of the device to the existing anatomy. For example, the fixation plate component of the device may be configured as left and right subcomponents with a hinge joint in between. In another example, the interbody spacer may have superior and inferior subcomponents with a hinge joint therebetween to allow pivoting of the superior and inferior surfaces of the interbody spacer. Depending on the orientation of the hinge joint, the superior and inferior surfaces of the interbody spacer may pivot laterally or in an anterior-posterior direction, or any direction in between.

Although a hinge-type movement joint is depicted in FIGS. 26A to 26D, other types of joints or connections between the interbody spacer component and fixation plate are also contemplated, including but not limited to a ball-and-socket joint or one or more metallic cords embedded or attached between the fixation plate and interbody spacer to allow limited polyaxial movement.

E. Alternative Screw Locks

In addition to the embodiments of the screw retaining assemblies described above, other screw retaining assemblies are also contemplated and may be used with the interbody fusion devices previously described. The other screw retaining assemblies described below may also be used with other types of orthopedic and medical devices, as well as non-medical applications, including but not limited to construction, home improvement, consumer appliance, electronic device and other applications.

1. Screw Retainer with Pivot Surface

Figure 27:
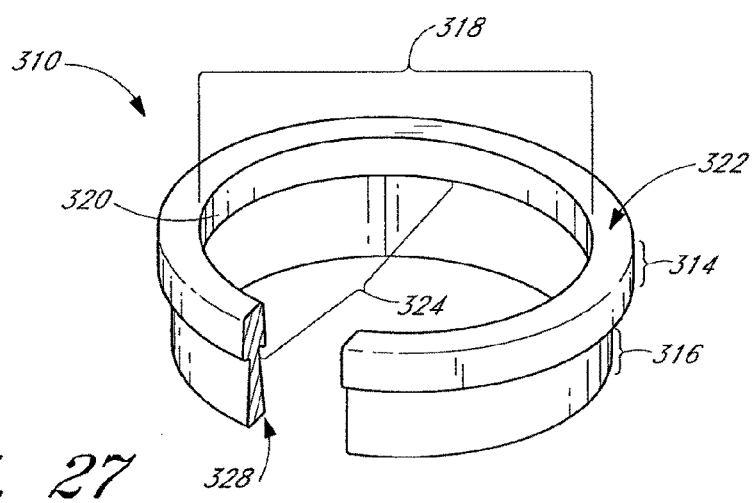
FIG. 27 is isometric elevational view of another embodiment of a fastener retaining assembly.
Figure 28:
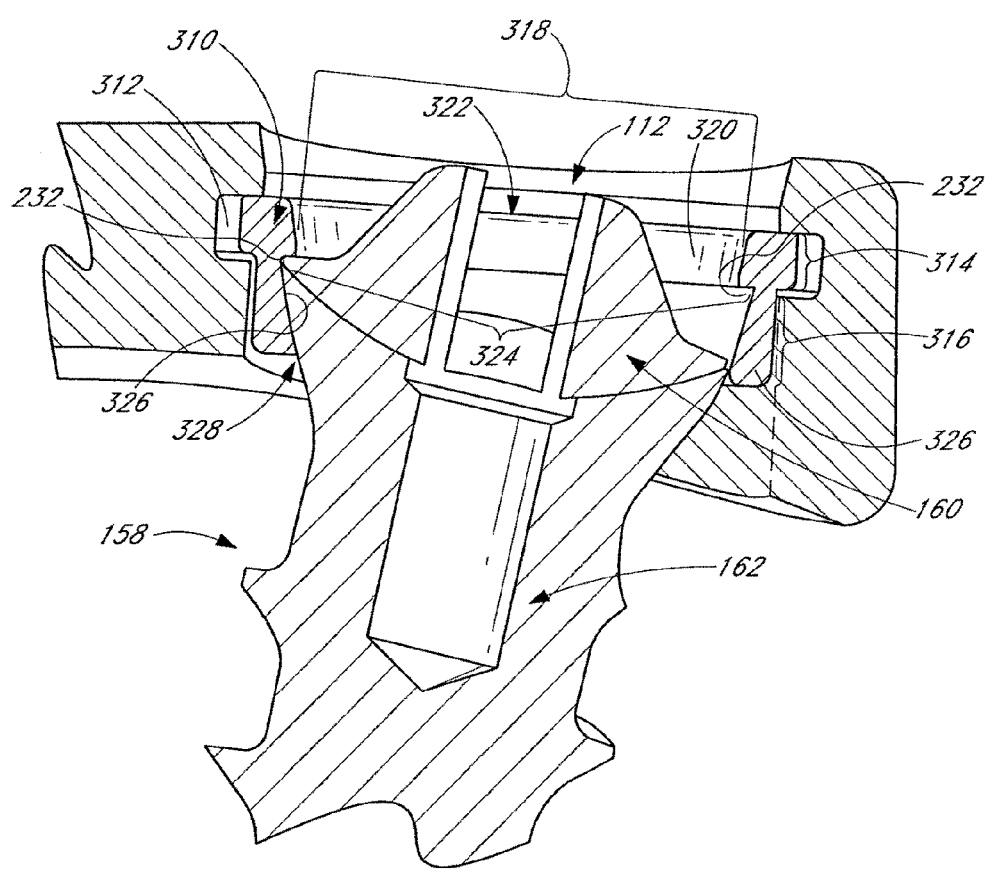
FIG. 28 is a cross-sectional view of a fixation device with the fastener retaining assembly of FIG. 27 and an inserted screw.

FIGS. 27 and 28 depict an alternative embodiment of the invention comprising an expandable fastener retaining ring 310 residing partially within an expansion groove 312 of a fastener lumen 112 and partially within the fastener lumen 112 itself. The retaining ring 310 has a reduced configuration and an expanded configuration but is biased to the reduced configuration. The retaining ring 310 has a retaining segment 314 and a pivot segment 316. Referring to FIG. 28, the retaining segment 314 has an enlarged outer diameter that is adapted to fit in an expansion groove 312. In the expanded configuration of the retaining ring 310, the retaining segment 314 further expands into the expansion groove 312, thereby increasing the inner diameter 318 of the retaining segment 314. The inner diameter 318 of the retaining segment 318 has a sloped inner surface 320 that narrows from the proximal opening 322 of the retaining ring 310. The sloped surface 320 facilitates expansion of the retaining segment 314 as a fastener 158 is inserted through it. Once the fastener head 160 has passed through the retaining segment 314 of the retaining ring 310, the inner diameter 324 of the polyaxial segment 316 of the retaining ring 310 is larger, allowing the fastener head 160 to reside in the retaining ring 310 without exerting an expansion force against the retaining ring 310. This allows the retaining ring 310 to at least partially, if not completely, revert back to its reduced configuration. If backout forces are exerted on the fastener head 160, the fastener head 160 will abut a generally perpendicular retaining surface 232 located at the transition from the inner diameters 318, 324 of the retaining and polyaxial segments 314, 316 of the ring 310 and will resist fastener head 160 backout.

The polyaxial segment 316 of the retaining ring 310 comprises a sloping reduced diameter 326 towards the distal opening 328 of the retaining ring 310, such that the smallest diameter of the polyaxial segment 316 is smaller than the largest diameter of the fastener head 160 and prevents or resists the fastener head 160 from passing completely through the retaining ring 310. The slope of the cross-section through the retaining ring may be linear, curved, toothed or jagged or any other sloped surface.

2. Fastener Head Embedded Expansion Lock

Figure 29A:
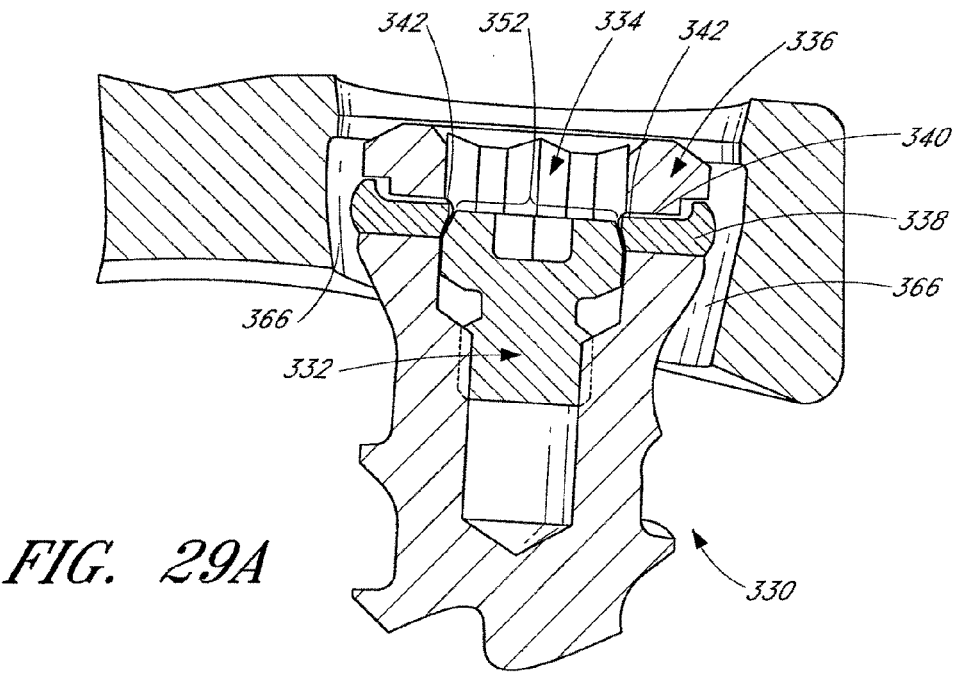
FIG. 29A is a cross-sectional view of another embodiment of a fastener with an expansion ring.
Figure 29B:
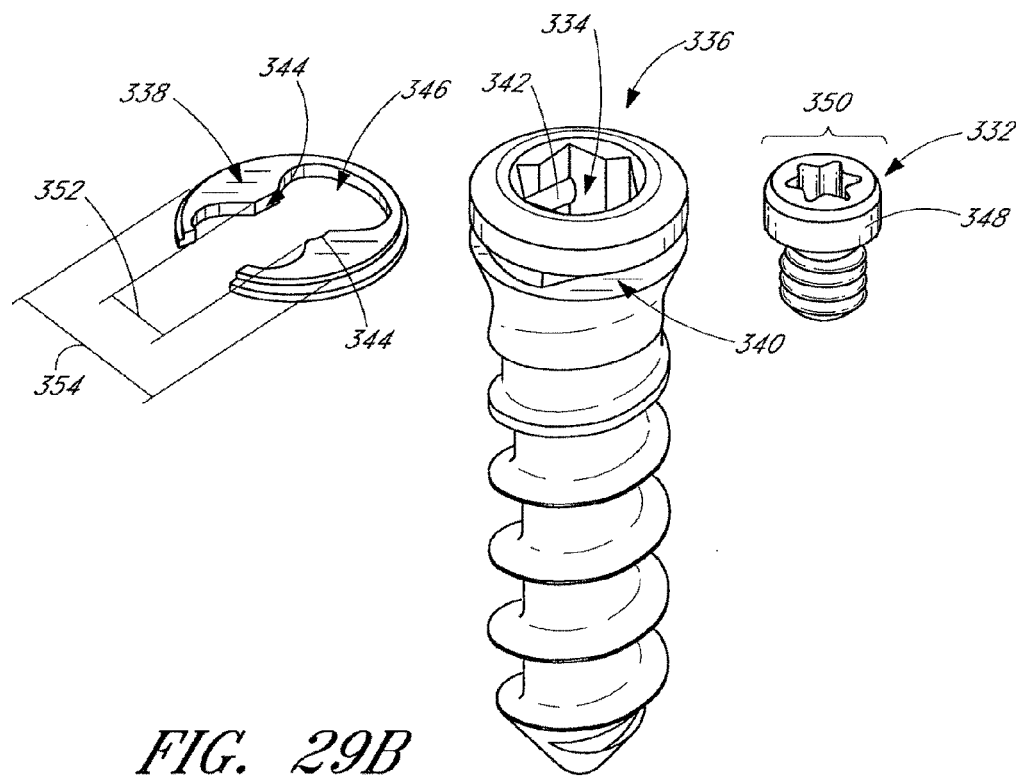
FIG. 29B is an exploded view of the fastener and expansion ring in FIG. 29A.

In another embodiment of the invention, illustrated in FIGS. 29A and 29B, the fastener 330 comprises a secondary screw 332 and screw lumen 334 within the fastener head 336. An expandable ring 338 or disc, having a reduced and an expanded configuration, is provided within a groove 340 about the fastener head 336, with the expandable ring or disc biased to the reduced configuration. The groove 340 is contiguous with screw lumen 334 of the fastener head 336 at one or more openings 342, such that the portion 344 of the inner surface 346 of the expandable ring 338 or disc partially protrudes into the screw lumen 334 when the expandable ring 338 or disc is in the reduced configuration. The secondary screw 332 of the fastener 330 has an expansion section, typically the head 348 of the secondary screw 332, which has an outer diameter 350 that is greater than the distance 352 within the screw lumen 334 where the expansion ring 338 or disc protrudes into the screw lumen 334. When the expansion section 348 of the secondary screw 332 is not in contact with the inner protruding portions 344 of the expandable ring 338 or disc, the expandable ring 338 or disc is able to remain in the reduced configuration. When the expansion section 348 of the secondary screw 332 is fully positioned against the protruding portions 344 of the expandable ring 338 or disc, it acts against the expandable ring 338 or disc and causes the expandable ring 338 or disc to enlarge to its expanded configuration. In the expanded configuration, the outer diameter 354 of the expandable ring 338 or disc is greater than the largest outer diameter of the remaining portions of the fastener 330. In the reduced configuration, the outer diameter of expandable ring or disc may or may not radially extend from out of the groove.

Figure 37:
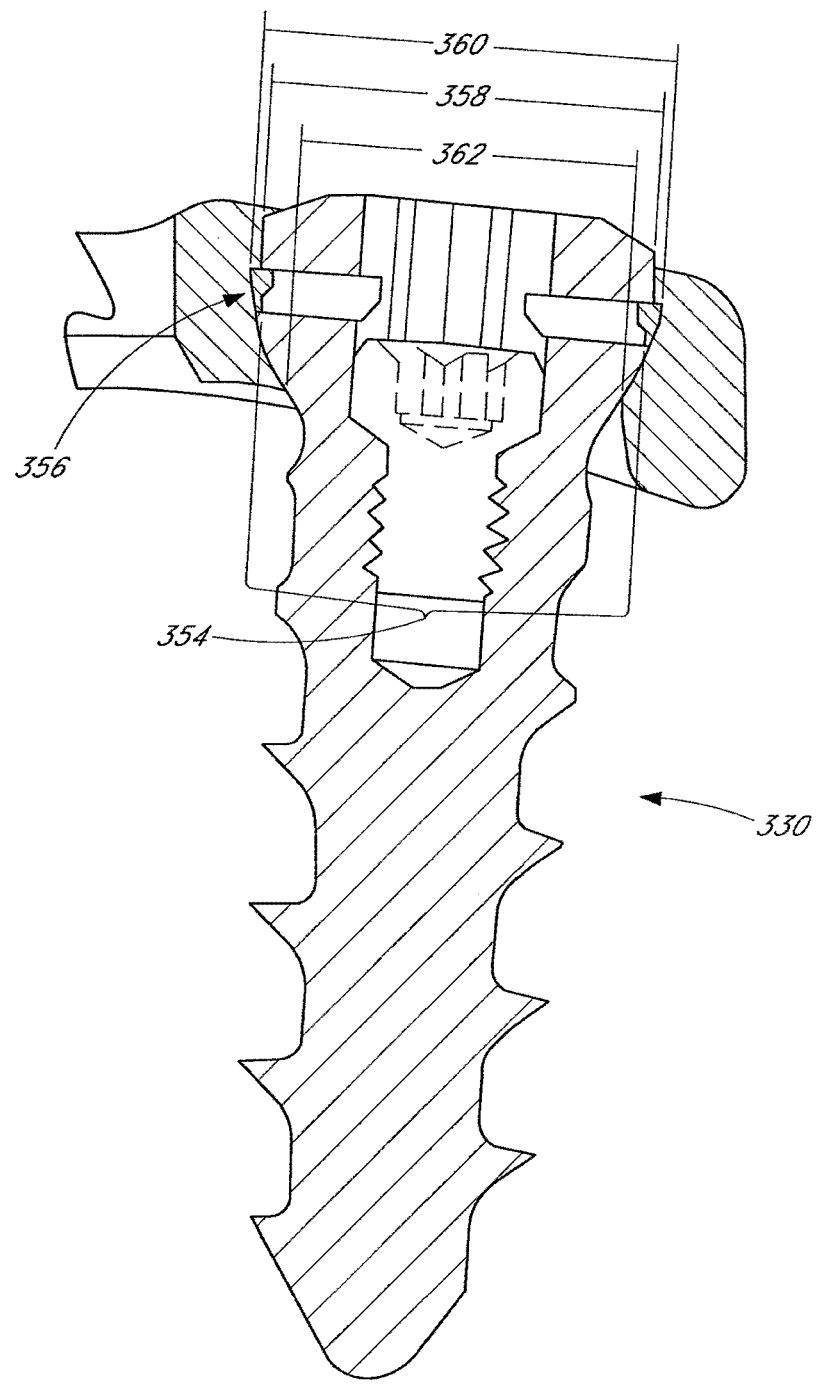
FIG. 37 is a cross-sectional view of another embodiment of a fastener with an expansion ring.

Referring to FIG. 37, the fastener 330 is preferably used in devices having one or more fastener lumens 356 with a proximal diameter 358, middle diameter 360 and distal diameter 362, wherein the proximal diameter 358 is greater than the distal diameter 362 but less than the middle diameter 360, and wherein the proximal diameter 358 is less than the outer diameter 364 of the expandable ring 354 or disc in the reduced configuration. The outer diameter of the expandable ring 338 or disc, in the expanded configuration, is larger than the proximal diameter 358 of the fastener lumen 356, thereby preventing or resisting backout of the fastener 330. In other embodiments, as shown in FIG. 29A, the screw lumen may be lined by an hole insert 366 having a similar relationship of its proximal, middle and distal diameters. A hole insert 366 may be preferred, for example, when the orthopedic device utilizing the fastener system comprises a material that may exhibit wear from the metallic fasteners. A hole insert 366 may be provided to protect against such wear.

Referring again to FIG. 29A, the screw lumen 334 of the fastener 330 typically but is not required to extend distally from the openings 342 contiguous with the fastener head groove 340 to allow the secondary screw 332 to completely reside within the screw lumen 334 in a position distal to the screw lumen openings 342 and inner protrusions 344 of the expandable ring 338 or disc. This allows the fastener 330 to be attached to the desired structure without having to later insert the secondary screw 332 into the fastener 330 to enlarge the expandable ring 338 or disc. Instead, once the fastener 330 is attached to the desired structure, the secondary screw 332 need only be moved proximally in the screw lumen 334 to act against the expandable ring 338 or disc and enlarge the expandable ring 338 or disc to its expanded configuration and to retain the fastener in place. By allowing the attachment of the fastener 330 with the secondary screw 332 already in place, the use of fastener 330 in cramped or limited access areas, such as the attachment of a cervical fusion plate or interbody fusion device, need not attempt to maintain a tiny secondary screw 332 on the end of an attachment device while attempting to align the tiny secondary screw 332 with the screw lumen 334 of the fastener head. The user of the fastener 330 only has to align the screwdriver of the secondary screw to the secondary screw in order to manipulate it.

3. Side-Biased Screwhead Lock

Figure 30A:
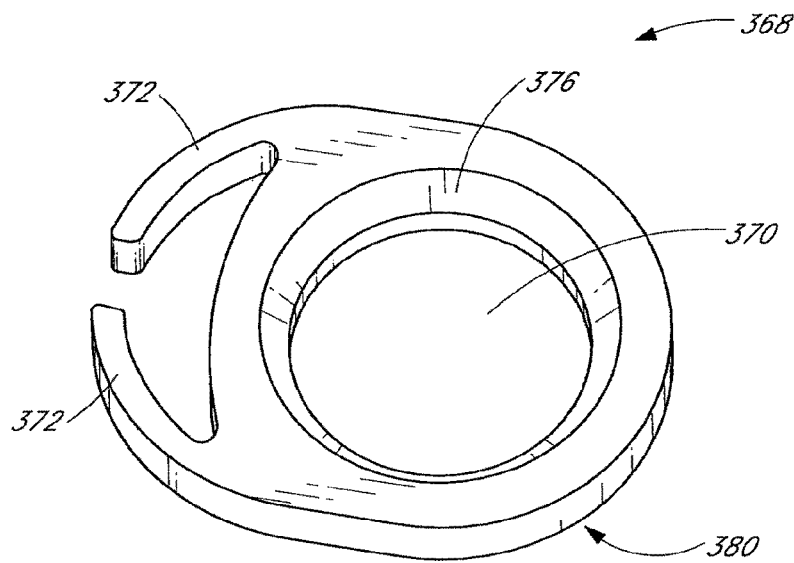
FIGS. 30A and 30B are superior oblique views of a fastener retaining body with side-bias members in uncompressed and compressed positions, respectively.
Figure 30B:
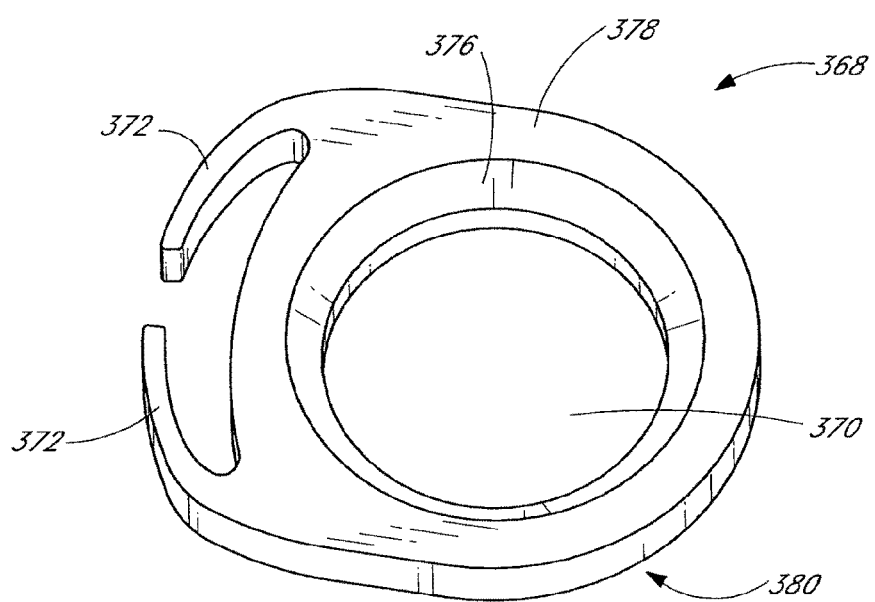
Figure 31:
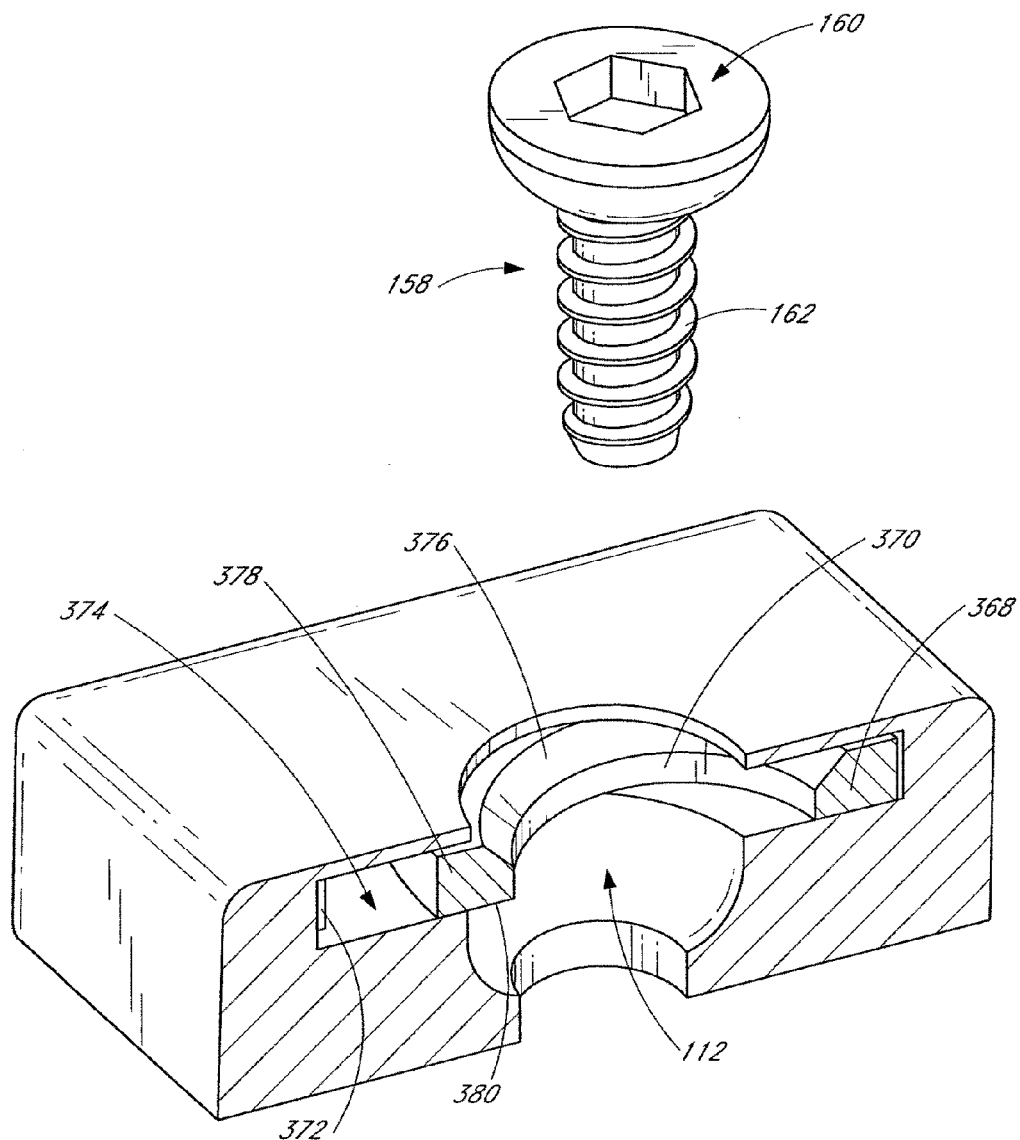
FIG. 31 is an oblique cut-away view of the fastener retaining body in FIG. 30A within a retaining body space about a fastener lumen.
Figures 33A, 33B:
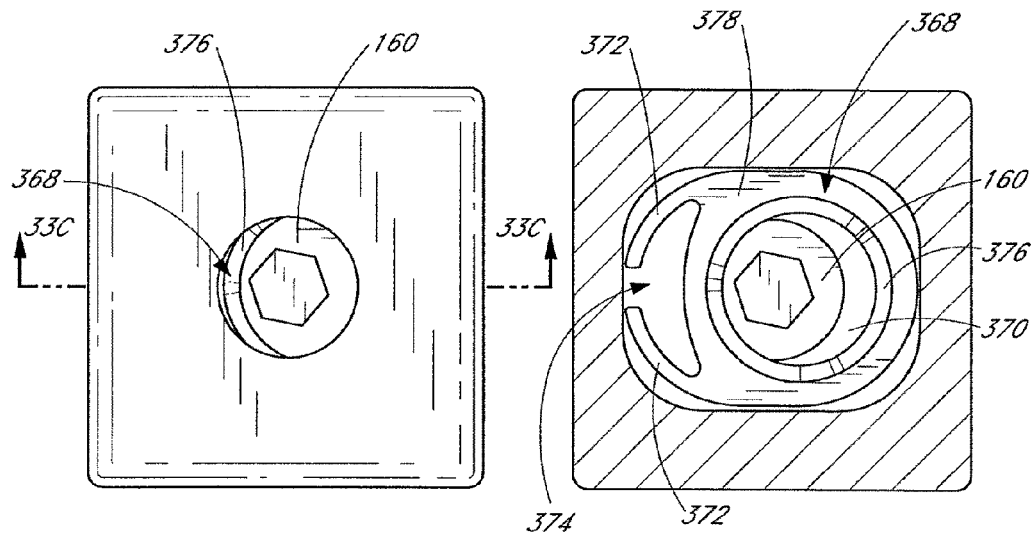
FIG. 33A is a superior elevational of a fastener head positioned within a fastener lumen whereby the fastener head has fully passed through the fastener retaining body and the fastener retaining body has reverted to its uncompressed configuration.
FIGS. 33B and 33C are superior side cross-sectional views of fastener head and fastener retaining body from FIG. 33A.
Figure 33C:
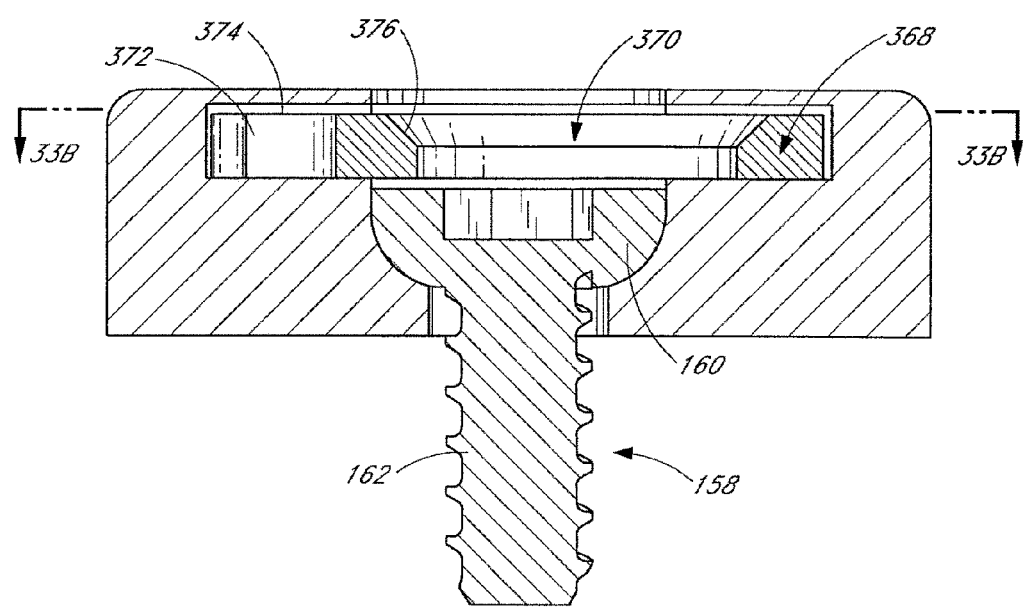

In another embodiment of the invention, the screw retaining assembly comprises a biased blocking body residing in an access space about a fastener lumen. Referring to FIGS. 30A and 30B, the blocking body 368 comprises a structure with a fixed opening 370 sized to allow passage of a fastener 158. The blocking body 368 further comprises one or more bias members 372 that are biased to an uncompressed configuration in FIG. 30A, but wherein the bias may be overcome to move the bias members 372 to a compressed configuration as in FIG. 30B. FIG. 31 illustrates the blocking body 368 in FIGS. 30A and 30B located about a fastener lumen 112 in the uncompressed configuration. In FIGS. 32A to 32C, the blocking body 368 has a first position within an access space 374 that allows passage of a fastener body 162 through the opening 370 in the blocking body 368. The opening 370 of the blocking body 368 preferably has a narrowing sloped surface 376 from its proximal face 378 toward its distal face 380 to facilitate the displacement of the blocking body 368 to its compressed configuration as the fastener head 160 is inserted into the opening 370 of the blocking body 368. FIGS. 33A to 33C illustrate a second position of the blocking body 368 within the access space 374 that prevents or resists passage of the fastener head 160 past the blocking body 368.

Although the embodiments of the invention depicted in FIGS. 30A to 33C illustrate a blocking body 368 comprising a generally looped structure, one of skill in the art will understand that only a portion of the loop serves a blocking function, and therefore, in other embodiments of the invention, the blocking body may be a partial loop, or any other shaped structure configured to protrude into the fastener lumen 112 or passageway in an uncompressed configuration and not protrude into the fastener lumen 112 or passageway in the compressed configuration. The blocking body 368 need not be curved or looped. Furthermore, although the bias members 372 depicted FIGS. 30A to 33C are attached to the blocking body 368, one of skill in the art will understand that the bias structures used to bias the blocking body to its second position need not be attached to the blocking body. Instead, the bias structures may be attached to one of more surfaces of the access space, or reside in the access space but is not attached to any structure. For example, the access space may contain a separate blocking body and bias structure, such as a helical or leaf spring, that exerts an expansion force between a surface of the access space and blocking body to bias the blocking body in the second position.

4. Lock Plate

Figure 34A:
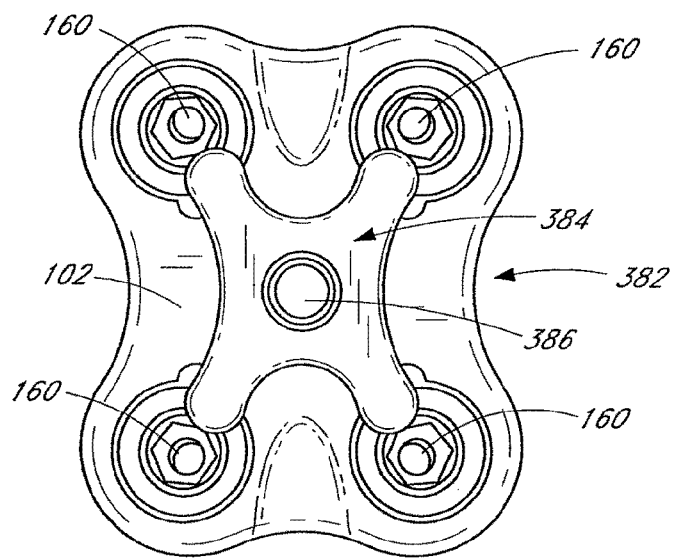
FIG. 34A is an anterior elevational view of one embodiment of the invention comprising a locking plate and flanged interbody fusion device.
Figure 34B:
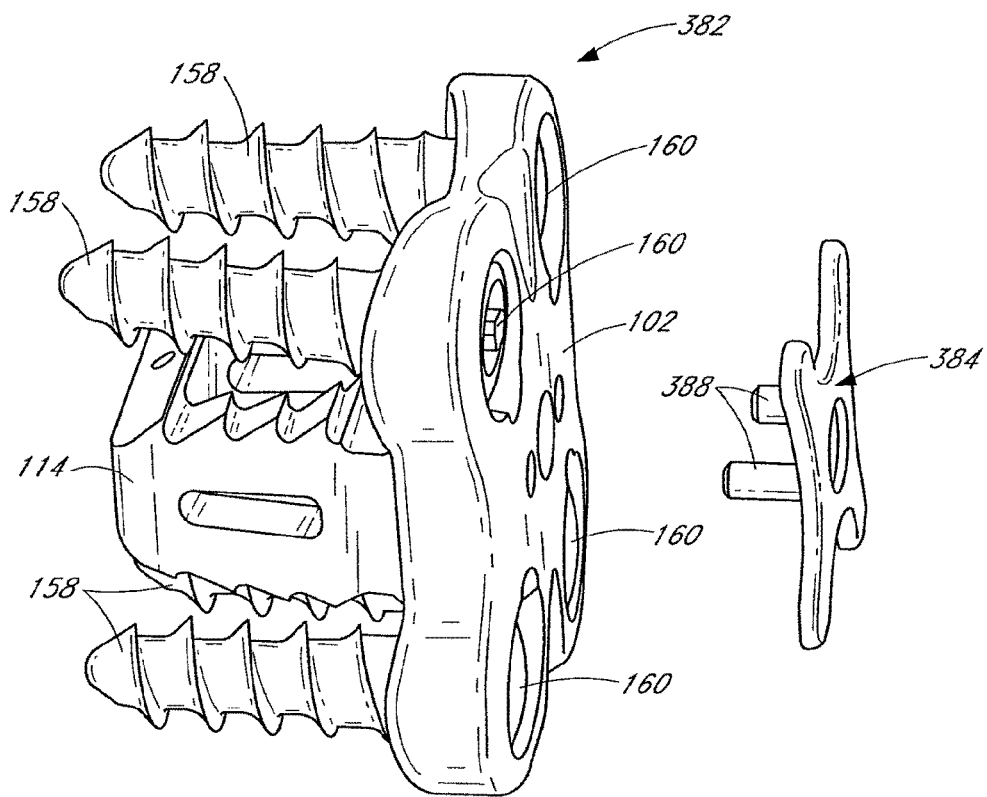
FIG. 34B depicts the locking plate of FIG. 34A separated from the flanged interbody fusion device.

In another embodiment of the invention, some embodiments of the flanged interbody fusion device 382 may comprise locking plates 384 that may be attached to the fixation plate 102 to overlie at least portion of one or more bone screws 158 or fastener heads 160 to prevent or resist backout. FIGS. 34A and 34B represent one embodiment of the invention with an X-shaped locking plate 384 attachable to the fixation plate 102 using a fastener 386. Other locking plate configurations may also be used, depending on the particular arrangement and number of the bone screws used to fasten the device to the bone. As shown in FIG. 34B, the locking plate 384 may comprise one or more alignment structures 388 that prevent the locking plate 384 from spinning as the fastener 386, typically a screw, is rotated to engage the locking plate 384 to the fixation plate 102. The alignment structures typically but not necessarily will interface with complementary structures on the fixation plate 102. In other embodiments, a fastener may not be required as the alignment structures or other portions of the fastener may form a snap fit with the fixation plate 102.

Figure 35B:
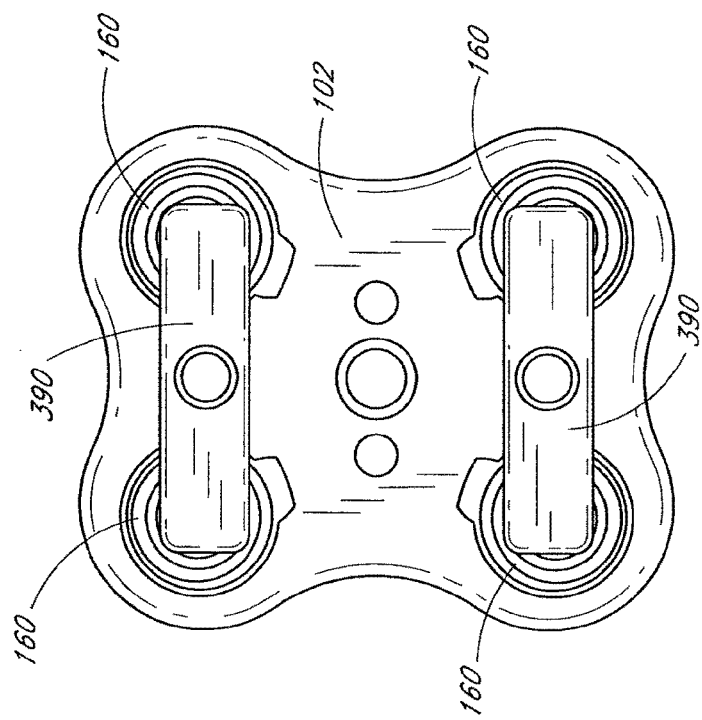
FIGS. 35A and 35B are oblique and anterior elevational views of another embodiment of the invention comprising dual locking plates.
Figure 35A:
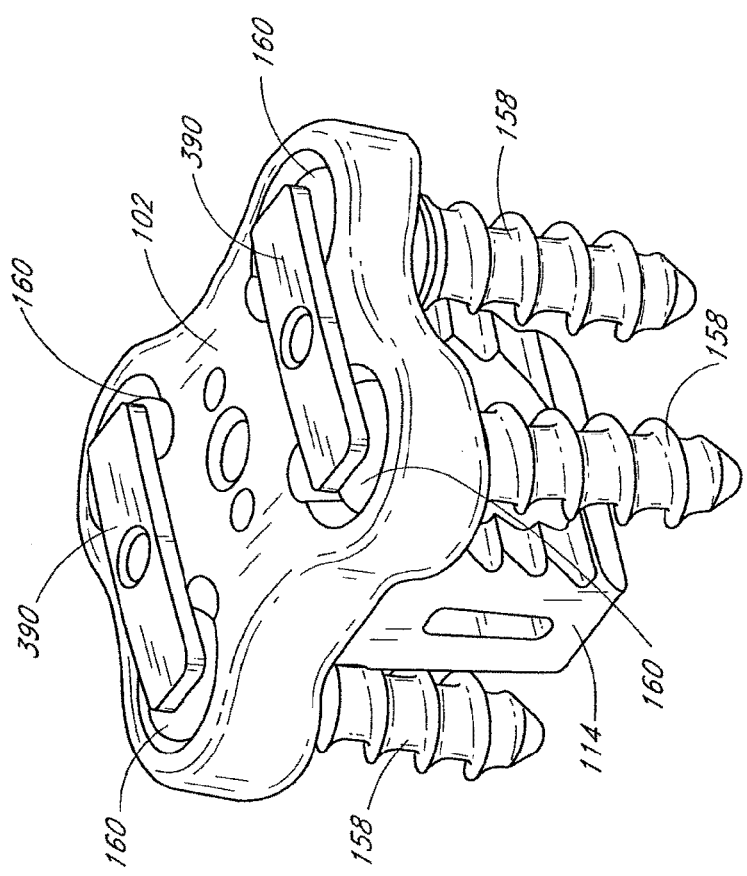
Figure 36B:
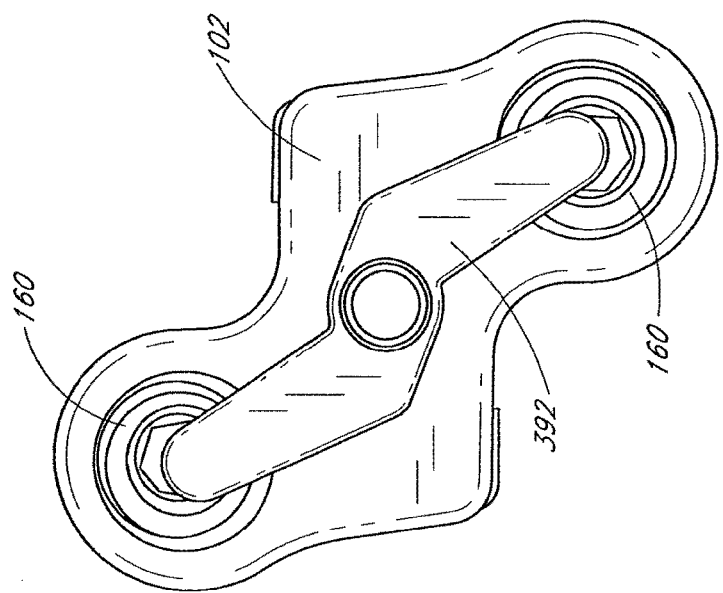
FIGS. 36A and 36B are side and anterior elevational view of another embodiment of the invention comprising an angled locking plate.
Figure 36A:
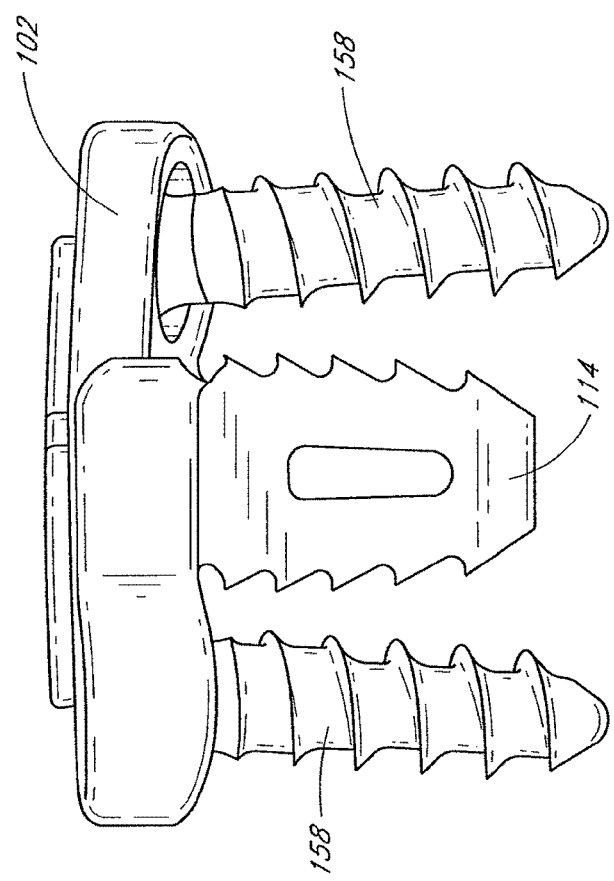

As depicted in FIGS. 35A and 35B, more than one locking plate 390 may be used. As shown in FIGS. 36A and 36B, the locking plates 392 may be angled or otherwise shaped for a particular fixation plate configuration.

F. Conclusion

Although the present invention has been described in relation to various exemplary embodiments, various additional embodiments and alterations to the described embodiments are contemplated within the scope of the invention. Thus, no part of the foregoing description should be interpreted to limit the scope of the invention as set forth in the following claims. For all of the embodiments described above, the steps of the methods need not be performed sequentially.

What is claimed is:

1. A fastener, comprising:
    a proximal fastener head and fastener shaft having a tip distal to the fastener head, the fastener head comprising a screw lumen, an external groove and one or more openings between the screw lumen and external groove, and an expandable member located at least partially in the external groove and protruding through the one or more openings into the screw lumen; and
    a secondary screw configured for the screw lumen comprising a screw body with threads and a screw head having an angled edge;
    wherein the screw lumen is configured such that the secondary screw may in a distal position reside in a position completely distal to a screw lumen opening and expandable member such that the expandable member is in a resting position and when rotated from said completely distal position into a proximal position the secondary screw angled edge resides in a position about the external groove such that the expandable member enlarges to an expanded configuration in which an outer diameter of the expandable member is greater than a largest outer diameter of the fastener.

2. The fastener as in claim 1, wherein the expandable member is a ring.

3. An orthopedic fastening system, comprising:
    a fastener comprising a proximal fastener head and a threaded fastener body having a tip distal to the fastener head, wherein the fastener head comprises a lumen opening, a central internal lumen contiguous with the lumen opening, a side lumen contiguous with the central internal lumen and an expansion member located at least partially within the side lumen and having an expanded configuration and a reduced configuration;
    wherein the fastener head further comprises an internal screw comprising a screw body with threads and a screw head having an angled edge located within the central internal lumen, the internal screw having a proximal position and a distal position, wherein, in the distal position, the internal screw is located completely distal to the side lumen such that the expansion member is in the reduced configuration and, when rotated from said completely distal position into the proximal position, the internal screw head is located about the side lumen and the angled edge displaces the expansion member into the expanded configuration.

4. The orthopedic fastening system as in claim 3, wherein the proximal position of the internal screw at least partially displaces the expansion member out of the side lumen.

5. The orthopedic fastening system as in claim 3, wherein the expansion member in the reduced configuration is partially located in the central internal lumen.

6. The orthopedic fastening system as in claim 5, wherein the proximal position of the internal screw at least partially displaces the expansion member out of the central internal lumen.

7. The orthopedic fastening system as in claim 3, wherein the expansion member is biased to the reduced configuration.

8. The orthopedic fastening system as in claim 3, wherein the fastener head further comprises an expansion groove contiguous with the side lumen and the expansion member comprises an elongate body positioned about the expansion groove.

9. The orthopedic fastening system as in claim 8, wherein the elongate body is an arcuate elongate body.

10. The orthopedic fastening system as in claim 8, wherein the expansion member further comprises a radial elongate body located at least partially in the side lumen.

11. The orthopedic fastening system as in claim 3, further comprising an orthopedic device comprising a fastener lumen adapted to retain the fastener.

12. The orthopedic fastening system as in claim 11, wherein the fastener lumen comprises a proximal diameter, a middle diameter and a distal diameter, wherein the proximal diameter is smaller than the middle diameter.

13. The orthopedic fastening system as in claim 12, wherein the distal diameter of the fastener lumen is smaller than the proximal diameter of the fastener lumen.

14. The orthopedic fastening system as in claim 11, wherein the fastener lumen comprises a hole insert.

15. The orthopedic fastening system as in claim 14, wherein the hole insert comprises a proximal diameter, a middle diameter and a distal diameter, wherein the proximal diameter is smaller than the middle diameter.

16. The orthopedic fastening system as in claim 11, wherein the orthopedic device is an interbody spacer.

17. The orthopedic fastening system as in claim 16, wherein the interbody spacer is a flanged interbody spacer.

18. The orthopedic fastening system as in claim 11, wherein the orthopedic device is a fixation plate.

19. The orthopedic fastening system as in claim 18, wherein the orthopedic device is a vertebral fixation plate.

20. The orthopedic fastening system as in claim 19, wherein the vertebral fixation plate is an anterior cervical fixation plate.

* * * * *

UNITED STATES PATENT AND TRADEMARK OFFICE
CERTIFICATE OF CORRECTION

PATENT NO. : 8,696,721 B2  
APPLICATION NO. : 13/333652  
DATED : April 15, 2014  
INVENTOR(S) : Jason Blain et al.

Page 1 of 1

It is certified that error appears in the above-identified patent and that said Letters Patent is hereby corrected as shown below:

Title Page, Item (75) Inventors is corrected to read:
-- Jason Blain, Encinitas, CA (US); Greg Martin, Carlsbad, CA (US); --

Signed and Sealed this  
Nineteenth Day of May, 2015

Michelle K. Lee  
*Director of the United States Patent and Trademark Office*